(12) United States Patent
Hayward et al.

(10) Patent No.: US 6,207,664 B1
(45) Date of Patent: Mar. 27, 2001

(54) SQUALENE SYNTHETASE INHIBITOR AGENTS

(75) Inventors: Cheryl M. Hayward, Old Lyme; Douglas A. Scully, Noank, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/441,339

(22) Filed: Nov. 16, 1999

Related U.S. Application Data

(60) Provisional application No. 60/109,939, filed on Nov. 25, 1998.

(51) Int. Cl.$^7$ .................. A61K 31/55; A61K 31/553; A61K 31/554; C07D 487/06; C07D 491/06
(52) U.S. Cl. ....................... 514/212.05; 540/520
(58) Field of Search ................. 540/520; 514/212.05

(56) References Cited

FOREIGN PATENT DOCUMENTS

| 0567026 | 10/1993 | (EP) . |
|---|---|---|
| 0645378 | 3/1995 | (EP) . |
| 0705607 | 4/1996 | (EP) . |
| 0710725 | 5/1996 | (EP) . |
| 0645377 | 8/1997 | (EP) . |
| 0611749 | 10/1997 | (EP) . |
| WO9609827 | 4/1996 | (WO) . |

OTHER PUBLICATIONS

Scott A. Biller, et, al., Current Pharmaceutical Design, 1996 Vol. 2, #1, pp. 1–40, "Squalene Synthase Inhibitors".

G. Popjak, Meth. Enzymol. 1969; 15: 393–454 "[12] Enzymes of Sterol Biosynthesis in Liver and Intermediates of Sterol Biosynthese".

William S. Agnew, Meth. Enzymol. 1985; 110: 359–373, "[41]squalene Synthetase".

*Primary Examiner*—Bruck Kifle
(74) *Attorney, Agent, or Firm*—Peter C. Richardson; Gregg C. Benson; A. Dean Olson

(57) ABSTRACT

This invention relates to certain squalene synthetase inhibitors useful as hypocholesterolemic agents, hypotriglyceridemic agents, antiatherosclerosis agents, antifungal agents, anti-Alzheimer's agents or anti-acne agents.

35 Claims, No Drawings

SQUALENE SYNTHETASE INHIBITOR AGENTS

This application claims priority from provisional application U.S. Ser. No. 60/109,939 filed Nov. 25, 1998, the benefit of which is herby claimed under 37 C.F.R. §1.78(a)(3).

BACKGROUND OF THE INVENTION

This invention relates to squalene synthetase inhibitors, pharmaceutical compositions containing such inhibitors and the use of such inhibitors to treat hypercholesterolemia, hypertriglyceridemia, atherosclerosis, fungal infections, acne and Alzheimer's disease in mammals, including humans.

Plasma cholesterol levels have been positively correlated with the incidence of clinical events associated with coronary heart disease (CHD). Thus, pharmacological interventions that reduce cholesterol levels in mammals have a beneficial effect on CHD. In particular, decreased plasma low density lipoprotein (LDL) cholesterol levels are associated with decreased atherosclerosis and a decreased risk of CHD, and hypolipidemic agents used in either monotherapy or combination therapy are effective at reducing plasma LDL cholesterol levels and the subsequent risk of CHD.

Cholesterol metabolism in mammals involves a series of pathways including cholesterol absorption in the small intestine, cholesterol biosynthesis in numerous tissues (primarily the liver and small intestine), bile acid biosynthesis in the liver and reabsorption in the small intestine, synthesis of cholesterol-containing plasma lipoproteins by the liver and intestine, catabolism of the cholesterol-containing plasma lipoproteins by the liver and extrahepatic tissues and secretion of cholesterol and bile acids by the liver.

Cholesterol synthesis occurs in multiple tissues, but principally in the liver and the intestine. It is a multistep process starting from acetyl-coenzyme A catalyzed by a series of enzymes including hydroxymethylglutaryl-coenzyme A (HMG-CoA) reductase, HMG-CoA synthase, squalene synthetase, squalene epoxidase, squalene cyclase and lanosterol demethylase. Inhibition of catalysis by these enzymes or blocking HMG-CoA reductase gene expression is recognized as an effective means to reduce cholesterol biosynthesis (thus inhibitors thereof are referred to as cholesterol synthesis inhibitors) and can lead to a reduction in cholesterol levels. For example, there are known HMG-CoA reductase inhibitors (e.g., lovastatin, simvastatin, pravastatin, fluvastatin, atorvastatin, rivastatin, cerivastatin, nisvastatin) that are used for the treatment of hypercholesterolemia.

In fungi, the principal sterol is ergosterol, which is synthesized by a similar multi-step process to cholesterol. Inhibition of catalysis by these enzymes is recognized as an effective means of preventing fungal growth, both in vitro and in vivo. For example, there are known inhibitors of lamosterol demethylase (e.g., fluconazole, voriconazole, ketoconazole, itraconazole) and squalene epoxidase (e.g., terbinafine, naftifine, butenafine) which are used for the treatment of fungal infections.

Recently adopted National Cholesterol Education Program guidelines recommend aggressive lipid-lowering therapy for patients with pre-existing cardiovascular disease or for those with multiple factors that place them at increased risk.

The term squalene synthetase inhibitor refers to compounds that inhibit the condensation of 2 molecules of farnesylpyrophosphate to form squalene, a reaction that is catalyzed by the enzyme squalene synthetase. Such inhibition is readily determined by those skilled in the art according to standard assays (Meth. Enzymol. 1969; 15: 393–454 and Meth. Enzymol. 1985; 110:359–373 and references contained therein). A summary of squalene synthetase inhibitors has been compiled (Current Pharmaceutical Design 1996, 1, 1–40). European patent publication 0 567 026 A1 discloses certain 4,1-benzoxazepine derivatives as squalene synthase inhibitors and their use in the treatment of hypercholesterolemia and as fungicides. European patent publication 0 645 378 A1 discloses certain condensed seven- or eight-membered heterocycles as squalene synthetase inhibitors and their use in treatment and prevention of hypercholesterolemia and fungal infections. European patent publication 0 645 377 A1 discloses certain benzoxazepine derivatives as squalene synthetase inhibitors useful for the treatment of hypercholesterolemia or coronary sclerosis. European patent publication 0 611 749 A1 discloses certain substituted amic acid derivatives useful for treatment of arteriosclerosis. European patent publication 0705607 A2 discloses certain condensed seven- or eight-membered heterocyclic compounds useful as antihypertriglyceridemic agents. PCT Publication WO 96/09827 discloses certain combinations of cholesterol absorption inhibitors and cholesterol synthesis inhibitors including benzoxazepin derivatives and benzothiazepinone derivatives. European patent publication 0710725 A1 discloses a process for producing certain optically active compounds, including benzoxazepine compounds, having plasma cholesterol and triglyceride lowering activities.

Thus, although there are a variety of hypercholesterolemia therapies, there is a continuing need and a continuing search in this field of art for alternative therapies.

SUMMARY OF THE INVENTION

This invention is directed to certain squalene synthesis inhibitor compounds, prodrugs thereof, and pharmaceutically acceptable salts of said compounds and said prodrugs, useful for the treatment of hypercholesterolemia, hypertriglyceridemia, atherosclerosis, fungal infections, Alzheimer's disease and acne.

The compounds of this invention have the Formula I

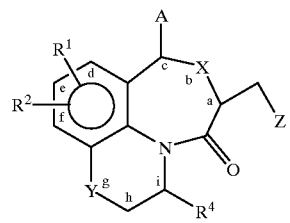

Formula I including prodrugs thereof, and pharmaceutically acceptable salts of said compounds and said prodrugs;

wherein A is phenyl or naphthyl, said phenyl or naphthyl optionally mono-, di- or tri-substituted independently with $R^3$, $R^9$ and $R^{10}$;

X is oxy or thio;

Y is oxy, thio or methylene;

$R^1$ and $R^2$ are each independently hydrogen, halo, hydroxyl, trifluoromethyl, $(C_1–C_4)$alkyl, fluorinated $(C_1–C_4)$alkyl having from 1 to 9 fluorines, $(C_1–C_4)$alkoxy, fluorinated $(C_1–C_4)$alkoxy having from 1 to 9 fluorines, $(C_1-C_4)$alkylthio, $(C_1-C_4)$alkylsulfinyl, $(C_1-C_4)$alkylsulfonyl, phenyl, amino, mono-N- or di-N,N-$(C_1-C_4)$alkylamino, carboxyl, $(C_1-C_4)$alkoxycarbonyl, carbamoyl, mono-N- or di-N,N-$(C_1-C_4)$alkylcarbamoyl, $(C_1-C_4)$alkanoylamino, fluorinated $(C_1-C_4)$alkanoylamino having from 1 to 9 fluorines, $(C_1-C_4)$alkylsulfonylamino or fluorinated $(C_1-C_4)$alkylsulfonylamino having from 1 to 9 fluorines, $(C_1-C_6)$alkanoyl, $(C_1-C_6)$alkanoyl$(C_1-C_6)$alkyl, oxazolyl, thiazolyl, isoxazolyl, pyrazolyl or isothiazolyl wherein said preceding heterocycles are carbon linked or wherein $R^1$ and $R^2$ can be taken together to form a five, six or seven membered carbocyclic ring or can be taken together to form methylenedioxyl, ethylenedioxyl or propylenedioxyl and such rings formed by taking $R^1$ and $R^2$ together are fused at the e and f positions;

$R^3$, $R^9$ and $R^{10}$ are each independently hydrogen, halo, hydroxyl, trifluoromethyl, $(C_1-C_4)$alkyl, fluorinated $(C_1-C_4)$alkyl having from 1 to 9 fluorines, $(C_1-C_4)$alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, phenyl, amino, mono-N- or di-N,N-$(C_1-C_4)$alkylamino, carboxyl, $(C_1-C_4)$alkoxycarbonyl, carbamoyl, mono-N- or di-N,N-$(C_1-C_4)$alkylcarbamoyl, $(C_1-C_4)$alkanoylamino, fluorinated $(C_1-C_4)$alkanoylamino having from 1 to 9 fluorines, $(C_1-C_4)$alkylsulfonylamino or fluorinated $(C_1-C_4)$alkylsulfonylamino having from 1 to 9 fluorines, $(C_1-C_6)$alkanoyl, $(C_1-C_6)$alkanoyl$(C_1-C_6)$alkyl, oxazolyl, thiazolyl, isoxazolyl, pyrazolyl or isothiazolyl wherein said preceding heterocycles are carbon linked or wherein $R^3$ and $R^9$ can be taken together to form a five, six or seven membered carbocyclic ring or can be taken together to form methylenedioxyl, ethylenedioxyl or propylenedioxyl rings;

$R^4$ is phenyl, $(C_1-C_7)$alkyl, $(C_1-C_7)$alkenyl or $(C_3-C_4)$cycloalkylmethyl wherein said phenyl, $(C_1-C_7)$alkyl, $(C_1-C_7)$alkenyl or $(C_3-C_4)$cycloalkylmethyl are optionally mono-, di-, or tri-substituted independently with hydroxyl, oxo, $(C_1-C_4)$alkyl, amino, carboxy, thiol, $(C_1-C_4)$alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, mono-N- or di-N,N-$(C_1-C_4)$alkylamino, mono-N- or di-N,N-$(C_1-C_4)$alkylaminocarbonyl, or mono-N-or di-N,N$(C_1-C_4)$alkylaminosulfonyl; or $R^4$ is $(C_1-C_7)$alkyl substituted with 1 to 15 fluorines or $(C_3-C_4)$cycloalkylmethyl substituted with 1 to 9 fluorines; or $R^4$ is het$(C_1-C_6)$alkyl wherein het is a 4–7 member saturated, partially unsaturated or fully unsaturated heterocycle containing independently one to three O, N or S atoms and said het is optionally mono-substituted with $(C_1-C_4)$alkyl, $(C_1-C_4)$alkoxy, hydroxyl, halo, amino or mono-N- or di-N,N-$(C_1-C_4)$alkylamino;

Z is carboxyl, $(C_1-C_4)$alkoxycarbonyl, aminocarbonyl, cyano, hydroxyaminocarbonyl, —C(O)N(H)SO$_2$R$^5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl, N(R$^{12}$)CONR$^{13}$R$^{14}$, N(R$^{12}$)CO$_2$$(C_1-C_4)$alkyl, N(R$^{12}$)COR$^{15}$,

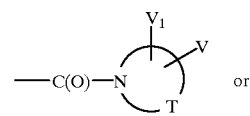

mono-N- or di-N,N-$(C_1-C_6)$alkylaminocarbonyl wherein each of said $(C_1-C_6)$alkyl is optionally mono- or di-substituted independently with V or V$^1$, or —C(O)N(H)—$(C_0-C_4)$alkyl-R$^{20}$ wherein said $(C_0-C_4)$alkyl may optionally be mono-substituted with carboxyl and wherein R$^{20}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said R$^{20}$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, wherein said $(C_1-C_6)$alkyl substituent is also optionally substituted with from one to nine flourines;

R$^{12}$, R$^{13}$ and R$^{14}$ are each independently H or $(C_1-C_4)$alkyl;

R$^{15}$ is H or $(C_1-C_4)$alkyl;

R$^5$ is H, amino or mono-N- or di-N,N-$(C_1-C_4)$alkylamino; or R$^5$ is $(C_1-C_4)$alkyl optionally substituted with 1 to 9 fluorines, amino, mono-N- or di-N,N-$(C_1-C_4)$alkylamino, carboxyl, $(C_1-C_4)$alkoxycarbonyl, carbamoyl or mono-N- or di-N,N-$(C_1-C_4)$alkylcarbamoyl; phenyl optionally mono- or di-substituted independently with methyl, methoxyl, fluoro, trifluoromethoxyl, carboxyl, $(C_1-C_4)$alkoxycarbonyl, methylthio, methylsulfinyl, methylsulfonyl, $(C_1-C_4)$alkylsulfonylamino or mono-N- or di-N,N-$(C_1-C_4)$alkylaminosulfonyl; or R$^5$ is thiazolyl, isothiazolyl, thienyl, furyl, pyridinyl or any of said heterocycles optionally mono-substituted with carboxyl or mono- or di-substituted with methyl;

T forms a four to seven membered mono- or di-aza, saturated ring, said ring optionally containing thio and said ring optionally mono-substituted on carbon with hydroxyl; and V and V$^1$ are each independently hydrogen, hydroxyl, amino, mono-N- or di-N,N-$(C_1-C_4)$alkylamino, carbamoyl, mono-N- or di-N,N-$(C_1-C_4)$alkylcarbamoyl, carboxyl, $(C_1-C_4)$alkoxy, fluorinated $(C_1-C_4)$alkoxy having from 1 to 9 fluorines, $(C_1-C_4)$alkoxycarbonyl, aminocarbonyl, cyano, thiol, sulfamoyl, $(C_1-C_4)$alkylthio, $(C_1-C_4)$alkylsulfonyl, $(C_1-C_4)$alkylsulfinyl, $(C_1-C_4)$alkylsulfonylamino, fluorinated $(C_1-C_4)$alkylsulfonylamino having from 1 to 9 fluorines, mono-N- or di-N,N-$(C_1-C_4)$ alkylaminosulfonyl, $(C_1-C_4)$alkanoylamino, fluorinated $(C_1-C_4)$alkanoylamino having from 1 to 9 fluorines, ureido, mono-N- or di-N,N-$(C_1-C_4)$alkyl ureido, imidazolyl, pyridyl, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl or $(C_0-C_6)$alkyl said $(C_0-C_6)$ alkyl optionally mono- or di-substituted independently with carboxyl or $(C_1-C_4)$ alkoxycarbonyl.

A preferred group of compounds, designated the A group, contains those compounds having the Formula I as shown above wherein the $C^a$ and $C^i$ substituents are cis and the $C^c$ substituent is trans to the $C^a$ and $C^i$ substituents;

A is phenyl optionally substituted independently with $R^3$, $R^9$ and $R^{10}$;

$R^1$ and $R^2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines or $R^1$ and $R^2$ taken together form an ethylenedioxy ring;

$R^3$, $R^9$ and $R^{10}$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines or $R^3$ and $R^9$ taken together form an $(C_1-C_3)$alkylenedioxy ring;

$R^4$ is $(C_1-C_7)$alkyl;

X is oxy;

Y is oxy;

V is carboxyl or $(C_1-C_4)$alkoxycarbonyl;

$V^1$ is H; and

Z is carboxyl or

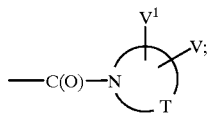

and pharmaceutically acceptable salts thereof.

A group of compounds which is preferred among the A Group of compounds designated the B Group, contains those compounds wherein $R^3$ and $R^9$ are each independently hydrogen, halo, trifluoromethoxy, $(C_1-C_4)$alkoxy or taken together form a $(C_1-C_3)$alkylenedioxy ring;

$R^{10}$ is hydrogen;

$R^2$ is hydrogen;

T forms a piperidin-1-yl ring; and pharmaceutically acceptable salts thereof.

Especially preferred compounds within the B Group of compounds are compounds wherein a. $R^1$ is methyl at the $C^e$ position;
   $R^3$ is 2-methoxy;
   $R^9$ is 3-methoxy;
   $R^4$ is tert-butyl; and
   Z is 4-carboxylpiperidin-1-ylcarbonyl;

b. $R^1$ is methyl at the $C^e$ position;
   $R^3$ is 2-chloro
   $R^9$ is hydrogen;
   $R^4$ is tert-butyl; and
   Z is 3-carboxylpiperidin-1-ylcarbonyl;

c. $R^1$ is methyl at the $C^e$ position;
   $R^3$ is 2-methoxy;
   $R^9$ is hydrogen;
   $R^4$ is tert-butyl; and
   Z is 4-carboxylpiperidin-1-ylcarbonyl;

d. $R^1$ is chloro at the $C^e$ position;
   $R^3$ is 2-methoxy;
   $R^9$ is 3-methoxy;
   $R^4$ is tert-butyl; and
   Z is 4-carboxylpiperidin-1-ylcarbonyl;

e. $R^1$ is chloro at the $C^e$ position;
   $R^3$ is 2-methoxy;
   $R^9$ is hydrogen;
   $R^4$ is tert-butyl; and
   Z is 4-carboxylpiperidin-1-ylcarbonyl;

f. $R^1$ is methyl at the $C^e$ position;
   $R^3$ is 2-methoxy;
   $R^9$ is 3-methoxy;
   $R^4$ is tert-butyl; and
   Z is 3-carboxylpiperidin-1-ylcarbonyl; and pharmaceutically acceptable salts of said compounds.

Preferably Z in the immediately preceding compound is (3R)-3-carboxylpiperidin-1-ylcarbonyl and pharmaceutically acceptable salts thereof.

A preferred group of compounds, designated the C group, contains those compounds having the Formula I as shown above wherein the $C^a$ and $C^i$ substituents are cis and the $C^c$ substituent is trans to the $C^a$ and $C^i$ substituents;

A is phenyl optionally substituted independently with $R^3$, $R^9$ and $R^{10}$;

$R^1$ and $R^2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines or $R^1$ and $R^2$ taken together form an ethylenedioxy ring;

$R^4$ is $(C_1-C_7)$alkyl;

X is oxy;

Y is methylene;

V is carboxyl or $(C_1-C_4)$alkoxycarbonyl;

$V^1$ is H;

Z is carboxyl or

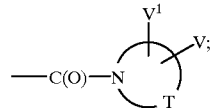

and pharmaceutically acceptable salts thereof.

A group of compounds which is preferred among the C Group of compounds, designated the D Group, contains those compounds wherein $R^3$ and $R^9$ are each independently hydrogen, halo, trifluoromethoxy, $(C_1-C_4)$alkoxy or taken together form a $(C_1-C_3)$alkylenedioxy ring;

$R^{10}$ is hydrogen;

$R^2$ is hydrogen;

T forms a piperidin-1-yl ring; and pharmaceutically acceptable salts thereof.

Especially preferred compounds within the D Group of compounds are compounds wherein a. $R^1$ is methyl at the $C^e$ position;
  $R^3$ is 2-methoxy;
  $R^9$ is 3-methoxy;
  $R^4$ is tert-butyl; and
  Z is 3-carboxylpiperidin-1-ylcarbonyl;
b. $R^1$ is methyl at the $C^e$ position;
  $R^3$ is 2-methoxy;
  $R^9$ is 3-methoxy;
  $R^4$ is tert-butyl; and
  Z is 2-carboxylpiperidin-1-ylcarbonyl;
c. $R^1$ is chloro at the $C^e$ position;
  $R^3$ and $R^9$ are taken together to form 2,3-ethylenedioxyl;
  $R^4$ is tert-butyl; and
  Z is 4-carboxylpiperidin-1-ylcarbonyl;
d. $R^1$ is chloro at the $C^e$ position;
  $R^3$ and $R^9$ are taken together to form 2,3-ethylenedioxyl;
  $R^4$ is tert-butyl; and
  Z is 3-carboxylpiperidin-1-ylcarbonyl;
e. $R^1$ is chloro at the $C^e$ position;
  $R^3$ and $R^9$ are taken together to form 2,3-methylenedioxyl;
  $R^4$ is tert-butyl; and
  Z is 4-carboxylpiperidin-1-ylcarbonyl.
f. $R^1$ is chloro at the $C^e$ position;
  $R^3$ is 2-methoxy;
  $R^9$ is hydrogen;
  $R^4$ is tert-butyl; and
  Z is 4-carboxylpiperidin-1-ylcarbonyl.
g. $R^1$ is chloro at the $C^e$ position;
  $R^3$ is 2-methoxy;
  $R^9$ is hydrogen;
  $R^4$ is tert-butyl; and
  Z is 3-carboxylpiperidin-1-ylcarbonyl;
h. $R^1$ is methyl at the $C^e$ position;
  $R^3$ is 2-methoxy;
  $R^9$ is hydrogen;
  $R^4$ is tert-butyl; and
  Z is 4-carboxylpiperidin-1-ylcarbonyl;
i. $R^1$ is methyl at the $C^e$ position;
  $R^3$ and $R^9$ are taken together to form 2,3-methylenedioxyl;
  $R^4$ is tert-butyl; and
  Z is 3-carboxylpiperidin-1-ylcarbonyl;
j. $R^1$ is chloro at the $C^e$ position;
  $R^3$ is 2-trifluoromethoxy;
  $R^9$ is hydrogen;
  $R^4$ is tert-butyl; and
  Z is 3-carboxylpiperidin-1-ylcarbonyl; and the pharmaceutically acceptable salts of said compounds.

A preferred group of compounds, designated the E group, contains those compounds having the Formula I as shown above wherein
  the $C^a$ and $C^i$ substituents are cis and the $C^c$ substituent is trans to the $C^a$ and $C^i$ substituents;
  A is phenyl optionally substituted independently with $R^3$, $R^9$ and $R^{10}$;
  $R^1$ and $R^2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines or $R^1$ and $R^2$ taken together form an ethylenedioxy ring;
  $R^4$ is $(C_1-C_7)$alkyl;
  X is thio;
  Y is oxy;
  V is carboxyl, $(C_1-C_4)$alkoxycarbonyl or tetrazol-5-yl; and
  $V^1$ is H;
  Z is carboxyl or $$-\text{C(O)}-\text{N}\underset{T}{\overset{V^1}{\diagup}}\text{V};$$

and pharmaceutically acceptable salts thereof.

A group of compounds which is preferred among the E Group of compounds, designated the F Group, contains those compounds wherein
  $R^3$ and $R^9$ are each independently hydrogen, halo, $(C_1-C_4)$alkoxy, trifluoromethoxy, or taken together form a $(C_1-C_3)$alkylenedioxy ring;
  $R^{10}$ is hydrogen;
  $R^2$ is hydrogen;
  T forms a piperidin-1-yl ring; and pharmaceutically acceptable salts thereof.

An especially preferred compound within the E Group of compounds is a compound wherein
  $R_1$ is methyl at the $C^e$ position;
  $R^3$ is 2-methoxy;
  $R^9$ is 3-methoxy;
  $R^4$ is tert-butyl;
  Z is 4-carboxylpiperidin-1-ylcarbonyl; and pharmaceutically acceptable salts thereof.

A preferred group of compounds, designated the G group, contains those compounds having the Formula I as shown above wherein
  the $C^a$ and $C^i$ substituents are cis and the $C^c$ substituent is trans to the $C^a$ and $C^i$ substituents;
  A is phenyl optionally substituted independently with $R^3$, $R^9$ and $R^{10}$;
  $R^1$ and $R^2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines or $R^1$ and $R^2$ taken together form an ethylenedioxy ring;
  $R^3$, $R^9$ and $R^{10}$ are each independently hydrogen, $(C_1-C_4)$ alkoxy, halo, trifluoromethoxy or taken together form a $(C_1-C_3)$alkylenedioxy ring;
  $R^4$ is $(C_1-C_7)$alkyl;
  X is thio;
  Y is methylene;
  V is carboxyl, $(C_1-C_4)$alkoxycarbonyl or tetrazol-5-yl; and
  $V^1$ is H;
  Z is carboxyl or $$-\text{C(O)}-\text{N}\underset{T}{\overset{V^1}{\diagup}}\text{V};$$

and pharmaceutically acceptable salts thereof.

An especially preferred compound within the G Group of compounds is a compound wherein R¹ is chloro at the C^e position;
R² is hydrogen;
R³ is 2-methoxy;
R⁹ is hydrogen;
R¹⁰ is hydrogen
R⁴ is tert-butyl;
Z is 4-carboxylpiperidin-1-ylcarbonyl; and pharmaceutically acceptable salts thereof.

A preferred group of compounds, designated the H group, contains those compounds having the Formula I as shown above wherein Z is

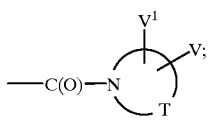

and pharmaceutically acceptable salts thereof.

A group of compounds which is preferred among the H Group of compounds, designated the I Group, contains those compounds wherein
   T forms a piperidin-1-yl ring and pharmaceutically acceptable salts thereof.

A group of compounds which is preferred among the I Group of compounds, designated the J Group, contains those compounds wherein
   the C^a and C^i substituents are cis and the C^c substituent is trans to the C^a and C^i substituents;
   R¹ and R² are each independently hydrogen, halo, (C₁–C₄)alkyl, (C₁–C₄)alkoxy, hydroxy, trifluoromethyl, (C₁–C₄)alkylthio, fluorinated (C₁–C₄) alkoxy having from 1 to 9 fluorines or R¹ and R² taken together form an ethylenedioxy ring;
   R³ and R⁹ are each independently (C₁–C₄)alkoxy or taken together form a (C₁–C₃)alkylenedioxy ring;
   R⁴ is (C₁–C₇)alkyl;
   R¹⁰ is hydrogen; and pharmaceutically acceptable salts thereof.

Preferred compounds of this invention are
1-{[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid;
(3R)-1-{[(6S,8R,10S)-6-tert-butyl-10-(2,3-dimethoxyphenyl)-2-methyl-7-oxo-5,6,7,8-tetrahydro-4H,10H-9-oxa-6a-aza-cyclohepta[de]naphthalen-8-yl]-acetyl}-piperidine-3-carboxylic acid;
(2R)-1-{6S,8R,10S-[6-tert-butyl-10-(2,3-dimethoxyphenyl)-2-methyl-7-oxo-5,6,7,8-tetrahydro-4H,10H-9-oxa-6a-aza-cyclohepta[de]naphthalen-8-yl]-acetyl}-2R-piperidine-2-carboxylic acid;
1-{[(6S,8R,10S)-6-tert-butyl-10-(2,3-dihydro-benzo[1,4]dioxin-5-yl)-2-chloro-7-oxo-5,6,7,8-tetrahydro-4H,10H-9-oxa-6a-aza-cyclohepta[de]naphthalen-8-yl]-acetyl}-piperidine-4-carboxylic acid;
1-{[(6S,8R,10S)-6-tert-butyl-10-(2,3-dihydro-benzo[1,4]dioxin-5-yl)-2-chloro-7-oxo-5,6,7,8-tetrahydro-4H,10H-9-oxa-6a-aza-cyclohepta[de]naphthalen-8-yl]-acetyl}-piperidine-3-carboxylic acid;
(3R)-1-{[(6S,8R,10S)-6-tert-butyl-10-(2,3-dihydro-benzo[1,4]dioxin-5-yl)-2-chloro-7-oxo-5,6,7,8-tetrahydro-4H, 10H-9-oxa-6a-aza-cyclohepta[de]naphthalen-8-yl]-acetyl}-piperidine-3-carboxylic acid;
1-{[(6S,8R,10S)-6-tert-butyl-10-(benzo[1,3]dioxol-4-yl)-2-chloro-7-oxo-5,6,7,8-tetrahydro-4H,10H-9-oxa-6a-aza-cyclohepta[de]naphthalen-8-yl]-acetyl}-piperidine-4-carboxylic acid; and pharmaceutically acceptable salts of said comounds.

Other preferred compounds of this invention are
1-{[(6S,8R,10S)-6-tert-butyl-10-(2-methoxyphenyl)-2-chloro-7-oxo-5,6,7,8-tetrahydro-4H,10H-9-oxa-6a-aza-cyclohepta[de]naphthalen-8-yl]-acetyl}-piperidine-4-carboxylic acid;
1-{[(6S,8R,10S)-6-tert-butyl-10-(2-methoxyphenyl)-2-chloro-7-oxo-5,6,7,8-tetrahydro-4H,10H-9-oxa-6a-aza-cyclohepta[de]naphthalen-8-yl]-acetyl}-piperidine-3-carboxylic acid;
(3R)-1-{[(6S,8R,10S)-6-tert-butyl-10-(2-methoxyphenyl)-2-chloro-7-oxo-5,6,7,8-tetrahydro-4H,10H-9-oxa-6a-aza-cyclohepta[de]naphthalen-8-yl]-acetyl}-piperidine-3-carboxylic acid;
1-{[(6S,8R,10S)-6-tert-butyl-10-(2-trifluoromethoxyphenyl)-2-chloro-7-oxo-5,6,7,8-tetrahydro-4H,10H-9-oxa-6a-aza-cyclohepta[de]naphthalen-8-yl]-acetyl}-piperidine-3-carboxylic acid;
(3R)-1-{[(6S,8R,10S)-6-tert-butyl-10-(2-trifluoromethoxyphenyl)-2-chloro-7-oxo-5,6,7,8-tetrahydro-4H,10H-9-oxa-6a-aza-cyclohepta[de]naphthalen-8-yl]-acetyl}-piperidine-3-carboxylic acid;
1-{[(6S,8R,10S)-6-tert-butyl-10-(benzo[1,3]dioxol-4-yl)-2-methyl-7-oxo-5,6,7,8-tetrahydro-4H,10H-9-oxa-6a-aza-cyclohepta[de]naphthalen-8-yl]-acetyl}-piperidine-3-carboxylic acid;
(3R)-1-{[(6S,8R,10S)-6-tert-butyl-10-(benzo[1,3]dioxol-4-yl)-2-methyl-7-oxo-5,6,7,8-tetrahydro-4H,10H-9-oxa-6a-aza-cyclohepta[de]naphthalen-8-yl]-acetyl}-piperidine-3-carboxylic acid;
(3R)-1-{[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid;
1-{[(1R,7S,9R)-1-tert-butyl-7-(2,3-dimethoxy-phenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid;
1-{[(1R,7S,9R)-1-tert-butyl-7-(2-chlorophenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid;
(3R)-1-{[(1R,7S,9R)-1-tert-butyl-7-(2-chlorophenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid; and pharmaceutically acceptable salts of said compounds.

Yet still other preferred compounds of this invention are
1-{[(1R,7S,9R)-1-tert-butyl-7-(2,3-dimethoxyphenyl)-5-chloro-10-oxo-1,2,9,10-tetrahydro-7H-3,8-dioxa-10a-aza-cyclohepta[de]naphthalen-9-yl]-acetyl}-piperidine-4-carboxylic acid;
1-{[(1R,7S,9R)-1-tert-butyl-7-(2-methoxyphenyl)-5-chloro-10-oxo-1,2,9,10-tetrahydro-7H-3,8-dioxa-10a-aza-cyclohepta[de]naphthalen-9-yl]-acetyl}-piperidine-4-carboxylic acid;
1-{[(1R,7S,9R)-1-tert-butyl-7-(2-methoxyphenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid;
1-{[(1R,7S,9R)-1-tert-butyl-7-(2,3-dimethoxyphenyl)-5-methyl-10-oxo-1,2,9,10-tetrahydro-7H-3-oxa-8-thia- 10a-aza-cyclohepta[de]naphthalen-9-yl]-acetyl}-piperidine-4-carboxylic acid;

1-{[(6S,8R,10S)-6-tert-butyl-10-(2-methoxyphenyl)-2-chloro-7-oxo-5,6,7,8-tetrahydro-4H,10H-9-thia-6a-aza-cyclohepta[de]naphthalen-8-yl]-acetyl}-piperidine-4-carboxylic acid;

1-{[(6S,8R,10S)-6-tert-butyl-10-(2-methoxyphenyl)-2-methyl-7-oxo-5,6,7,8-tetrahydro-4H,10H-9-oxa-6a-aza-cyclohepta[de]naphthalen-8-yl]-acetyl}-piperidine-4-carboxylic acid; and pharmaceutically acceptable salts of said compounds.

Yet another aspect of this invention is directed to methods for treating hypercholesterolemia, hypertriglyceridemia, atherosclerosis, fungal infections, Alzheimer's disease and acne in a mammal (including a human being) by administering to a mammal suffering from hypercholesterolemia, hypertriglyceridemia, atherosclerosis, a fungal infection, Alzheimer's disease or acne, a hypercholesterolemia, hypertriglyceridemia, atherosclerosis, infection, Alzheimer's disease or acne treating amount of a Formula I compound, a prodrug thereof, or a pharmaceutically acceptable salt of said compound or of said prodrug.

Yet another aspect of this invention is directed to a method for treating hypercholesterolemia in a mammal (including a human being) by administering to a mammal suffering from hypercholesterolemia, a hypercholesterolemia treating amount of a Formula I compound, a prodrug thereof, or a pharmaceutically acceptable salt of said compound or of said prodrug.

Yet another aspect of this invention is directed to a method for treating hypertriglyceridemia in a mammal (including a human being) by administering to a mammal suffering from hypertriglyceridemia a hypertriglyceridemia treating amount of a Formula I compound, a prodrug thereof, or a pharmaceutically acceptable salt of said compound or of said prodrug.

Yet another aspect of this invention is directed to a method for treating atherosclerosis in a mammal (including a human being) by administering to a mammal suffering from atherosclerosis an atherosclerotis treating amount of a Formula I compound, a prodrug thereof, or a pharmaceutically acceptable salt of said compound or of said prodrug.

Yet another aspect of this invention is directed to a method for treating a fungal infection in a mammal (including a human being) by administering to a mammal suffering from a fungal infection a infection treating amount of a Formula I compound, a prodrug thereof, or a pharmaceutically acceptable salt of said compound or of said prodrug.

Yet another aspect of this invention is directed to a method for treating Alzheimer's disease in a mammal (including a human being) by administering to a mammal suffering from Alzheimer's disease an Alzheimer's disease treating amount of a Formula I compound, a prodrug thereof, or a pharmaceutically acceptable salt of said compound or of said prodrug.

Yet another aspect of this invention is directed to a method for treating acne in a mammal (including a human being) by administering to a mammal suffering from acne an acne treating amount of a Formula I compound, a prodrug thereof, or a pharmaceutically acceptable salt of said compound or of said prodrug.

This invention is also directed to pharmaceutical compositions which comprise an amount of a compound of Formula I, a prodrug thereof, or a pharmaceutically acceptable salt of said compound or of said prodrug and a pharmaceutically acceptable carrier, vehicle or diluent.

This invention is also directed to pharmaceutical compositions for the treatment of hypercholesterolemia, hypertriglyceridemia, atherosclerosis, fungal infections, Alzheimer's or acne in a mammal (including a human being) which comprise a therapeutically effective amount of a compound of Formula I, a prodrug thereof, or a pharmaceutically acceptable salt of said compound or of said prodrug and a pharmaceutically acceptable carrier, vehicle or diluent.

This invention is also directed to pharmaceutical compositions for the treatment of hypercholesterolemia in a mammal (including a human being) which comprise a hypercholesterolemia treating amount of a compound of Formula I, a prodrug thereof, or a pharmaceutically acceptable salt of said compound or of said prodrug and a pharmaceutically acceptable carrier, vehicle or diluent.

This invention is also directed to pharmaceutical compositions for the treatment of hypertriglyceridemia in a mammal (including a human being) which comprise a hypertriglyceridemia treating amount of a compound of Formula I, a prodrug thereof, or a pharmaceutically acceptable salt of said compound or of said prodrug and a pharmaceutically acceptable carrier, vehicle or diluent.

This invention is also directed to pharmaceutical compositions for the treatment of atherosclerosis in a mammal (including a human being) which comprise an atherosclerosis treating amount of a compound of Formula I, a prodrug thereof, or a pharmaceutically acceptable salt of said compound or of said prodrug and a pharmaceutically acceptable carrier, vehicle or diluent.

This invention is also directed to pharmaceutical compositions for the treatment of a fungal infection in a mammal (including a human being) which comprise a fungal infection treating amount of a compound of Formula I, a prodrug thereof, or a pharmaceutically acceptable salt of said compound or of said prodrug and a pharmaceutically acceptable carrier, vehicle or diluent.

This invention is also directed to pharmaceutical compositions for the treatment of Alzheimer's disease in a mammal (including a human being) which comprise an Alzheimer's disease treating amount of a compound of Formula I, a prodrug thereof, or a pharmaceutically acceptable salt of said compound or of said prodrug and a pharmaceutically acceptable carrier, vehicle or diluent.

This invention is also directed to pharmaceutical compositions for the treatment of acne in a mammal (including a human being) which comprise an acne treating amount of a compound of Formula I, a prodrug thereof, or a pharmaceutically acceptable salt of said compound or of said prodrug and a pharmaceutically acceptable carrier, vehicle or diluent.

Another aspect of this invention is a compound of Formula I, a prodrug thereof, or a pharmaceutically acceptable salt of said compound or of said prodrug or a composition which comprises an amount thereof, for use as a medicament, in particular as an antifungal agent, hypocholesterolemic agent, hypotriglyceridemic agent, anti-atherosclerosis agent, anti-Alzheimer's disease agent or anti-acne agent.

Yet another aspect of this invention is the use of a compound of Formula I, a prodrug thereof, or a pharmaceutically acceptable salt of said compound or of said prodrug or a composition which comprises an amount thereof, for the manufacture of an antifungal agent, hypocholesterolemic agent, hypoglyceridemic agent, anti-atherosclerosis agent, anti-Alzheimer's disease agent or anti-acne agent.

This invention is also directed to pharmaceutical combination composition for the treatment of hypercholesterolemia comprising: a therapeutically effective amount of a composition comprising

- a first compound, said first compound being a compound of Formula I, a prodrug thereof, or a pharmaceutically acceptable salt of said compound or of said prodrug;
- a second compound, said second compound being a cholesterol absorption inhibitor, a cholesterol synthesis inhibitor (other than a compound of Formula I), a fibrate, niacin, an ion-exchange resin, an antioxidant, an ACAT inhibitor or a bile acid sequestrant; and
- a pharmaceutical carrier, vehicle or diluent.

Preferred among the second compounds are an HMG-CoA reductase inhibitor, an HMG-CoA synthase inhibitor, an inhibitor of HMG-CoA reductase gene expression, a squalene epoxidase inhibitor, a squalene cyclase inhibitor, a lanosterol demethylase inhibitor, a fibrate, niacin, an ion-exchange resin, an antioxidant, an ACAT inhibitor or a bile acid sequestrant.

A particularly preferred HMG-CoA reductase inhibitor is lovastatin, simvastatin, pravastatin, fluvastatin, atorvastatin, cerivastatin, nisvastatin or rivastatin.

A particularly preferred lanosterol demethylase inhibitor is fluconazole or voriconazole.

Another aspect of this invention is a method for treating hypercholesterolemia in a mammal comprising administering to a mammal suffering from hypercholesterolemia

- a first compound, said first compound being a compound of Formula I, a prodrug thereof, or a pharmaceutically acceptable salt of said compound or of said prodrug; and
- a second compound, said second compound being a cholesterol absorption inhibitor or a cholesterol synthesis inhibitor (other than a compound of Formula I), a fibrate, niacin, an ion-exchange resin, an antioxidant, an ACAT inhibitor or a bile acid sequestrant
- wherein the amounts of the first and second compounds result in a therapeutic effect.

A preferred aspect of the above method is wherein the second compound is an HMG-CoA reductase inhibitor, an HMG-CoA synthase inhibitor, an inhibitor of HMG-CoA reductase gene expression, a squalene epoxidase inhibitor, a squalene cyclase inhibitor, a lanosterol demethylase inhibitor, a fibrate, niacin, an ion-exchange resin, an antioxidant, an ACAT inhibitor or a bile acid sequestrant.

A particularly preferred aspect of the above method is wherein the HMG-CoA reductase inhibitor is lovastatin, simvastatin, pravastatin, fluvastatin, atorvastatin, cerivastatin, nisvastatin or rivastatin.

Yet another aspect of this invention is a kit containing a treatment for hypercholesterolemia comprising:

a. a first compound, said first compound being a compound of Formula I, a prodrug thereof, or a pharmaceutically acceptable salt of said compound or of said prodrug and a pharmaceutically acceptable carrier, vehicle or diluent in a first unit dosage form;

b. a second compound, said second compound being a cholesterol absorption inhibitor, a cholesterol synthesis inhibitor (other than a compound of Formula I), a fibrate, niacin, an ion-exchange resin, an antioxidant, an ACAT inhibitor or a bile acid sequestrant and a pharmaceutically acceptable carrier, vehicle or diluent in a second unit dosage form; and c. means for containing said first and second dosage forms wherein the amounts of the first and second compounds result in a therapeutic effect.

A preferred second compound is an HMG-CoA reductase inhibitor, an HMG-CoA synthase inhibitor, an inhibitor of HMG-CoA reductase gene expression, a squalene epoxidase inhibitor, a squalene cyclase inhibitor, a lanosterol demethylase inhibitor, a fibrate, niacin, an ion-exchange resin, an antioxidant, an ACAT inhibitor or a bile acid sequestrant.

A particularly preferred HMG-CoA reductase inhibitor is lovastatin, simvastatin, pravastatin, fluvastatin, atorvastatin, cerivastatin, nisvastatin or rivastatin.

This invention is also directed to pharmaceutical combination composition for the treatment of a fungal infection comprising: a therapeutically effective amount of a composition comprising

- a compound of Formula I, a prodrug thereof, or a pharmaceutically acceptable salt of said compound or of said prodrug;
- a lanosterol demethylase inhibitor; and
- a pharmaceutical carrier, vehicle or diluent.

A particularly preferred lanosterol demethylase inhibitor is fluconazole.

Another particularly preferred lanosterol demethylase inhibitor is voriconazole.

Another aspect of this invention is a method for treating a fungal infection in a mammal comprising administering to a mammal suffering from a fungal infection

- a compound of Formula I, a prodrug thereof, or a pharmaceutically acceptable salt of said compound or of said prodrug; and
- a lanosterol demethylase inhibitor
- wherein the amounts of Formula I compound and the lanosterol demethylase inhibitor result in a therapeutic effect.

A particularly preferred aspect of the above method is wherein the lanosterol demethylase inhibitor is fluconazole.

Another particularly preferred aspect of the above method is wherein the lanosterol demethylase inhibitor is voriconazole.

Yet another aspect of this invention is a kit containing a treatment for a fungal infection comprising:

a. a compound of Formula I, a prodrug thereof, or a pharmaceutically acceptable salt of said compound or of said prodrug and a pharmaceutically acceptable carrier, vehicle or diluent in a first unit dosage form;

b. a lanosterol demethylase inhibitor and a pharmaceutically acceptable carrier, vehicle or diluent in a second unit dosage form; and c. means for containing said first and second dosage forms wherein the amounts of the Formula I compound and the lanosterol demethylase inhibitor result in a therapeutic effect.

A particularly preferred aspect of the above kit is wherein the lanosterol demethylase inhibitor is fluconazole.

Another particularly preferred aspect of the above kit is wherein the lanosterol demethylase inhibitor is voriconazole.

This invention is also directed to pharmaceutical combination compositions for the treatment of acne comprising: a therapeutically effective amount of a composition comprising

- a compound of Formula I, a prodrug thereof, or a pharmaceutically acceptable salt of said compound or of said prodrug;
- an antibiotic agent; and
- a pharmaceutical carrier, vehicle or diluent.

Another aspect of this invention is a method for treating acne in a mammal comprising administering to a mammal suffering from acne

- a compound of Formula I, a prodrug thereof, or a pharmaceutically acceptable salt of said compound or of said prodrug; and an antibiotic agent
wherein the amounts of the Formula I compound and the antibiotic agent result in a therapeutic effect.

Yet another aspect of this invention is a kit containing a treatment for acne comprising:
a. a compound of Formula I, a prodrug thereof, or a pharmaceutically acceptable salt of said compound or of said prodrug and a pharmaceutically acceptable carrier, vehicle or diluent in a first unit dosage form;
b. an antibiotic agent and a pharmaceutically acceptable carrier, vehicle or diluent in a second unit dosage form; and
c. means for containing said first and second dosage forms wherein the amounts of the Formula I compound and the antibiotic agent result in a therapeutic effect.

Preferably, for the compounds above, the $C^c$ substituent is beta and the $C^a$ and $C^i$ substituents are alpha. References to the $C^x$ substituent (wherein x is a lower case letter) refer to the carbon position noted in Formula I.

The term "treating", "treat" or "treatment" as used herein includes preventative (e.g., prophylactic), palliative and curative treatment.

By "pharmaceutically acceptable" is meant the carrier, diluent, excipients, and/or salt must be compatible with the other ingredients of the formulation, and not deleterious to the recipient thereof.

Exemplary T rings are piperidin-1-yl, pyrrolidin-1-yl, thiazolidin-3-yl, azetidin-1-yl, tetrahydro-1,4-thiazin-4-yl, tetrahydro-1,4-oxazin-4-yl and tetrahydro-1,3-thiazin-3-yl.

Exemplary het rings are pyrazolyl, imidazolyl, triazolyl, tetrazolyl, piperidinyl, piperazinyl or morpholino.

By halo is meant chloro, bromo, iodo, or fluoro.

By alkyl is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

As used herein the term mono-N- or di-N,N-$(C_1-C_x)$alkyl . . . refers to the $(C_1-C_x)$alkyl moiety taken independently when it is di-N,N-$(C_1-C_x)$alkyl . . . (x refers to integers).

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

By alkylene is meant saturated hydrocarbon (straight chain or branched) wherein a hydrogen atom is removed from each of the terminal carbons. Exemplary of such groups (assuming the designated length encompasses the particular example) are methylene, ethylene, propylene, butylene, pentylene, hexylene, heptylene).

The expression "pharmaceutically-acceptable anionic salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate and 4-toluene-sulfonate.

The expression "pharmaceutically-acceptable cationic salt" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, L-lysine, L-arginine, meglamine (N-methyl-glucamine), benethamine (N-benzylphenethylamine), piperazine or tromethamine (2-amino-2-hydroxymethyl-1,3-propanediol). This is meant to include (R)-α-methylbenzylammonium.

The expression "prodrug" refers to compounds that are drug precursors, which following administration, release the drug in vivo via some chemical or physiological process (e.g., a prodrug on being brought to the physiological pH is converted to the desired drug form). Exemplary prodrugs upon cleavage release the corresponding free acid, and such hydrolyzable ester-forming residues of the Formula I compounds include but are not limited to substituents wherein the Z moiety is independently carboxyl and the free hydrogen is replaced by $(C_1-C_4)$alkyl, $(C_2-C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

As used herein, the expression "reaction-inert solvent" and "inert solvent" refers to a solvent or mixture of solvents which does not interact with starting materials, reagents, intermediates or products in a manner which adversely affects the yield of the desired product.

The term "cis" refers to the orientation of two substituents with reference to each other and the plane of the ring (either both "up" or both "down"). Analogously, the term "trans" refers to the orientation of two substituents with reference to each other and the plane of the ring (the substituents being on opposite faces of the ring).

Alpha and Beta refer to the orientation of a substituent with reference to the plane of the ring (i.e., page). Beta is above the plane of the ring (i.e., page) and Alpha is below the plane of the ring (i.e., page).

The parenthetical negative or positive sign used herein in the nomenclature denotes the direction plane polarized light is rotated by the particular stereoisomer.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates and solvates of the compounds of this invention are also included as an aspect of this invention.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, phosphorous, fluorine and chlorine, such as H, $^2$H, $^3$H, $^{12}$C, $^{13}$C, $^{14}$C, $^{31}$P, $^{32}$P, $^{32}$S, $^{35}$S, $^{18}$F, $^{19}$F, $^{35}$Cl and $^{36}$Cl, respectively. Compounds of the present invention, prodrugs thereof, or pharmaceutically acceptable salts of said compounds or of said prodrugs which contain the aforementioned isotopes and/or other isotopes of other atoms are within the scope of this invention. Certain isotopically-labelled compounds of the present invention, for example, those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^3$H, can afford certain therapeutic advantages resulting from metabolism, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

DTT means dithiothreitol. DMSO means dimethyl sulfoxide. EDTA means ethylenediamine tetraacetic acid.

Other features and advantages will be apparent from the specification and claims which describe the invention.

DETAILED DESCRIPTION OF THE INVENTION

In general the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. Other processes may be described in the Examples.

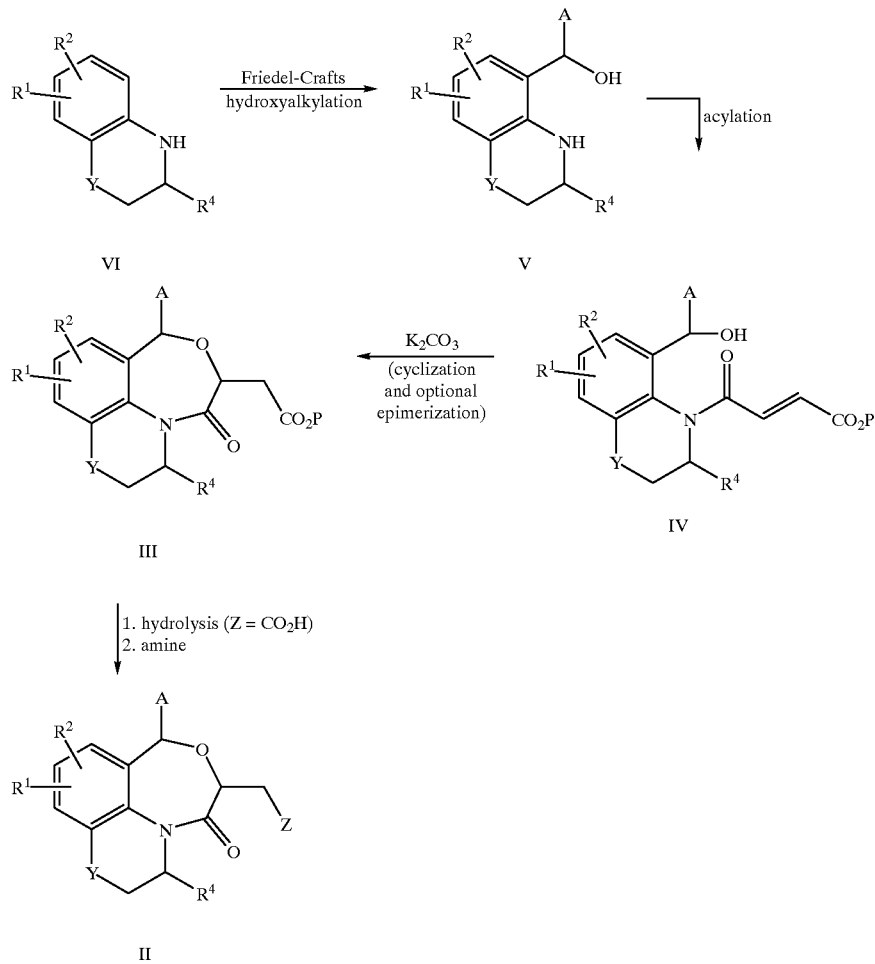

Scheme 2

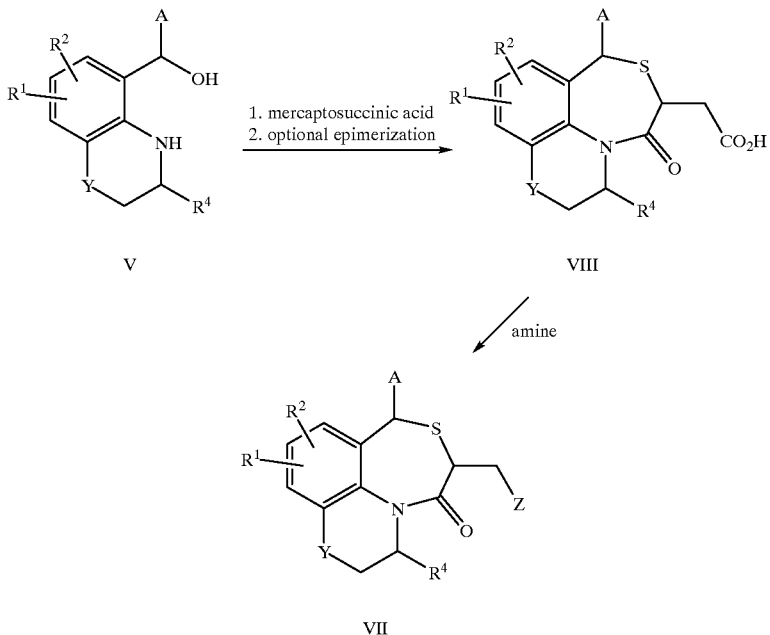

As an initial note, in the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis,* John Wiley & Sons, New York, 1991.

For example, in Reaction Schemes I and II certain Formula I compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the Formula I compound.

As a preliminary note, some substituents (e.g., $R^4$) may best be prepared through conversion of another functional group at a point later in the synthetic sequence to the introduction of the substituent (e.g., $R^4$ in Formulas VI). When to use these conversion methods will vary depending on the nature of the substituent and the compound's stability to the reaction conditions and can be readily determined by one skilled in the art. The method of preparation can also be readily determined by one skilled in the art using conventional methods of organic synthesis.

According to Reaction Scheme I the desired Formula I compounds wherein $R^1$, $R^2$, $R^4$, A and Y are as described above, X is oxy, and Z is a substituted amide (depicted as Formula II compounds) may be prepared by hydrolyzing the corresponding Formula III compound wherein P is a known carboxyl protecting group (see reference below) resulting in the corresponding acid wherein Z is carboxyl. The hydrolysis is followed by acylation of the appropriate amine with the hydrolyzed Formula III compound. Alternatively, the hydrolysis step may be omitted resulting in the desired prodrugs.

Generally, the Formula III compounds, where P is a known carboxyl protecting group, are hydrolyzed in an aqueous alcoholic solvent such as methanol/water with a base such as potassium carbonate at a temperature of about 40° C. to about 80° C., preferably at reflux, for about 2 hours to about 18 hours to provide the Formula II compounds wherein Z is carboxyl. The resulting acid is combined with the appropriate amine in the presence of a carbodiimide (e.g., 1-(3-dimethylaminopropyl)-3-ethylcarbodiimide hydrochloride) in a reaction inert solvent such as methylene chloride at a temperature of about 10° C. to 40° C. for about 2 to about 24 hours.

The desired Formula I compound wherein Z or V is tetrazol-5-yl may be prepared from the corresponding Formula I compound wherein Z or V is carboxyl by converting the carboxyl group to a carboxamide group (Z or V=CONH$_2$), dehydrating the carboxamide to the nitrile (Z or V=CN) and reacting the nitrile with an appropriate azide to form the tetrazole group.

Generally, the acid is converted to the imidazolide by reaction with carbonyl diimidazole in an aprotic solvent such as methylene chloride at a temperature of about 15° C. to about 40° C. for about 30 minutes to about 4 hours, conveniently at room temperature for 1 hour. The resulting imidazolide is converted to the corresponding amide by bubbling ammonia gas into the reaction mixture at a temperature of about 10° C. to about 40° C. for about 3 minutes to about 30 minutes, preferably at room temperature for about 5 minutes or until the reaction is complete by TLC analysis. The amide is converted to the nitrile by treatment with trifluoroacetic anhydride and triethylamine in an inert solvent such as methylene chloride at about 0° C. for about 25 minutes to 2 hours, preferably 30 minutes. Treatment of the nitrile with sodium azide and ammonium chloride in dimethylformamide at a temperature of about 90° C. to about 130° C. for about 7 hours to about 60 hours, preferably at a temperature of 120° C. for 24 hours, yields the desired tetrazole.

The desired Formula I compound wherein Z or V is 4,5-dihydro-5-oxo-1,2,4-oxadiazol-3-yl may be prepared from the corresponding Formula I compound wherein Z or V is CN by converting the nitrile to the amide oxime and reacting the amide oxime with a carbonylating agent to form the corresponding 4,5-dihydro-5-oxo-1,2,4-oxadiazole derivative.

Generally, the nitrile is converted to the amide oxime by reaction with hydroxylamine hydrochloride in the presence of a base such as potassium carbonate in an alcoholic solvent at a temperature of about 60° C. to about 110° C. for about 5 hours to 24 hours, preferably in refluxing ethanol for about 18 hours. The amide oxime is converted to the corresponding 4,5-dihydro-5-oxo-1,2,4-oxadiazole derivative by reaction with carbonyldiimidazole and triethylamine in refluxing ethyl acetate for 24 hours.

Prodrugs of Formula I compounds having a carboxyl group may be prepared by combining the acid with the appropriate alkyl halide in the presence of a base such as potassium carbonate in an inert solvent such as dimethylformamide at a temperature of about 15° C. to about 100° C. for about 1 hour to about 24 hours.

Alternatively, the acid is combined with the appropriate alcohol as solvent in the presence of a catalytic amount of acid such as concentrated sulfuric acid at a temperature of about 20° C. to about 120° C., preferably at reflux, for about 1 hour to about 24 hours.

The desired Formula III compounds wherein $R^1$, $R^2$, $R^4$, A and Y are as described above, X is oxy and P is a known carboxyl protecting group (see reference below) may be prepared from the corresponding Formula IV compound by cyclization, followed by optional epimerization to access other isomers. Generally, the Formula IV compound is combined with a base such as potassium carbonate in an alcoholic solvent such as ethanol at a temperature of about 10° C. to about 40° C., preferably ambient, for about 2 hours to about 72 hours. The extent of epimerization to the various isomers once cyclization has occurred can be monitored by TLC or by removing an aliquot periodically and monitoring by $^1$H NMR. The epimerization can generally be facilitated by warming the alcoholic solvent, preferably to reflux.

The desired Formula IV compounds wherein $R^1$, $R^2$, $R^4$, A and Y are as described above and P is a known carboxyl protecting group (see reference below) may be prepared from the appropriate corresponding Formula V compound by acylation. Generally, the Formula V compound is combined with the appropriate fumaryl chloride protected mono acid, such as fumaryl chloride monoalkyl ester, in a reaction-inert solvent such as methylene chloride at a temperature of about 10° C. to about 50° C., typically ambient, for about 6 to about 18 hours.

The desired Formula V compound wherein $R^1$, $R^2$, $R^4$, A and Y are as described above may be prepared from the appropriate corresponding Formula VI compound by hydroxyalkylation (a modified Friedel-Crafts reaction) to give the set of enantiomers where $R^4$ and A are trans. Optional solvolysis allows access to the set of enantiomers where $R^4$ and A are cis. Generally, the Formula VI compound is combined with a Lewis acid such as boron trichloride in a reaction-inert solvent such as benzene or toluene at a temperature of about ambient to about reflux for about 1 to about 6 hours under a nitrogen atmosphere to form an intermediate complex. The resulting complex is combined with the appropriately substituted benzaldehyde or naphthaldehyde in a reaction-inert solvent such as benzene in the presence of an amine base such as triethylamine at a temperature of about 0° C. to about 40° C., typically ambient, for about 30 minutes to about 18 hours followed by acid cleavage of the boron moiety.

Generally, solvolysis of the Formula V compound can be achieved by stirring in aqueous acid such as aqueous acetic acid at a temperature of ambient to 100° C., preferably ambient, for about 12 to 24 hours.

According to Reaction Scheme II the desired Formula VII compounds wherein $R^1$, $R^2$, $R^4$, A and Y are as described above, X is thio and Z is a substituted amide may be prepared by acylating the appropriate amine with the corresponding Formula VIII compound wherein Z is carboxyl. Generally this reaction may be performed as describe above for the Formula II compounds.

The desired Formula VIII compounds wherein $R^1$, $R^2$, $R^4$, A and Y are as described above and X is thio may be prepared from the appropriate corresponding Formula V compound by a solvolytic displacement reaction with cyclization to the lactam, followed by optional epimerization to access other isomers. Generally, the Formula V compound and mercaptosuccinic acid are combined in an acidic solvent such as acetic acid and heated to about 40° C. to about 100° C., preferably 55° C., for about 12 to 72 hours. The resulting intermediate is then heated, preferably at reflux, in an inert solvent such as chlorobenzene with a catalytic amount of an acid such as p-toluenesulphonic acid with a means to remove water such as a nitrogen sweep across the head space of the reaction vessel or a Soxhlet apparatus containing 3 Å molecular sieves. Generally, epimerization can be carried out in an alcoholic solvent, preferably methanol, in the presence of a base such as potassium carbonate at a temperature of ambient to reflux.

The starting materials and reagents for the above described reaction schemes (e.g., 1,2,3,4-tetrahydroquinolines, 3,4-dihydro-2H-benzo[1,4]oxazines, benzaldehydes and naphthaldehydes, furmaric acid mono-ethyl ester, amino acid esters, prodrug residues, protected forms) are readily available or can be easily synthesized by those skilled in the art using conventional methods of organic synthesis. Some of the preparation methods described herein will require protection of remote functionality (i.e., carboxyl). The need for these protecting groups will vary depending on the nature of the remote functionality and the conditions of the preparation methods. This need is readily determined by one skilled in the art. For a general description of protecting groups (e.g., halo($C_1$–$C_4$)alkyl, ($C_1$–$C_4$)alkoxymethyl, arylmethyl and tri($C_1$–$C_4$)alkylsilyl) and their use, see T. W. Greene, *Protective Groups in Organic Synthesis,* John Wiley & Sons, New York, 1991.

Methods to prepare Formula I compounds other than those described above may be described in the Examples below.

It is reiterated that some substituents (e.g., $R^4$) may best be prepared through conversion of another functional group at a point later in the synthetic sequence to the introduction of the substituents (e.g., $R^4$ in Formulas VI). When to use these conversion methods will vary depending on the nature of the substituent and the compound's stability to the reaction conditions and can be readily determined by one skilled in the art. The method of preparation can also be readily determined by one skilled in the art using conventional methods of organic synthesis.

Alternatively, the compounds of this invention may be prepared by biotransformation as described generally hereinafter and more particularly in the Examples.

Generally, the compounds of this invention may be prepared by contacting the substance to be transformed, and other necessary reactants, with the enzymes derived from a variety of living organisms under conditions suitable for a chemical interaction to occur. Subsequently, the products of the reaction are separated and those of interest are purified for elucidation of their chemical structure and physical and biological properties. The enzymes can be present as purified reagents, be in crude extracts or lysates, or be in intact cells and can be in solution, be in suspension (e.g., intact cells), be covalently attached to a supporting surface, or be imbedded in a permeable matrix (e.g., agarose or alginate beads). The substrate and other necessary reactants (e.g., water, air) are supplied as the chemistry dictates. Generally, the reaction is carried out in the presence of one or more liquid phases, aqueous and/or organic, to promote mass transfer of the reactants and products. The reaction can be conducted aseptically or not. The conditions for monitoring the progress of the reaction and the isolation of the products of the reaction varies according to the physical properties of the reaction system and the chemistry of the reactants and products.

A general exemplary process to prepare the compounds of this invention by biotransformation is described as follows. Nutrient medium (e.g., IOWA Medium: dextrose, yeast extract, dipotassium hydrogen phosphate, sodium chloride, soybean flour, water; adjusted to neutral pH) is added to one or more culture vessels (e.g., fermentation tubes or flasks) which are then steam-sterilized. Each vessel is aseptically inoculated with growth from an agar culture, a suspension of washed cells or spores, or broth from a liquid nutrient medium culture of the biotransforming microorganism. The vessels are mounted on a shaker designed for fermentation and shaken (e.g., 100–300 rpm) at an appropriate temperature (e.g., 20–40° C.) long enough to promote the growth of the microorganism to a suitable population size (e.g., 1–3 days). The substrate to be transformed is dissolved in a suitable water-miscible solvent (e.g., dimethylsulfoxide, dimethylformamide, ethyl alcohol, or methyl alcohol) and sterilized by membrane filtration. To each of the biotransformation vessels, the resulting solution is aseptically added to achieve the desired concentration of substrate (e.g., 100–200 mcg/mL). The dosed vessels are mounted on the shaker and shaken as before, until the substrate has been converted to product[s] by microbial metabolism (e.g., 1–10 days). The contents of the biotransformation vessel are mechanically treated (e.g., by filtration or centrifugation) to separate undissolved solids from the aqueous phase. The aqueous phase is extracted with a suitable water-immiscible organic solvent (e.g., ethyl acetate). The separated solids are extracted with a suitable water-miscible organic solvent (e.g., methanol). The solvent layers from the extraction are recovered, combined, and concentrated to dryness under reduced pressure. The dried crude is redissolved in a solvent that is compatible with the purification method (e.g., acetonitrile, methanol, water, or HPLC method mobile phase). Isolation and purifiction of the biotransformation product(s) are achieved by solid phase extraction (SPE) followed by reversed-phase high performance liquid chromatography (HPLC). The biotransformation product(s) is monitored during chromatographic separation by UV-absorbance and photodiode array spectral profile. Fractions of the HPLC mobile phase containing the product[s] of interest are retained and the product(s) is extracted from the mobile phase with a suitable water-immiscible solvent (e.g., ethyl acetate, chloroform, methylene chloride). The solvent layers from the extraction are recovered, dried over anhydrous sodium sulfate or anhydrous magnesium sulfate, filtered to remove solids, and concentrated under reduced pressure to produce dried purified biotransformation product [s]. The chemical structure of the isolated product[s] is determined from the data derived from mass spectroscopy and $^1$H-NMR.

Standard Method for Biotransformation

Twenty-five mL of nutrient medium (e.g., IOWA Medium: anhydrous dextrose, 20 g; yeast extract, 5 g; dipotassium hydrogen phosphate, 5 g; sodium chloride, 5 g; soybean flour, 5 g; distilled water, 1 L; adjusted to pH 7.2 with 1N sulfuric acid) are added to each of several 125-mL Delong flasks with Morton closures and the resulting combinations are steam-sterilized for 30 minutes at 15 psig and 121° C. Each flask is aseptically inoculated with a loopful of growth from an agar culture, 0.25 mL of a suspension of washed cells or spores, or 0.25 mL of broth from a liquid nutrient medium culture of the biotransforming microorganism. The flasks are mounted vertically on a rotary shaker (1-inch throw) and shaken at 250 rpm and 28° C. for 2 days. The substrate to be biotransformed is dissolved (10 mg/mL) in methanol, dimethylsulfoxide, or other suitable water-miscible solvent. The substrate solution can be used as prepared or it can be sterilized by membrane filtration (0.2 micron porosity). To each of the biotransformation flasks, 0.25 mL of the resulting solution is aseptically added to give an initial substrate concentration of 100 mcg/mL. The dosed flasks are remounted vertically on the rotary shaker and shaken at 250 rpm and 28° C. for one or more days, when another 0.25 mL of the substrate solution is added to each flask to bring the total concentration of substrate added to 200 mcg/mL. The dosed flasks are remounted vertically on the rotary shaker and shaken at 250 rpm and 28° C. for one or more days, i.e., until the substrate has been converted to product[s] by microbial metabolism. The contents of the biotransformation flasks are removed and the undissolved solids are separated from the aqueous phase by filtration or centrifugation and extracted with methanol, or other suitable water-miscible organic solvent. The solvent extract is separated from the residual undissolved solids by filtration or centrifugation and concentrated to dryness under reduced pressure. The aqueous phase is extracted several times with a suitable water-immiscible organic solvent (e.g., ethyl acetate). The solvent layers from the extractions are recovered, combined, and concentrated to dryness under reduced pressure. The dried crude is redissolved in a minimum amount of methanol, or other suitable water-miscible organic solvent that is compatible with the purification method (e.g., acetonitrile), diluted with water to reduce the organic solvent strength to a maximum of 10%, and subjected to solid phase extraction (SPE) of appropriate chemistry to remove as much undesirable material as possible. The SPE eluent fractions containing the biotransformation product[s] of interest is stripped of organic solvent. The desired compound[s] is extracted from the resultant aqueous suspension with ethyl acetate, or other suitable water-immiscible solvent, and taken to dryness under reduced pressure. The biotransformation product[s] is redissolved in a compatible solvent and purified by reversed phase high performance liquid chromatography (HPLC). The biotransformation product[s] is monitored during chromatographic separation by UV-absorbance and spectral profile. Fractions of the HPLC mobile phase containing the product[s] of interest are retained and the product[s] is extracted from the mobile phase with a suitable water-immiscible organic solvent (e.g., ethyl acetate). The solvent layers from the extraction are recovered, filtered to remove solids, and concentrated under reduced pressure to produce dried purified biotransformation product[s]. The chemical structure of the isolated product[s] is determined from the data derived from mass spectroscopy and proton NMR.

The methods described above are useful to prepare the compounds of this invention, other methods may be described in the Examples below.

Some of the Formula I compounds of this invention or intermediates in their synthesis have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by, for example, chiral HPLC methods or converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, an enantiomeric mixture of the Formula I compounds or an intermediate in their synthesis which contain an acidic or basic moiety may be separated into their corresponding pure enantiomers by forming a diastereomeric salt with an optically pure chiral base or acid (e.g., 1-phenyl-ethyl amine or tartaric acid) and separating the diasteromers by fractional crystallization followed by neutralization to break the salt, thus providing the corresponding pure enantiomers. All such isomers, including diastereomers, enantiomers and mixtures thereof are considered as part of this invention. Also, some of the compounds of this invention are atropisomers (e.g., substituted biaryls) and are considered as part of this invention.

More specifically, the Formula I compounds of this invention may be obtained in enantiomerically enriched form by resolving the racemate of the final compound or an intermediate in its synthesis (preferably the final compound) employing chromatography (preferably high pressure liquid chromatography [HPLC]) on an asymmetric resin (preferably Chiralcel™ AD or OD [obtained from Chiral Technologies, Exton, Pa.]).

Some of the Formula I compounds of this invention are acidic and they form a salt with a pharmaceutically acceptable cation. Some of the Formula I compounds of this invention are basic and they form a salt with a pharmaceutically acceptable anion. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds can be obtained in crystalline form by dissolution in an appropriate solvent(s) such as ethanol, hexanes or water/ethanol mixtures.

In addition, when the Formula I compounds of this invention form hydrates or solvates they are also within the scope of the invention.

The utility of the Formula I compounds of the invention, their prodrugs and the salts of such compounds and prodrugs as medical agents in the treatment of the above described disease/conditions in mammals (e.g. humans, male or female) is demonstrated by the activity of the compounds of this invention in conventional assays and the in vivo assay described below. The in vivo assay (with appropriate modifications within the skill in the art) may be used to determine the activity of other lipid or triglyceride controlling agents as well as the compounds of this invention. The combination protocol described below is useful for demonstrating the utility of the combinations of the lipid and triglyceride affecting agents (e.g., the compounds of this invention) described herein. Such assays also provide a means whereby the activities of the Formula I compounds of this invention, their prodrugs and the salts of such compounds and prodrugs (or the other agents described herein) can be compared to each other and with the activities of other known compounds. The results of these comparisons are useful for determining dosage levels in mammals, including humans, for the treatment of such diseases.

The following protocols can of course be varied by those skilled in the art.

The compounds of this invention, their prodrugs and the salts of such compounds and prodrugs, are adapted to therapeutic use as agents that lower plasma LDL cholesterol levels in mammals, particularly humans. Since the concentration of cholesterol in blood is closely related to the development of cardiovascular, cerebral vascular or peripheral vascular disorders, these compounds, by virtue of their hypocholesterolemic action, prevent, arrest and/or regress atherosclerosis.

The hypocholesterolemia activity of these compounds can be determined by assessing the effect of these compounds on the action of squalene synthetase by measuring the overall conversion of [$1-^3$H]farnesyl pyrophosphate ([$^3$H]FPP) to [$^3$H]squalene, essentially as previously described in Meth. Enzymol. 110, 359, 1985 using the anaerobic atmosphere generating oxygen consumption system described in Analyt. Biochem. 203, 310, 1992, in comparison to known controls (e.g., zaragozic acid A).

Briefly, to a 3 $\mu$l volume of either DMSO (control) or DMSO containing compound, are added 47 $\mu$l of Squalene Synthetase Cofactor/Substrate solution (SQS Cofactor/Substrate solution contains 50 mM K$_x$PO$_4$ (pH 7.4), 5.0 mM MgCl$_2$, 411 $\mu$M NADP$^+$, 3.4 mM glucose-6-phosphate, 20 U/ml glucose-6-phosphate dehydrogenase, 15 mM NaF, 78.1 mM sodium ascorbate, 31.3 U/ml ascorbate oxidase, and 1.56 times the indicated final concentrations of [$^3$H]FPP (sp. act. 380/pmol)) and 25 $\mu$l of PMED buffer (PMEB buffer contains 50 mM K$_x$PO$_4$ (pH 7.4), 5 mM MgCl$_2$, 1.0 mM EDTA, 5.0 mM dithiothreitol) containing 1 mg/ml microsomal protein [Final assay concentrations: 48 mM K$_x$PO$_4$ (pH 7.4), 4.8 mM MgCl$_2$, 0.33 mM EDTA, 1.67 mM DTT, 258 $\mu$M NADP$^+$, 2.1 mM glucose-6-phosphate, 0.95U glucose-6-phosphate dehydrogenase, 9.5 mM NaF, 50 mM sodium ascorbate, 1.5U ascorbate oxidase, 4% DMSO, and 5.1 $\mu$M [$^3$H]farnesyl pyrophosphate]. After incubation at 37° C. for 30 min, enzymatic reactions are terminated by sequential addition of 40 $\mu$l, 10 M NaOH, 40 $\mu$l EtOH, 10 $\mu$l of 2 mg/ml squalene in chloroform. After saponification (90 minutes, 37° C.), aliquots were applied to silica gel TLC and newly formed squalene separated from unreacted substrate by chromatography in toluene-ethyl acetate (9:1). The squalene band is visualized with iodine vapors, removed, and immersed in Aqualsol-2 liquid scintillation fluid. Squalene synthetase activity is expressed as pmoles of squalene formed from farnesyl pyrophosphate per min of incubation at 37° C. per mg microsomal protein, based on the stoichiometry of the reaction whereby two moles of [$^3$H]farnesyl pyrophosphate react to form one mole of [$^3$H]squalene and half of the radiolabel is lost from the C-1 position of the prenylating [$^3$H]farnesyl pyrophosphate due to 1-pro-S hydrogen release. Rat hepatic microsomes are used as the source of squalene synthetase activity as described by Harwood et al (J. Lipid Res. 34, 377, 1993). Briefly, hepatic tissues are rinsed in phosphate buffered saline and immediately homogenized at 4° C. in PMED buffer, using a Dounce tissue homogenizer. Homogenates are centrifuged at 10,000×g for 20 min at 4° C. and the resultant supernatants are centrifuged at 178,000×g for 90 min at 4° C. Microsomal pellets are resuspended in PMED buffer by a Potter-Elvehjem pestle and stored frozen in liquid $N_2$ until use. For such preparations, there is no notable loss in enzyme activity within 3 months.

The hypercholesterolemia treating activity of these compounds may be demonstrated by methods based on standard procedures. For example, the in vivo activity of these compounds in inhibiting cholesterol biosynthesis may be determined by the procedure of Hughes et. al. 1977 J. Biol Chem. 252: 548.

Activity of these compounds can be determined by the amount of hypocholesterolemic agent that reduces hepatic cholesterol biosynthesis, relative to control, in male CD1 mice. Male CD1 mice are maintained on a cholesterol-free diet in a 12 hr light/12 hr dark cycle. At mid light cycle animals are administered a 0.5 mL oral bolus of saline containing 0.25% methyl cellulose, 0.6% Tween 80 and 10% ethanol (control animals) or an oral bolus that contained in addition the desired concentration of compound to be tested. One hour following bolus administration the animals receive an intraperitoneal injection (0.15 ml) of [$^{14}$C]-mevalonolactone dissolved in water (0.5 uCi/animal). One hour following the injection of radioactivity the animals are sacrificed, livers excised, saponified ((2.5 M KOH, 2 h) 60° C.) and extracted with petroleum ether and ethanol. After saponification, the radioactivity is measured. Total hepatic radioactivity is calculated based on measured liver weights. The degree of cholesterol biosynthesis inhibition is expressed as a percentage of the total radioactivity in treated vs control animals. The above assay carried out with a range of doses of test compounds allows the determination of an $ED_{50}$ value for the in vivo reduction of hepatic cholesterol biosynthesis.

The hypercholesterolemia and hypertriglyceremia treating activity of these compounds may also be demonstrated by determining the amount of compound required to reduce cholesterol levels and/or triglycerides. For example LDL cholesterol levels may be measured in the plasma of certain mammals, for example marmosets that possess a plasma lipoprotein profile similar to that of humans (Crook et al. Arteriosclerosis 10, 625, 1990). Cholesterol synthesis inhibitors, for example HMG-CoA reductase inhibitors and the squalene synthetase inhibitor zaragozic acid A, lower plasma cholesterol concentrations in this species (Baxter, et al., J. Biol. Chem. 267, 11705, 1992). Adult marmosets are assigned to treatment groups so that each group has a similar mean ±SD for total plasma cholesterol concentration. After group assignment, marmosets are dosed daily with compound as a dietary admix or by intragastric intubation for from one to eight weeks. Control marmosets receive only the dosing vehicle. Plasma total, LDL and HDL cholesterol values can be determined at any point during the study by obtaining blood from an antecubital vein and by separating plasma lipoproteins into their individual subclasses by density gradient centrifugation, and by measuring cholesterol concentration as previously described (Crook, et al., Arteriosclerosis 10, 625, 1990). An analogous measurement of triglycerides may be made to determine the effect on hypertriglyceremia using, for example, an enzymatic assay kit (Wako Pure Chemical Industries).

Anti-atherosclerosis effects of the compounds can be determined by the amount of agent required to reduce the lipid deposition in the rabbit aorta. Male New Zealand White rabbits are fed a diet containing 0.4% cholesterol and 5% peanut oil for 4 days (meal-fed once per day). Rabbits are bled from the marginal ear vein and total plasma cholesterol values are determined from these samples. The rabbits are then assigned to treatment groups so that each group has a similar mean ±s.d. for total plasma cholesterol concentration. After group assignment, rabbits are dosed daily with compound given as a dietary admix or on a small piece of gelatin based confection. Control rabbits receive only the dosing vehicle be it the food or the gelatin confection. The cholesterol/peanut oil diet is continued along with the compound administration throughout the study. Plasma cholesterol values can be determined at any point during the study by obtaining blood from the marginal ear vein. After 5 months, the rabbits are sacrificed and the aortae are removed from the thoracic arch to the branch of the iliac arteries. The aortae are cleaned of adventitia, opened longitudinally and then stained with Sudan IV as described by Holman et al. (Lab. Invest. 1958, 7, 42–47). The percent of the surface area stained is quantitated by densitometry using an Optimas Image Analyzing System (Image Processing Systems). Reduced lipid deposition is indicated by a reduction in the percent surface area stained in the drug group in comparison with the control rabbits.

Administration of the compounds of this invention can be via any method which delivers a compound of this invention systemically and/or locally. These methods include oral routes, parenteral, intraduodenal routes, etc. Generally, the compounds of this invention are administered orally, but parenteral administration (e.g., intravenous, intramuscular, subcutaneous or intramedullary) may be utilized, for example, where oral administration is inappropriate for the target or where the patient is unable to ingest the drug.

Thus, for example, in one mode of administration a compound of this invention may be administered once at night prior to sleep. Alternatively a compound may be administered twice or three times daily with or without meals. In any event, the amount and timing of compound administered will, of course, be dependent on the subject being treated, on the severity of the affliction, on the manner of administration and on the judgment of the prescribing physician. Thus, because of patient to patient variability, the dosages given below are a guideline and the physician may titrate doses of the compound to achieve the plasma cholesterol lowering that he/she considers appropriate for the patient. In considering the degree of hypocholesterolemic activity desired, the physician must balance a variety of factors such as starting cholesterol level, other cardiovascular risk factors, presence of preexisting disease, and age of the patient and his/her motivation. Those skilled in the art will know of the National Cholesterol Education program guidelines for treatment of hypercholesterolemia (Circulation 1991; 83:2154).

In general an effective dosage for the Formula I compounds of this invention, their prodrugs and the salts of such compounds and prodrugs described above for the treatment of hypercholesterolemia, hypertriglyceridemia or atherosclerosis is in the range of 0.0005 to 50 mg/kg/day, preferably 0.001 to 25 mg/kg/day, most preferably 0.005 to 5 mg/kg/day. For an average 70 kg human, this would amount to 0.000035 to 3.5 g/day, preferably 0.00007 to 1.75 g/day, most preferably 0.00035 to 0.35 g/day.

The compounds of this invention are also effective as antifungal agents, useful in the curative or prophylactic treatment of fungal infections in animals such as mammals, including humans. For example, they are useful in treating superficial fungal infections in man caused by, among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, species of Candida (e.g. *Candida albicans*), *Cryptococcus neoformans, Aspergillus flavus, Aspergillus fumigatus,* Coccidioides, Paracoccidioides, Histoplasma or Blastomyces.

The in vitro evaluation of the antifungal activity of the compounds of this invention can be performed by determining the minimum inhibitory concentration (MIC), which is the concentration of the test compounds, in a suitable medium, at which growth of the particular micro-organism fails to occur. In practice, a series of agar plates, or liquid medium in microtiter plates, each having the test compound incorporated at a particular concentration, is inoculated with a standard culture of, for example, *Cryptococcus neoformans,* and each plate is then incubated for 48 hours at 37° C. The plates are then examined for the presence or absence of growth of the fungus and the appropriate MIC value is noted. Other micro-organisms used in such tests can include *Candida albicans, Aspergillus fumigatus,* Trichophyton spp., Microsporum spp., *Epidermophyton floccosum, Coccidioides immitis* and *Torulopsis glabrata.*

The in vivo evaluation of the compounds as antifungal agents can be carried out at a series of dose levels by intraperitoneal or intravenous injection, or by oral administration, to mice or rats which are inoculated with, e.g. a strain of *Candida albicans, Aspergillus fumigatus* or *Cryptococcus neoformans.* Activity may be based on the number of survivors from a treated group of mice after the death of an untreated group of mice.

For *Candida spp.* infection models the dose level at which the compounds provides 50% protection against the lethal effect of the infection ($PD_{50}$) is also assessed.

For *Aspergillus spp.* infection models the number of mice cured of the infection after a set dose allows further assessment of activity.

For *Cryptococcus spp.* infection models the number of colony forming units existing after a set dose is assessed and compared with control to determine compound efficacy. A preliminary assessment of potential liver toxicity may also be made on the basis of increase in liver weight relative to control.

As an antifungal treatment the compounds of this invention are administered to mammals (e.g., humans) by conventional methods.

For human antifungal use, the compounds of this invention can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavoring or coloring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral antifungal administration to human patients, the daily dosage level of the Formula I compounds of this invention, their prodrugs and the salts of such compounds and prodrugs for antifungal treatments will be from 0.01 to 20 mg/kg, preferably 0.5 to 5 mg/kg, (in single or divided doses) when administered by either the oral or parenteral route. Thus, tablets or capsules of the compounds will contain from 5 mg to 0.5 g of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of this invention can be administered in the form of a suppository pessary, or they may be applied topically in the form of a lotion, solution, cream, ointment or dusting powder. For example, they can be incorporated into a cream consisting an aqueous emulsion of polyethylene glycols or liquid paraffin; or they can be incorporated, at a concentration between 1 to 10%, into an ointment comprising a white wax or white soft paraffin base together with such stabilizers and preservatives as may be required.

Since the compounds of this invention are cholesterol biosynthesis inhibitors they can also lower the levels of Apolipoprotein E isoform 4 circulating in the bloodstream. Apolipoprotein E isoform 4 that is made in the brain also circulates through the central nervous system and is present in the cerebrospinal fluid. Compounds of this invention are useful for the treatment of Alzheimer's disease.

Apolipoprotein E isoform 4 ("ApoE isoform 4") is an apolipoprotein which is the gene product of the apolipoprotein E Type 4 allele and is carried in the bloodstream on lipoproteins including LDL. Possession of one or two copies of the apolipoprotein E type 4 allele has been linked to a greatly increased risk of developing Alzheimer's disease. In the liver, low density lipoprotein receptors (LDL receptors) are responsible for absorbing and taking up from the bloodstream various lipoproteins including some of those containing ApoE isoform 4. LDL receptors are regulated by gene repressors derived from cholesterol that suppress the transcription of the LDL-receptor. Inhibition of cholesterol biosynthesis reduces the presence of these cholesterol-derived LDL gene repressors. This relieves the suppression of the production of the LDL receptor, leading to production of additional LDL receptors in the liver, which in turn, remove additional amounts of lipoproteins including ApoE Type 4 containing lipoproteins from the bloodstream. The Alzheimer's disease treating activity of these compounds can be determined by assessing the effect of these compounds on the action of squalene synthetase by measuring the overall conversion of [$1-^3$H]farnesyl pyrophosphate to [$^3$H]squalene, essentially as previously described in Meth. Enzymol. 110, 359, 1985 using the anaerobic atmosphere generating oxygen consumption system described in Analyt. Biochem. 203, 310, 1992, in comparison to known controls (e.g., zaragozic acid A). This assay is described more fully above.

The Alzheimer's disease treating activity of these compounds may also be demonstrated by determining the amount of compound required to reduce cholesterol levels, for example LDL cholesterol levels, in the plasma of certain mammals, for example marmosets that possess a plasma lipoprotein profile similar to that of humans (Crook et al. Arteriosclerosis 10, 625, 1990). Cholesterol synthesis inhibitors, for example HMG-CoA reductase inhibitors and the squalene synthetase inhibitor zaragozic acid A, lower plasma cholesterol concentrations in this species (Baxter, et al., J. Biol. Chem. 267, 11705, 1992). This assay is described more fully above.

The compounds of this invention may be administered using conventional methods for the treatment of Alzheimer's disease. In general an effective dosage for the Formula I compounds of this invention, their prodrugs and the salts of such compounds and prodrugs for the treatment of Alzheimer's disease is in the range for adults of from about 1 mg to 1000 mg (preferably 5 to 100 mg,) per day which may be given in a single dose or in two to four divided doses. Higher doses may be favorably employed as required.

Since the compounds of this invention are squalene synthesis inhibitors they are effective for the treatment of acne vulgaris. Squalene is a major component of sebum, comprising about 12% of sebum in adults. The severity of acne vulgaris correlates directly with the sebum secretion rate and several compounds which decrease sebum secretion rate have been shown to improve acne. By inhibiting squalene, the compounds of this invention can decrease the sebum secretion rate and thereby treat acne.

The concentration of squalene in sebum increases fourfold after puberty and it is believed that this increase in squalene concentration alone or in concert with other changes in sebum composition or sebum secretion rate facilitate the development of acne. The compounds of this invention are useful in preventing or mollifying acne by reducing the percentage and total amount of squalene in sebum.

In addition to reducing squalene levels in sebum, by limiting the production of epoxides, the sebum may become less inflammatory (through metabolic action of the ever-present P. acnes). The compounds of this invention therefore provide a dual effect to combat acne and thus constitute a new, better treatment for acne than current keratolytic and anti-androgen therapies.

The anti-acne activity of the compounds of this invention may be demonstrated by testing the in vitro effects of the compounds in human sebaceous gland culture using conditions analogous to those described in FEBS Letters 200(1), 173–176 (1986) and J. Cell Science 95, 125–136 (1990). Thus, the human sebaceous gland culture may be incubated with the test compound and subsequent sebum production and qualitative changes of sebum composition measured over a short period of time and compared with controls and other actives.

For the treatment of acne the compounds of this invention may be administered by conventional methods. For the treatment of acne each dosage unit will preferably contain 0.001 mg to 1000 mg, advantageously 0.01 mg to 400 mg, of a Formula I compound of this invention, a prodrug thereof or a salt of such compound or prodrug. The daily dosage as employed for human treatment will preferably range from 0.001 mg to 5000 mg of active ingredient, most preferably from 0.01 mg to 2000 mg which may be administered in 1 to 4 daily doses, for example, depending on the route of administration and on the condition of the patient.

The compounds of this invention may also be used in conjunction with other pharmaceutical agents (e.g., LDL-cholesterol lowering agents, triglyceride lowering agents) for the treatment of the disease/conditions described herein. For example, they may be used in combination with cholesterol synthesis inhibitors, cholesterol absorption inhibitors, MTP/Apo B secretion inhibitors, and other cholesterol lowering agents such as fibrates, niacin, ion-exchange resins, antioxidants, ACAT inhibitors and bile acid sequestrants. Alternatively, a compound of this invention may be used in conjunction with an antifungal agent such as those conventional in the art (e.g., lanosterol demethylase inhibitor) for the treatment of a fungal infection. Alternatively, they may be used in conjunction with another anti-acne agent (e.g., a topical or oral antibiotic both of which are conventional in the pharmaceutical industry). In combination therapy treatment, both the compounds of this invention and the other drug therapies are administered to mammals (e.g., humans) by conventional methods.

Any HMG-CoA reductase inhibitor may be used as the second compound in the combination aspect of this invention. The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol. 1981; 71:455–509 and references cited therein). A variety of these compounds are described and referenced below however other HMG-CoA reductase inhibitors will be known to those skilled in the art. U.S. Pat. No. 4,231,938 (the disclosure of which is hereby incorporated by reference) discloses certain compounds isolated after cultivation of a microorganism belonging to the genus Aspergillus, such as lovastatin. Also, U.S. Pat. No. 4,444,784 (the disclosure of which is hereby incorporated by reference) discloses synthetic derivatives of the aforementioned compounds, such as simvastatin. Also, U.S. Pat. No. 4,739,073 (the disclosure of which is incorporated by reference) discloses certain substituted indoles, such as fluvastatin. Also, U.S. Pat. No. 4,346,227 (the disclosure of which is incorporated by reference) discloses ML-236B derivatives, such as pravastatin. Also, EP-491226A (the disclosure of which is incorporated by reference) discloses certain pyridyidihydroxyheptenoic acids, such as rivastatin. In addition, U.S. Pat. No. 5,273,995 (the disclosure of which is incorporated by reference) discloses certain 6-[2-(substituted-pyrrol-1-yl)alkyl]pyran-2-ones such as atorvastatin.

Any MTP/Apo B secretion (microsomal triglyceride transfer protein and/or apolipoprotein B) inhibitor may be used as the second compound in the combination aspect of this invention. The term MTP/Apo B secretion inhibitor refers to a compound which inhibits the secretion of triglycerides, cholesteryl ester, and phospholipids. Such inhibition is readily determined by those skilled in the art according to standard assays (e.g., Wetterau, J. R. 1992; Science 258:999). A variety of these compounds are described and referenced below however other MTP/Apo B secretion inhibitors will be known to those skilled in the art. WO 96/40640 and WO 98/23593 are two exemplary publications. For example, the following MTP/Apo B secretion inhibitors are particularly useful:

4'-trifluoromethyl-biphenyl-2-carboxylic acid [2-(1H-[1,2,4,]triazol-3-ylmethyl)-1,2,3,4-tetrahydro-isoquinolin-6-yl]-amide;

4'-trifluoromethyl-biphenyl-2-carboxylic acid [2-(2-acetylamino-ethyl)-1,2,3,4-tetrahydro-isoquinolin-6-yl]-amide;

(2-{6-[(4'-trifluoromethyl-biphenyl-2-carbonyl)-amino]-3,4-dihydro-1H-isoquinolin-2-yl}-ethyl)-carbamic acid methyl ester;

4'-trifluoromethyl-biphenyl-2-carboxylic acid [2-(1H-imidazol-2-ylmethyl)-1,2,3,4-tetrahydro-isoquinolin-6-yl]-amide;

4'-trifluoromethyl-biphenyl-2-carboxylic acid [2-(2,2-diphenyl-ethyl)-1,2,3,4-tetrahydro-isoquinolin-6-yl]-amide; and 4'-trifluoromethyl-biphenyl-2-carboxylic acid [2-(2-ethoxy-ethyl)-1,2,3,4-tetrahydro-isoquinolin-6-yl]-amide.

Any HMG-CoA synthase inhibitor may be used as the second compound in the combination aspect of this invention. The term HMG-CoA synthase inhibitor refers to a compound which inhibits the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (Meth Enzymol. 1975; 35:155–160: Meth. Enzymol. 1985; 110:19–26 and references cited therein). A variety of these compounds are described and referenced below, however other HMG-CoA synthase inhibitors will be known to those skilled in the art. U.S. Pat. No. 5,120,729 (the disclosure of which is hereby incorporated by reference) discloses certain beta-lactam derivatives. U.S. Pat. No. 5,064,856 (the disclosure of which is hereby incorporated by reference) discloses certain spiro-lactone derivatives prepared by culturing a microorganism (MF5253). U.S. Pat. No. 4,847,271 (the disclosure of which is hereby incorporated by reference) discloses certain oxetane compounds such as 11-(3-hydroxymethyl-4-oxo-2-oxetayl)-3,5,7-trimethyl-2,4-undeca-dienoic acid derivatives.

Any compound that decreases HMG-CoA reductase gene expression may be used as the second compound in the combination aspect of this invention. These agents may be HMG-CoA reductase transcription inhibitors that block the transcription of DNA or translation inhibitors that prevent translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such regulation is readily determined by those skilled in the art according to standard assays (Meth. Enzymol. 1985; 110:9– 19). Several compounds are described and referenced below, however other inhibitors of HMG-CoA reductase gene expression will be known to those skilled in the art. U.S. Pat. No. 5,041,432 (the disclosure of which is incorporated by reference) discloses certain 15-substituted lanosterol derivatives. Other oxygenated sterols that suppress synthesis of HMG-CoA reductase are discussed by E. I. Mercer (Prog.Lip. Res. 1993;32:357–416).

Any squalene epoxidase inhibitor may be used as the second compound in the combination aspect of this invention. The term squalene epoxidase inhibitor refers to a compound which inhibits the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta 1984; 794:466–471). A variety of these compounds are described and referenced below, however other squalene epoxidase inhibitors will be known to those skilled in the art. U.S. Pat. Nos. 5,011,859 and 5,064,864 (the disclosures of which are incorporated by reference) disclose certain fluoro analogs of squalene. EP publication 395,768 A (the disclosure of which is incorporated by reference) discloses certain substituted allylamine derivatives. PCT publication WO 9312069 A (the disclosure of which is hereby incorporated by reference) discloses certain amino alcohol derivatives. U.S. Pat. No. 5,051,534 (the disclosure of which is hereby incorporated by reference) discloses certain cyclopropyloxy-squalene derivatives.

Any squalene cyclase inhibitor may be used as the second component in the combination aspect of this invention. The term squalene cyclase inhibitor refers to a compound which inhibits the bioconversion of squalene-2,3-epoxide to lanosterol, catalyzed by the enzyme squalene cyclase. Such inhibition is readily determined by those skilled in the art according to standard assays (FEBS Lett. 1989;244:347–350.). In addition, the compounds described and referenced below are squalene cyclase inhibitors, however other squalene cyclase inhibitors will also be known to those skilled in the art. PCT publication WO9410150 (the disclosure of which is hereby incorporated by reference) discloses certain 1,2,3,5,6,7,8,8α-octahydro-5,5,8α(beta)-trimethyl-6-isoquinolineamine derivatives, such as N-trifluoroacetyl-1,2,3,5,6,7,8,8α-octahydro-2-allyl-5,5,8α(beta)-trimethyl-6(beta)-isoquinolineamine. French patent publication 2697250 (the disclosure of which is hereby incorporated by reference) discloses certain beta, beta-dimethyl- 4-piperidine ethanol derivatives such as 1-(1,5,9-trimethyldecyl)-beta,beta-dimethyl-4-piperidineethanol.

Any combined squalene epoxidase/squalene cyclase inhibitor may be used as the second component in the combination aspect of this invention. The term combined squalene epoxidase/squalene cyclase inhibitor refers to a compound that inhibits the bioconversion of squalene to lanosterol via a squalene-2,3-epoxide intermediate. In some assays it is not possible to distinguish between squalene epoxidase inhibitors and squalene cyclase inhibitors, however, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below, however other squalene epoxidase/squalene cyclase inhibitors will be known to those skilled in the art. U.S. Pat. Nos. 5,084,461 and 5,278,171 (the disclosures of which are incorporated by reference) disclose certain azadecalin derivatives. EP publication 468,434 (the disclosure of which is incorporated by reference) discloses certain piperidyl ether and thio-ether derivatives such as 2-(1-piperidyl) pentyl isopentyl sulfoxide and 2-(1-piperidyl)ethyl ethyl sulfide. PCT publication WO 9401404 (the disclosure of which is hereby incorporated by reference) discloses certain acyl-piperidines such as 1-(1-oxopentyl-5-phenylthio)-4-(2-hydroxy-1-methyl)-ethyl)piperidine. U.S. Pat. No. 5,102,915 (the disclosure of which is hereby incorporated by reference) discloses certain cyclopropyloxy-squalene derivatives.

Any lanosterol demethylase inhibitor may be used as the second compound in the combination aspect of this invention. The term lanosterol demethylase inhibitor refers to a compound which inhibits the 14-demethylation of lanosterol catalyzed by the enzyme lanosterol demethylase. Such inhibition is readily determined by those skilled in the art according to standard assays (Biochemistry 1994; 33:4702–4713 and references cited therein). A variety of these compounds are described and referenced below however other lanosterol demethylase inhibitors will be known to those skilled in the art. Fluconazole is exemplified in U.S. Pat. No. 4,404,216 (the disclosure of which is hereby incorporated by reference). Voriconazole is exemplified in U.S. Pat. No. 5,278,175 (the disclosure of which is hereby incorporated by reference) and is (2R,3S)-2-(2,4-difluorophenyl)-3-(5-fluoropyrimidin-4-yl)-1-(1,2,4-triazol-1-yl)butan- 2-ol. U.S. Pat. Nos. 4,782,059 and 4,894,375 (the disclosures of which are hereby incorporated by reference) disclose certain azoles such as cis-1-acetyl 4-(4-((2-(2,4-dichlorophenyl)-2-(1H-imidazol-1-ylmethyl)1,3-dioxolan-4-yl)methoxy)phenyl) piperazine (ketoconazole). EP publication 492474A (the disclosure of which is hereby incorporated by reference) discloses certain dioxolanes such as (2S,4S)-cis-2-(2-(4-chlorophenyl)ethyl)-2-imidazol-1-yl) methyl-4-(4-aminophenyl-thio)methyl-1,3-dioxolane. U.S. Pat. No. 5,041,432 (the disclosure of which is hereby incorporated by reference) discloses certain 15-substituted lanosterol derivatives.

A dosage of the combination pharmaceutical agent to be used in conduction with the squalene synthesis inhibitor used that is effective for the indication being treated.

For example, typically an effective dosage for HMG-CoA reductase inhibitors is in the range of 0.01 to 100 mg/kg/day. In general an effective dosage for the MTP/Apo B secretion inhibitors is in the range of 0.01 to 100 mg/kg/day.

The compounds of the present invention are generally administered in the form of a pharmaceutical composition comprising at least one of the compounds of this invention together with a pharmaceutically acceptable vehicle, diluent or carrier. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. A preferred formulation is a solution or suspension in an oil, for example olive oil, Miglyol™ or Capmul™, in a soft gelatin capsule. Antioxidants may be added to prevent long term degradation as appropriate. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences,* Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the disease/condition of the subject being treated, e.g., atherosclerosis.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I, a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . ." etc. Other variations of memory aids will be readily apparent. A "daily dose" can be a single tablet or capsule or several pills or capsules to be taken on a given day. Also, a daily dose of a Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of this invention either alone or in combination with each other or other compounds generally will be administered in a convenient formulation. The following formulation examples only are illustrative and are not intended to limit the scope of the present invention.

In the formulations which follow, "active ingredient" means a compound of this invention.

Formulation 1: Gelatin Capsules
Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:
Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredient are made up as follows:

Formulation 3: Tablets

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient dissolved in ethanol 1% | 20 mg |
| Intralipid ™ emulsion | 1,000 mL |

The solution of the above ingredients is intravenously administered to a patient at a rate of about 1 mL per minute. Soft gelatin capsules are prepared using the following:

Formulation 8: Soft Gelatin Capsule with Oil Formulation

| Ingredient | Quantity (mg/capsule) |
| --- | --- |
| Active ingredient | 10–500 |
| Olive Oil or Miglyol ™ Oil | 500–1000 |

The active ingredient above may also be a combination of agents.

General Experimental Procedures

In the Examples below proton nuclear magnetic resonance spectra ($^1$H NMR) and nuclear magnetic resonance spectra ($C^{13}$ NMR) were measured for solutions in deuterated solvent.

NMR spectra were recorded on a Varian Unity 400 at room temperature at 400 MHz for proton. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; dd, doublet of doublets; 2s, two singlets. Atmospheric pressure chemical ionization mass spectra (APCI) were obtained on a Fisons Platform II Spectrometer (carrier gas: acetonitrile). Chemical ionization mass spectra (CI) were obtained on a Hewlett-Packare 5989 instrument (ammonia ionization, PBMS). Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1$H NMR and MS peaks are given. Optical rotations were determined on a Perkin-Elmer 241 polarimeter using the soldium D line (λ=589 nm) at the indicated temperature and are reported as follows $[\alpha]_D^{temp}$, concentration (c=g/100 mL), and solvent.

Column chromatography was performed with either Baker Silica Gel (40 μm; J. T. Baker, Phillipsburg, N.J.) or Silica Gel 50 (EM Sciences, Gibbstown, N.J.) in glass columns or with Flash 40 (Biotage) columns under low nitrogen pressure. Unless otherwise specified, reagents were used as obtained from commercial sources.

EXAMPLE 1

Racemic [(1R,7S,9R)-1-Tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetic Acid A solution of 3-tert-butyl-7-methyl-3,4-dihydro-2H-benzo[1,4]oxazine (810 mg, 3.95 mmol) in benzene (2 mL) was added to a solution of boron trichloride (1.0 M in xylenes; 4.34 mL, 4.34 mmol) in benzene (5 mL) at 0° C. under a nitrogen atmosphere. Once the addition was complete, the resulting mixture was heated at reflux for 3 hours under a steady stream of nitrogen exiting into an aqueous 5N sodium hydroxide trap, and then recooled to 0° C. A solution of 2,3-dimethoxybenzaldehyde (656 mg, 3.95 mmol), triethylamine (799 mg, 7.90 mmol, 1.1 mL) and benzene (3 mL) was then added and the resulting mixture stirred 3.5 hours before quenching with aqueous 1 N hydrochloric acid. After 1 hour, ethyl acetate was added and the resulting mixture was shaken vigorously. The aqueous layer was alkalized with aqueous 5N sodium hydroxide and the layers separated. The aqueous layer was extracted with ethyl acetate (2×). The organic layers were combined, dried over anhydrous sodium sulfate, filtered, concentrated under reduced pressure, and purified by flash column chromatography (4:1→2:1 hexanes/ethyl acetate) to produce 1.18 g (80%) of racemic [(3R,5S)-3-tert-butyl-7-methyl-3,4-dihydro-2H-benzo[1,4]oxazin-5-yl]-(2,3-dimethoxyphenyl)-methanol as a beige foam.

$^1$H NMR (400 MHz, CDCl$_3$) δ 7.05 (t, 1H), 6.89 (m, 2H), 6.55 (d, 1H), 6.33 (s, 1H), 6.00 (d, 1H), 4.78 (br s, 1H), 4.24 (dd, 1H), 3.88 (s, 3H), 3.83 (m, 1H), 3.78 (s, 3H), 3.20 (br d, 1H), 3.09 (dd, 1H), 2.13 (s, 3H), 0.94 (s, 9H).

Fumaric chloride monoethyl ester (600 mg, 3.69 mmol) was added to a mixture of racemic [(3R,5S)-3-tert-butyl-7-methyl-3,4-dihydro-2H-benzo[1,4]oxazin-5-yl]-(2,3-dimethoxyphenyl)-methanol (1.14 g, 3.08 mmol) and sodium bicarbonate (362 mg, 4.31 mmol) in methylene chloride (6 mL). After stirring 20 hours at ambient temperature, the reaction mixture was diluted with methylene chloride, washed with water (2×) and saturated aqueous sodium chloride, dried over anhydrous sodium sulfate, filtered, concentrated under reduced pressure, and purified by flash column chromatography (2:1 hexanes/ethyl acetate) to produce 1.17 g (76%) of racemic 4-{(3R,5S)-3-tert-butyl-5-[(2,3-dimethoxyphenyl)-hydroxymethyl]-7-methyl-2,3-dihydro-benzo[1,4]oxazin-4-yl}-4-oxo-but-2-enoic acid ethyl ester as a yellow foam.

Potassium carbonate (650 mg, 4.70 mmol) was added to a solution of racemic 4-{(3R,5S)-3-tert-butyl-5-[(2,3-dimethoxyphenyl)-hydroxy-methyl]-7-methyl-2,3-dihydro-benzo[1,4]oxazin-4-yl}-4-oxo-but-2-enoic acid ethyl ester (1.17 g, 2.35 mmol) in ethanol (12 mL). The resulting mixture was stirred at ambient temperature for 18 hours, diluted with ethyl acetate, washed with water (2×) and and saturated aqueous sodium chloride, dried over anhydrous sodium sulfate, filtered, concentrated under reduced pressure and purified by flash column chromatography (3:1 hexanes/ethyl acetate) to give 1.09 g (93%) of the racemic ethyl ester of [(1R,7S,9R)-1-tert-butyl-7-(2,3-dimethoxyphenyl)-5-methyl-10-oxo- 1,2,9,10-tetrahydro-7H-3,8-dioxa-10a-aza-cyclohepta[de]naphthalen-9-yl]-acetic acid as a white foam. [An aliquot can be removed from the reaction mixture prior to work-up to ascertain by TLC or NMR if the product has fully epimerized to the desired isomer.]

MS (APCI): 498 (M+H$^+$).

$^1$H NMR (400 MHz, CDCl$_3$) δ 7.23 (dd, 1H), 7.16 (t, 1H), 6.94 (dd, 1H), 6.63 (s, 1H), 6.09 (s, 1H), 6.01 (s, 1H), 4.70 (dd, 1H), 4.63 (d, 1H), 4.51 (d, 1H), 4.15 (m, 3H), 3.86 (s, 3H), 3.50 (s, 3H), 3.08 (dd, 1H), 2.79 (dd, 1H), 2.11 (s, 3H), 1.24 (t, 3H), 1.02 (s, 9H).

Potassium carbonate (607 mg, 4.39 mmol) was added to a solution of the racemic ethyl ester of [(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetic acid (1.09 g, 2.20 mmol) in methanol (11 mL) and water (1 mL) at ambient temperature. The resulting mixture was heated at reflux for 18 hours, cooled to room temperature and concentrated. The resulting residue was taken up in water, acidified with aqueous hydrochloric acid and extracted with ethyl acetate (3×). The combined organics were washed with brine, dried over anhydrous sodium sulfate, filtered, concentrated under reduced pressure and purified by flash column chromatography (5% methanol/methylene chloride) to give a quantitative yield of the title compound as a white foam.

MS (APCI): 470 (M+H$^+$).

$^1$H NMR (400 MHz, CDCl$_3$) δ 7.23 (d, 1H), 7.18 (t, 1H), 6.92 (d, 1H), 6.63 (s, 1H), 6.09 (s, 1H), 6.00 (s, 1H), 4.64 (m, 2H), 4.51 (d, 1H), 4.14 (dd, 1H), 3.86 (s, 3H), 3.50 (s, 3H), 3.10 (dd, 1H), 2.84 (dd, 1H), 2.11 (s, 3H), 1.03 (s, 9H).

The title compounds of Examples 2–14 were prepared according to procedures analogous to that described in Example 1. The title compounds of Examples 15–36 were also prepared according to procedures analogous to that described in Example 1, beginning with the corresponding substituted 1,2,3,4-tetrahydroquinolines.

EXAMPLE 2

Racemic [(1R,7S,9R)-1-Tert-butyl-7-(2,3-dihydro-benzo[1,4]dioxin-5-yl)-5-methyl-10-oxo-1,2,9,10-tetrahydro-7H-3,8-dioxa-10a-aza-cyclohepta[de]naphthalen-9-yl]-acetic Acid 93% yield.

MS (APCI): 468 (M+H$^+$).

$^1$H NMR (400 MHz, CD$_3$OD) δ 7.16 (d, 1H), 6.91 (t, 1H), 6.84 (d, 1H), 6.67 (s, 1H), 6.04 (s, 1H), 5.95 (s, 1H), 4.67 (d, 1H), 4.62 (m, 1H), 4.43 (d, 1H), 4.17–4.00 (m, 5H), 2.97 (dd, 1H), 2.74 (dd, 1H), 2.12 (s, 3H), 1.00 (s, 9H).

EXAMPLE 3

Racemic [(1R,7S,9R)-1-Tert-butyl-7-(2-chloro-3,4-dimethoxyphenyl)-5-methyl-10-oxo-1,2,9,10-tetrahydro-7H-3,8-dioxa-10a-aza-cyclohepta[de]nalphthalen-9-yl]-acetic Acid 95% yield.

MS (APCI): 504 (M+H$^+$).

$^1$H NMR (400 MHz, CDCl$_3$) δ 7.46 (d, 1H), 6.96 (d, 1H), 6.68 (s, 1H), 6.03 (s, 1H), 5.93 (s, 1H), 4.69 (m, 1H), 4.66 (d, 1H), 4.51 (d, 1H), 4.14 (dd, 1H), 3.93 (s, 3H), 3.83 (s, 3H), 3.11 (dd, 1H), 2.89 (dd, 1H), 2.13 (s, 3H), 1.02 (s, 9H).

EXAMPLE 4

Racemic [(1R,7S,9R)-1-Tert-butyl-7-(2-chlorophenyl)-5-methyl-10-oxo-1,2,9,10-tetrahydro-7H-3,8-dioxa-10a-aza-cyclohepta[de]naphthalen-9-yl]-acetic Acid quantitative yield.

MS (APCI): 444 (M+H$^+$).

$^1$H NMR (400 MHz, CDCl$_3$) δ 7.75 (dd, 1H), 7.40 (t, 1H), 7.33 (m, 2H), 6.68 (s, 1H), 6.09 (s, 1H), 5.90 (s, 1H), 4.69 (dd, 1H), 4.64 (dd, 1H), 4.52 (d, 1H), 4.14 (dd, 1H), 3.13 (dd, 1H), 2.88 (dd, 1H), 2.13 (s, 3H), 1.03 (s, 9H).

EXAMPLE 5

Racemic [(1R,7R,9R)-1-Tert-butyl-7-(2-trifluoromethylphenyl)-5-methyl-10-oxo-1,2,9,10-tetrahydro-7H-3,8-dioxa-10a-aza-cyclohepta[de]naphthalen-9-yl]-acetic Acid 98% yield.

MS (APCI): 478 (M+H$^+$).

$^1$H NMR (400 MHz, CDCl$_3$) δ 7.96 (d, 1H), 7.69 (m, 2H), 7.51 (t, 1H), 6.67 (s, 1H), 6.18 (s, 1H), 5.82 (s, 1H), 4.76 (t, 1H), 4.65 (d, 1H), 4.53 (d, 1H), 4.13 (dd, 1H), 3.11 (dd, 1H), 2.88 (dd, 1H), 2.10 (s, 3H), 1.01 (s, 9H).

EXAMPLE 6

Racemic [(1R,7R,9R)-1-Tert-butyl-7-(3-methoxyphenyl)-5-methyl-10-oxo-1,2,9,10-tetrahydro-7H-3,8-dioxa-10a-aza-cyclohepta[de]naphthalen-9-yl]-acetic Acid 99% yield.

MS (APCI): 440 (M+H$^+$).

$^1$H NMR (400 MHz, CDCl$_3$) δ 7.30 (t, 1H), 6.95 (s, 1H), 6.90 (d, 2H), 6.67 (s, 1H), 6.04 (s, 1H), 5.75 (s, 1H), 4.68 (m, 1H), 4.62 (d, 1H), 4.52 (d, 1H), 4.12 (dd, 1H), 3.82 (s, 3H), 3.12 (dd, 1H), 2.88 (dd, 1H), 2.13 (s, 3H), 1.00 (s, 9H).

EXAMPLE 7

Racemic [(1R,7S,9R)-1-Tert-butyl-7-(2,3-dimethoxyphenyl)-5-chloro-10-oxo-1,2,9,10-tetrahydro-7H-3,8-dioxa-10a-aza-cyclohepta[de]naphthalen-9-yl]-acetic Acid 86% yield.

MS (APCI): 490 (M+H$^+$).

$^1$H NMR (400 MHz, CDCl$_3$) δ 7.20 (m, 2H), 6.97 (d, 1H), 6.87 (s, 1H), 6.22 (s, 1H), 6.09 (s, 1H), 4.67 (m, 2H), 4.53 (d, 1H), 4.16 (dd, 1H), 3.86 (s, 3H), 3.53 (s, 3H), 3.13 (dd, 1H), 2.87 (dd, 1H), 1.03 (s, 9H).

EXAMPLE 8

Racemic [(1R,7S,9R)-1-Tert-butyl-7-(2,3-dihydro-benzo[1,4]dioxin-5-yl)-5-chloro-10-oxo-1,2,9,10-tetrahydro-7H-3,8-dioxa-10a-aza-cyclohepta[de]naphthalen-9-yl]-acetic Acid quantitative yield.

MS (APCI): 488 (M+H$^+$).

$^1$H NMR (400 MHz, CDCl$_3$) δ 7.17 (d, 1H), 6.95 (t, 1H), 6.92 (d, 1H), 6.88 (s, 1H), 6.30 (s, 1H), 6.00 (s, 1H), 4.66 (m, 2H), 4.53 (d, 1H), 4.16 (m, 3H), 4.01 (m, 2H), 3.13 (dd, 1H), 2.88 (dd, 1H), 1.00 (s, 9H).

EXAMPLE 9

Racemic [(1R,7S,9R)-1-Tert-butyl-7-(2-methoxyphenyl)-5-chloro-10-oxo-1,2,9,10-tetrahydro-7H-3,8-dioxa-10a-aza-cyclohepta[de]naphthalen-9-yl]-acetic Acid 96% yield.

MS (APCI): 560 (M+H$^+$).

$^1$H NMR (400 MHz, CDCl$_3$) δ 7.60 (d, 1H), 7.36 (t, 1H), 7.08 (t, 1H), 6.85 (m, 2H), 6.20 (s, 1H), 6.08 (s, 1H), 4.66 (m, 2H), 4.53 (d, 1H), 4.17 (dd, 1H), 3.60 (s, 3H), 3.15 (dd, 1H), 2.87 (dd, 1H), 1.02 (s, 9H).

EXAMPLE 10

Racemic [(1R,7S,9R)-1-Tert-butyl-7-(benzo[1,3]dioxol-4-yl)-5-methyl-10-oxo-1,2,9,10-tetrahydro-7H-3,8-dioxa-10a-aza-cyclohepta[de]naphthalen-9-yl]-acetic Acid 77% yield.

¹H NMR (400 MHz, CDCl₃) δ 7.08 (d, 1H), 6.92 (t, 1H), 6.85 (d, 1H), 6.68 (s, 1H), 6.17 (s, 1H), 5.86 (m, 3H), 4.68 (m, 2H), 4.62 (d, 1H), 4.12 (dd, 1H), 3.08 (dd, 1H), 2.84 (dd, 1H), 2.15 (s, 3H), 0.98 (s, 9H).

EXAMPLE 11

Racemic [(1R,7R,9R)-1-Tert-butyl-7-(2-methylphenyl)-5-methyl-10-oxo-1,2,9,10-tetrahydro-7H-3,8-dioxa-10a-aza-cyclohepta[de]naphthalen-9-yl]-acetic Acid 55% yield.

MS (APCI): 440 (M+H⁺).

¹H NMR (400 MHz, CDCl₃) δ 7.63 (d, 1H), 7.32 (t, 1H), 7.09 (t, 1H), 6.83 (d, 1H), 6.63 (s, 1H), 6.08 (s, 1H), 6.01 (s, 1H), 4.65 (m, 2H), 4.50 (d, 1H), 4.16 (dd, 1H), 3.56 (s, 3H), 3.12 (dd, 1H), 2.86 (dd, 1H), 2.11 (s, 3H), 1.01 (s, 9H).

EXAMPLE 12

Racemic [(1R,7R,9R)-1-Tert-butyl-7-(3-methoxy-2-methyl-phenyl)-5-chloro-10-oxo-1,2,9,10-tetrahydro-7H-3,8-dioxa-10a-aza-cyclohepta[de]naphthalen-9-yl]-acetic Acid 66% yield.

MS (APCI): 474 (M+H⁺).

¹H NMR (400 MHz, CDCl₃) δ 7.25 (m, 2H), 6.86 (m, 2H), 6.15 (d, 1H), 5.88 (s, 1H), 4.65 (m, 2H), 4.52 (d, 1H), 4.12 (dd, 1H), 3.81 (s, 3H), 3.13 (dd, 1H), 2.85 (dd, 1H), 1.78 (s, 3H), 1.00 (s, 9H).

EXAMPLE 13

Racemic [(1R,7S,9R)-1-Methyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetic Acid 35% isolated yield.

MS (PCI): 428 (M+H⁺).

¹H NMR (400 MHz, CDCl₃) δ 7.20 (d, 1H), 7.13 (t, 1H), 6.91 (d, 1H), 6.69 (s, 1H), 6.04 (s, 1H), 5.98 (s, 1H), 5.07 (m, 1H), 4.62 (m, 1H), 4.16 (s, 2H), 3.83 (s, 3H), 3.44 (s, 3H), 3.10 (dd, 1H), 2.80 (dd, 1H), 2.12 (s, 3H), 1.20 (s, 3H).

EXAMPLE 14

Racemic [(1R,7S,9R)-1-Phenyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetic Acid 85% yield.

MS (APCI): 490 (M+H⁺).

¹H NMR (400 MHz, CDCl₃) δ 7.40 (d, 2H), 7.32–7.21 (m, 3H), 7.15 (t, 1H), 6.92 (d, 1H), 6.68 (s, 1H), 6.07 (d, 2H), 6.01 (s, 1H), 4.76 (m, 2H), 4.47 (d, 1H), 3.87 (d, 1H), 3.84 (s, 3H), 3.22 (s, 3H), 3.17 (dd, 1H), 2.88 (br d, 1H), 2.09 (s, 3H).

EXAMPLE 15

Racemic [(6S,8R,10S)-6-Tert-butyl-10-(2,3-dimethoxyphenyl)-2-chloro-7-oxo-5,6,7,8-tetrahydro-4H,10H-9-oxa-6a-aza-cyclohepta[de]naphthalen-8-yl]-acetic Acid 96% yield.

MS (APCI): 488 (M+H⁺).

¹H NMR (400 MHz, CDCl₃) δ 7.15 (m, 3H), 6.96 (m, 1H), 6.47 (s, 1H), 6.28 (s, 1H), 4.78 (t, 1H), 4.29 (t, 1H), 3.89 (s, 3H), 3.60 (s, 3H), 3.07 (dd, 1H), 2.83 (dd, 1H), 2.69 (m, 1H), 2.48 (m, 1H), 2.32 (m, 1H), 1.82 (m, 1H), 0.93 (s, 9H).

EXAMPLE 16

Racemic [(6S,8R,10S)-6-Tert-butyl-10-(2,4-dimethoxyphenyl)-2-chloro-7-oxo-5,6,7,8-tetrahydro-4H 10H-9-oxa-6a-aza-cyclohepta[de]naphthalen-8-yl]-acetic Acid 85% yield.

MS (APCI): 488 (M+H⁺).

¹H NMR (400 MHz, CDCl₃) δ 7.30 (d, 1H), 7.20 (s, 1H), 7.02 (s, 1H), 6.40 (d, 1H), 6.39 (s, 1H), 6.31 (s, 1H), 4.80 (t, 1H), 4.67 (t, 1H), 3.74 (s, 3H), 3.71 (s, 3H), 3.08 (dd, 1H), 3.87 (dd, 1H), 2.61 (m, 1H), 2.46 (m, 1H), 2.17 (m, 1H), 1.76 (m, 1H), 0.68 (s, 9H).

EXAMPLE 17

Racemic [(6S,8R,10S)-6-Tert-butyl-10-(2,3-dimethoxyphenyl)-2-methyl-7-oxo-5,6,7,8-tetrahydro-4H,10H-9-oxa-6a-aza-cyclohepta[de]naphthalen-8-yl]-acetic Acid quantitative yield.

MS (APCI): 468 (M+H⁺).

¹H NMR (400 MHz, CDCl₃) δ 7.18 (m, 2H), 6.94 (m, 2H), 6.28 (s, 1H), 6.26 (s, 1H), 4.76 (t, 1H), 4.28 (dd, 1H), 3.87 (s, 3H), 3.59 (s, 3H), 3.03 (dd, 1H). 2.82 (dd, 1H), 2.66 (m, 1H), 2.47 (m, 1H), 2.31 (m, 1H), 2.16 (s, 3H), 1.82 (m, 1H), 0.92 (s, 9H).

EXAMPLE 18

Racemic [(6S,8R,10S)-6-Tert-butyl-10-(2,4-dimethoxyphenyl)-2-methyl-7-oxo-5,6,7,8-tetrahydro-4H, 10H-9-oxa-6a-aza-cyclohepta[de]naphthalen-8-yl]-acetic Acid 93% yield.

MS (APCI): 468 (M+H⁺).

¹H NMR (400 MHz, CDCl₃) δ 7.24 (m, 1H), 6.93 (s, 1H), 6.39 (s, 1H), 6.38 (m, 1H), 6.32 (s, 1H), 4.81 (t, 1H), 4.66 (dd, 1H), 3.74 (s, 3H), 3.71 (s, 3H), 3.03 (dd, 1H). 2.87 (dd, 1H), 2.62 (m, 1H), 2.44 (m, 1H), 2.24 (s, 3H), 2.19 (m, 1H), 1.78 (m, 1H), 0.70 (s, 9H).

EXAMPLE 19

Racemic [(6S,8R,10S)-6-Tert-butyl-10-(2,3-dihydro-benzo[1,4]dioxin-5-yl)-2-methyl-7-oxo-5,6,7,8-tetrahydro-4H,10H-9-oxa-6a-aza-cyclohepta[de]naphthalen-8-yl]-acetic Acid 91% yield.

MS (APCI): 466 (M+H⁺).

¹H NMR (400 MHz, CDCl₃) δ 7.13 (d, 1H), 6.94 (m, 2H), 6.88 (d, 1H), 6.33 (s, 1H), 6.22 (S, 1H), 4.73 (t, 1H), 4.26 (dd, 1H), 4.16 (m, 2H), 4.03 (m, 2H), 3.03 (dd, 1H), 2.80 (dd, 1H), 2.63 (m, 1H), 2.46 (m, 1H), 2.31 (m, 1H), 2.20 (s, 3H), 1.77 (m, 1H), 0.90 (s, 9H).

EXAMPLE 20

Racemic [(6S,8R,10S)-6-Tert-butyl-10-(2,3-dihydro-benzo[1,4]dioxin-5-yl)-2-chloro-7-oxo-5,6,7,8-tetrahydro-4H,10H-9-oxa-6a-aza-cyclohepta[de]naphthalen-8-yl]-acetic Acid 82% yield.

MS (APCl): 486 (M+H⁺).

¹H NMR (400 MHz, DMSO-d₆) δ 7.38 (s, 1H), 7.04 (d, 1H), 6.92 (m, 2H), 6.31 (s, 1H), 6.06 (s, 1H), 4.60 (t, 1H), 4.20–3.98 (m, 5H), 2.71 (m, 2H), 2.56 (dd, 1 H), 2.38 (m, 1H), 2.27 (m, 1H), 1.72 (m, 1H), 0.83 (s, 9H).

EXAMPLE 21 racemic [(6S,8R,10S)-6-Tert-butyl-10-(benzo[1,3] dioxol-4-yl)-2-chloro-7-oxo-5,6,7,8-tetrahydro-4H ,10H-9-oxa-6a-aza-cyclohepta[de]naphthalen-8-yl]-acetic acid 90% yield.

MS (APCl): 472 (M+H⁺).

¹H NMR (400 MHz, DMSO-d₆) δ 12.26 (s, 1H), 7.42 (s, 1H), 6.98 (m, 3H), 6.38 (s, 1H), 5.96 (dd, 2H), 5.90 (s, 1H), 4.60 (t, 1H), 4.18 (t, 1H), 2.70 (m, 2H), 2.54 (dd, 1H), 2.46–2.26 (m, 2H), 1.71 (m, 1H), 0.81 (s, 9H).

EXAMPLE 22 racemic [(6S,8R,10S)-6-Tert-butyl-10-(2-methoxyphenyl)-2-chloro-7-oxo-5,6,7,8-tetrahydro-4H, 10H-9-oxa-6a-aza-cyclohepta[de]naphthalen-8-yl]-acetic acid quantitative yield.

MS (APCl): 458 (M+H⁺).

¹H NMR (400 MHz, DMSO-d₆) δ 12.23 (s, 1H), 7.49 (d, 1H), 7.38 (m, 2H), 7.06 (m, 2H), 6.20 (s, 1H), 6.10 (s, 1H), 4.60 (t, 1H), 4.12 (t, 1H), 3.58 (s, 3H), 2.72 (m, 2H), 2.59 (dd, 1H), 2.40 (m, 1H), 2.28 (m, 1H), 1.72 (m, 1H), 0.82 (s, 9H).

EXAMPLE 23 racemic [(6S,8R,10S)-6-Isopropyl-10-(2,3-dimethoxyphenyl)-2-chloro-7-oxo-5,6,7,8-tetrahydro-4H, 10H-9-oxa-6a-aza-cyclohepta[de] naphthalen-8-yl]-acetic acid 90% yield.

MS (APCl): 474 (M+H⁺).

¹H NMR (400 MHz, CDCl₃) δ 7.16 (m, 3H), 6.96 (d, 1H), 6.49 (s, 1H), 6.10 (s, 1H), 4.64 (q, 1H), 4.38 (m, 1H), 3.87 (s, 3H), 3.52 (s, 3H), 3.08 (dd, 1H), 2.86 (dd, 1H), 2.74 (m, 2H), 2.08 (m, 2H), 1.89 (m, 1H), 1.02 (d, 3H), 0.92 (d, 3H).

EXAMPLE 24 racemic [(6S,8R, 10R-6-Tert-butyl-10-(3-methoxyphenyl)-2-methyl-7-oxo-5,6,7,8-tetrahydro-4H,10H-9-oxa-6a-aza-cyclohepta[de]naphthalen-8-yl]-acetic acid 97% yield.

MS (APCl): 438 (M+H⁺).

¹H NMR (400 MHz, CDCl₃) δ 7.31 (t, 1H), 6.95 (br d, 2H), 6.90 (d, 2H), 6.30 (s, 1H), 5.99 (s, 1H), 4.77 (t, 1H), 4.29 (t, 1H), 3.82 (s, 3H), 3.02 (dd, 1H), 2.87 (dd, 1H), 2.67 (brd, 1H), 2.46 (m, 1H), 2.32 (m, 1H), 2.18 (s, 3H), 1.78 (m, 1H), 0.90 (s, 9H).

EXAMPLE 25 racemic [(6S,8R,10R)-6-Tert-butyl-10-(3-methoxyphenyl)-2-chloro-7-oxo-5,6,7,8-tetrahydro-4H,10H-9-oxa-6a-aza-cyclohepta[de]naphthalen-8-yl]-acetic acid 76% yield.

MS (APCl): 458 (M+H⁺).

¹H NMR (400 MHz, CDCl₃) δ 7.33 (t, 1H), 7.17 (s, 1H), 6.90 (m, 3H), 6.49 (s, 1H), 5.96 (s, 1H), 4.78 (t, 1H), 4.30 (t, 1H), 3.82 (s, 3H), 3.08 (dd, 1H), 2.82 (dd, 1H), 2.68 (d, 1H), 2.47 (m, 1H), 2.33 (m, 1H), 1.80 (m, 1H), 0.90 (s, 9H).

EXAMPLE 26 racemic [(6S,8R,10S)-6-Tert-butyl-10-(2-methoxyphenyl)-2-methyl-7-oxo-5,6,7,8-tetrahydro-4H, 10H-9-oxa-6a-aza-cyclohepta[de]naphthalen-8-yl]-acetic acid 91% yield.

MS (APCl): 438 (M+H⁺).

¹H NMR (400 MHz, CDCl₃) δ 7.58 (d, 1H), 7.33 (t, 1H), 7.08 (t, 1H), 6.93 (s, 1H), 6.86 (d, 1H), 6.27 (s, 1H), 6.26 (s, 1H), 4.76 (t, 1H), 4.22 (m, 1H), 3.59 (s, 3H), 2.97 (dd, 1H), 2.87 (dd, 1H), 2.65 (m, 1H), 2.45 (m, 1H), 2.30 (m, 1H), 2.15 (s, 3H), 1.78 (m, 1H), 0.90 (s, 9H).

EXAMPLE 27 racemic [(6S,8R,10S)-6-Tert-butyl-10-(2-trifluoromethoxyphenyl)-2-chloro-7-oxo-5,6,7,8-tetrahydro-4H ,10H-9-oxa-6a-aza-cyclohepta[de] naphthalen-8-yl]-acetic acid 70% yield.

MS (APCl): 512 (M+H⁺).

¹H NMR (400 MHz, CDCl₃) δ 7.73 (d, 1H), 7.43 (m, 2H), 7.30 (d, 1H), 7.20 (s, 1H), 6.38 (s, 1H), 6.28 (s, 1H), 4.79 (t, 1H), 4.33 (t, 1H), 3.08 (dd, 1H), 2.86 (dd, 1H), 2.70 (m, 1H), 2.49 (m, 1H), 2.32 (m, 1H), 1.85 (m, 1H), 0.90 (s, 9H).

EXAMPLE 28 racemic [(6S,8R, 10R)-6-Tert-butyl-10-(3-trifluoromethoxyphenyl)-2-chloro-7-oxo-5,6,7,8-tetrahydro-4H, 10H-9-oxa-6a-aza-cyclohepta[de] naphthalen-8-yl]-acetic acid 99% yield.

MS (APCl): 512 (M+H⁺).

¹H NMR (400 MHz, CDCl₃) δ 7.46 (t, 1H), 7.26 (m, 3H), 7.19 (s, 1H), 6.40 (s, 1H), 6.00 (s, 1H), 4.78 (t, 1H), 4.30 (t, 1H), 3.07 (s, 1H), 2.84 (dd, 1H), 2.69 (dd, 1H), 2.48 (br t, 1H), 2.33 (m, 1H), 1.80 (m, 1H), 0.90 (s, 9H).

EXAMPLE 29 racemic [(6S,8R,10R)-6-Tert-butyl-10-(2-methyl-3-methoxyphenyl)-2-chloro-7-oxo-5,6,7,8-tetrahydro-4H,10H-9-oxa-6a-aza-cyclohepta[de]naphthalen-8-yl]-acetic acid 81 % yield.

MS (APCl): 472 (M+H⁺).

¹H NMR (400 MHz, CDCl₃) δ 7.28 (d, 1H), 7.20 (d, 1H), 7.16 (s, 1H), 6.89 (d, 1H), 6.45 (s, 1H), 6.09 (s, 1H), 4.80 (t, 1H), 4.33 (t, 1H), 3.84 (s, 3H), 3.07 (dd, 1H), 2.82 (dd, 1H), 2.69 (m, 1H), 2.48 (m, 1H), 2.30 (m, 1H), 1.88 (s, 3H), 1.84 (m, 1H), 0.92 (s, 9H).

EXAMPLE 30 racemic [(6S,8R,10S)-6-Tert-butyl-10-(2,3-dimethoxyphenyl)-7-oxo-5,6,7,8-tetrahydro-4H, 10H-9-oxa-6a-aza-cyclohepta[de]naphthalen-8-yl]-acetic acid 79% yield.

MS (APCl): 454 (M+H⁺).

¹H NMR (400 MHz, CDCl₃) δ 7.18 (m, 3H), 7.05 (t, 1H), 6.95 (d, 1H), 6.50 (d, 1H), 6.33 (s, 1H), 4.80 (t, 1H), 4.30 (t, 1H), 3.88 (s, 3H), 3.57 (s, 3H), 3.07 (dd, 1H), 2.85 (dd, 1H), 2.70 (m, 1H), 2.50 (m, 1H), 2.33 (m, 1H), 1.85 (m, 1H), 0.93 (s, 9H).

EXAMPLE 31 racemic [(6S,8R,10S)-6-Tert-butyl-10-(benzo[1,3] dioxol-4-yl)-2-methyl-7-oxo-5,6,7,8-tetrahydro-4H, 10H-9-oxa-6a-aza-cyclohepta[de]naphthalen-8-yl]- acetic acid 89% yield.

¹H NMR (400 MHz, CDCl₃) δ 7.07 (d, 1H), 6.99 (s, 1H), 6.93 (t, 1H), 6.85 (d, 1H), 6.44 (s, 1H), 6.13 (s, 1H), 5.88 (d, 2H), 4.77 (t, 1H), 4.29 (t, 1H), 3.00 (dd, 1H), 2.82 (dd, 1H), 2.66 (br d, 1H), 2.46 (m, 1H), 2.31 (m, 1H), 2.21 (s, 3H), 1.77 (m, 1H), 0.89 (s, 9H).

EXAMPLE 32 racemic [(6S,8R 10S)-6-Tert-butyl-10-(2-chloro-3,4-dimethoxyphenyl)-2-chloro-7-oxo-5,6,7,8-tetrahydro-4H,10H-9-oxa-6a-aza-cyclohepta[de] naphthalen-8-yl]-acetic acid 26% isolated yield.

MS (PCl): 523 (M+H⁺).

¹H NMR (400 MHz, CDCl₃) δ 7.38 (d, 1H), 7.17 (s, 1H), 6.97 (d, 1H), 6.42 (s, 1H), 6.20 (s, 1H), 4.77 (t, 1H), 4.31 (t, 1H), 3.92 (s, 3H), 3.85 (s, 3H), 3.04 (dd, 1H), 2.86 (dd, 1H), 2.70 (br d, 1H), 2.50 (m, 1H), 2.31 (m, 1H), 1.87 (m, 1H), 0.93 (s, 9H).

EXAMPLE 33 racemic [(6S,8R,10S)-6-Tert-butyl-10-(2-chloro-3,4-dimethoxyphenyl)-2-methyl-7-oxo-5,6,7,8-tetrahydro-4H, 10H-9-oxa-6a-aza-cyclohepta[de] naphthalen-8-yl]-acetic acid 34% isolated yield.

MS (APCl): 500 (M–H)⁻.

¹H NMR (400 MHz, CDCl₃) δ 7.39 (d, 1H), 6.96 (s, 1H), 6.95 (d, 1H), 6.20 (s, 2H), 4.76 (t, 1H), 4.30 (t, 1H), 3.91 (s, 3H), 3.85 (s, 3H), 3.00 (dd, 1H), 2.87 (dd, 1H), 2.67 (m, 1H), 2.46 (m, 1H), 2.29 (m, 1H), 2.17 (s, 3H), 1.84 (m, 1H), 0.92 (s, 9H).

EXAMPLE 34 racemic [(6S,8S,10S)-6-Tert-butyl-10-(2-chloro-3,4-dimethoxyphenyl)-2-methyl-7-oxo-5,6,7,8-tetrahydro-4H,10H-9-oxa-6a-aza-cyclohepta[de] naphthalen-8-yl]-acetic acid MS (APCl): 502 (M+H⁺).

¹H NMR (400 MHz, CDCl₃) δ 7.09 (d, 1H), 6.92 (s, 2H), 6.73 (d, 1H), 6.36 (s, 1H), 4.82 (t, 1H), 4.68 (t, 1H), 3.82 (s, 3H), 3.81 (s, 3H), 2.25 (s, 3H), 0.70 (s, 9H).

EXAMPLE 35 racemic [(6S,8R,10R)-6-Phenyl-10-(3-methoxyphenyl)-2-methyl-7-oxo-5,6,7,8-tetrahydro-4H, 10H-9-oxa-6a-aza-cyclohepta[de]naphthalen-8-yl]-acetic acid 97% yield.

MS (APCl): 456 (M–H)⁻.

¹H NMR (400 MHz, CDCl₃) δ 7.29 (m, 5H), 7.17 (d, 1H), 7.04 (s, 1H), 6.89 (m, 3H), 6.40 (s, 1H), 5.69 (s, 1H), 5.60 (dd, 1H), 4.42 (dd, 1H), 3.81 (s, 3H), 3.07 (dd, 1H), 2.79 (dd, 1H), 2.72 (m, 2H), 2.60 (m, 1H), 2.22 (s, 3H), 1.92 (m, 1H).

EXAMPLE 36 racemic [(6S,8R,10S)-6-Tert-butyl-10-(benzo[1,3] dioxol-4-yl)-2-chloro-7-oxo-5,6,7,8-tetrahydro-4H, 10H-9-oxa-6a-aza-cyclohepta[de]naphthalen-8-yl]- acetic acid 98% yield.

MS (APCl): 474 (M+H⁺).

¹H NMR (400 MHz, CDCl₃) δ 7.08 (d, 1H), 6.95 (t, 1H), 6.88 (m, 2H), 6.37 (s, 1H), 5.90 (d, 2H), 5.87 (s, 1H), 4.66 (m, 2H), 4.54 (d, 1H), 4.14 (dd, 1H), 3.13 (dd, 1H), 2.86 (dd, 1H), 1.00 (s, 9H).

EXAMPLE 37

[(1R,7S,9R)-1-Tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetic acid and

[(1S,7R,9S)-1-Tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetic acid 1-(3-Dimethylaminopropyl)-3-ethylcarbodiimide hydrochloride (10.1 g, 52.9 mmol), methyl (R)-lactate (3.03 g, 29.1 mol, 2.78 mL) and 4-dimethylaminopyridine (320 mg, 2.65 mmol) were added sequentially to a solution of racemic [(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetic acid (12.42 g, 26.4 mol) and methylene chloride (100 mL). After stirring 48 hours at ambient temperature, the reaction mixture was diluted with methylene chloride, washed with water and saturated aqueous sodium chloride, dried over anhydrous sodium sulfate, filtered, concentrated under reduced pressure, and purified by flash column chromatography (3:1 hexanes/ether) to produce 3.46 g (24%) of each pure isomer of 2R-{[1-tert-butyl-7-(2,3-dimethoxy-phenyl)-5-methyl-10-oxo-1,2,9,10-tetrahydro-7H-3,8-dioxa-10a-aza-cyclohepta[de]naphthalen-9-yl]-acetoxy}-propionic acid methyl ester as white solids, along with mixed fractions. ●(1S,7R,9S)-isomer (less polar isomer).

¹H NMR (400 MHz, CDCl₃) δ 7.24 (m, 1H), 7.17 (t, 1H), 6.94 (d, 1H), 6.61 (s, 1H), 6.08 (s, 1H), 6.00 (s, 1H), 5.06 (q, 1H), 4.71 (dd, 1H), 4.61 (d, 1H), 4.49 (d, 1H), 4.19 (dd, 1H), 3.85 (s, 3H), 3.70 (s, 3H), 3.50 (s, 3H), 3.22 (dd, 1H), 2.89 (dd, 1H), 2.10 (s, 3H), 1.46 (d, 3H), 1.02 (s, 9H). ●(1R,7S,9R)-isomer (more polar isomer).

MS (APCl): 556 (M+H⁺).

¹H NMR (400 MHz, CDCl₃) δ 7.21 (m, 1H), 7.14 (t, 1H), 6.91 (dd, 1H), 6.59 (d, 1H), 6.09 (s, 1H), 5.98 (d, 1H), 5.10 (q, 1H), 4.70 (t, 1H), 4.61 (d, 1H), 4.50 (d, 1H), 4.12 (dd, 1H), 3.83 (s, 3H), 3.68 (s, 3H), 3.48 (s, 3H), 3.10 (dd, 1H), 2.90 (dd, 1H), 2.08 (s, 3H), 1.43 (d, 3H), 1.00 (s, 9H).

Potassium carbonate (99 mg, 720 μmol) was added to a solution of 2R-{[(1R,7S,9R)-1-tert-butyl-7-(2,3-dimethoxy-phenyl)-5-methyl-10-oxo-1,2,9,10-tetrahydro-7H-3,8-dioxa-10a-aza-cyclohepta[de]naphthalen-9-yl]-acetoxy}-propionic acid methyl ester (200 mg, 360 μmol) in methanol (3 mL) and water (0.3 mL). The resulting mixture was heated at reflux for 18 hours. After cooling to room temperature, the reaction mixture was concentrated and the resulting residue taken up in water, acidified with an aqueous solution of 1 N hydrochloric acid and extracted with ethyl acetate (3×). The combined organics were dried over anhydrous sodium sulfate, filtered, concentrated under reduced pressure, and purified by flash column chromatography (80:15:1 chloroform/methanol/saturated ammonium hydroxide). Fractions containing product were concentrated under reduced pressure and the resulting residue diluted with ethyl acetate, washed with aqueous 0.1 N hydrochloric acid, dried over anhydrous sodium sulfate, filtered and concentrated under reduced pressure to give 204 mg (99%) of [(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetic acid as a white solid.

MS (APCl): 470 (M+H$^+$).

$^1$H NMR (400 MHz, CDCl$_3$) δ 7.23 (d, 1H), 7.18 (t, 1H), 6.92 (d, 1H), 6.63 (s, 1H), 6.09 (s, 1H), 6.00 (s, 1H), 4.64 (m, 2H), 4.51 (d, 1H), 4.14 (dd, 1H), 3.86 (s, 3H), 3.50 (s, 3H), 3.10 (dd, 1H), 2.84 (dd, 1H), 2.11 (s, 3H), 1.03 (s, 9H).

[α]$_D^{20}$ −220° (c 0.0104, CHCl$_3$)

2R-{[(1S,7R,9S)-1-Tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetoxy}-propionic acid methyl ester was hydrolyzed in an analogous manner to give 184 mg (99%) of [(1S,7R,9S)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetic acid as a white solid.

[α]$_D^{20}$ 201° (c 0.0105, CHCl$_3$)

EXAMPLE 38 racemic [(1S,7S,9S)-1-Tert-butyl-7-(2,3-dimethoxyphenyl)-5-methyl-10-oxo-1,2,9,10-tetrahydro-7H-3-oxa-8-thia-10a-aza-cyclohepta[de]naphthalen-9-yl]-acetic acid and racemic [(1R,7S,9R)-1-Tert-butyl-7-(2,3-dimethoxyphenyl)-5-methyl-10-oxo-1,2,9,10-tetrahydro-7H-3-oxa-8-thia-10a-aza-cyclohepta[de]naphthalen-9-yl]-acetic acid A mixture of racemic [(3R,5S)-3-tert-butyl-7-methyl-3,4-dihydro-2H-benzo[1,4]oxazin-5-yl]-(2,3-dimethoxyphenyl)-methanol (1.12 g, 3.02 mmol), mercaptosuccinic acid (906 mg, 6.04 mmol), and acetic acid (9 mL) was heated at 55° C. overnight. The reaction was cooled to room temperature and then poured into 100 mL water and stirred 1 hour. Solid was collected by filtration, washed with water and dried to yield 1.38 g (91 %) of 2-[(3-tert-butyl-7-methyl-3,4-dihydro-2H-benzo[1,4]oxazin-5-yl)-(2,3-dimethoxyphenyl)-methylsulfanyl]-succinic acid isomers.

A mixture of 2-[(3-tert-butyl-7-methyl-3,4-dihydro-2H-benzo[1,4]oxazin-5-yl)-(2,3-dimethoxyphenyl)-methylsulfanyl]-succinic acid (1.38 g, 2.74 mmol) and p-toluenesulphonic acid (52 mg, 270 μmol) in chlorobenzene (26 mL) was heated at reflux under nitrogen, removing the water formed with a Soxhlet apparatus containing 3Å molecular sieves. After heating overnight, the reaction mixture was cooled to room temperature and concentrated under reduced pressure to give a brown foam that was triturated in 2:1 hexanes/toluene to give 610 mg (46%) of a mixture of [1-tert-butyl-7-(2,3-dimethoxyphenyl)-5-methyl-10-oxo-1,2,9,10-tetrahydro-7H-3-oxa-8-thia-10a-aza-cyclohepta[de]naphthalen-9-yl]-acetic acid isomers as a beige solid. The mixture of isomers was taken up in methanol (12 mL) with potassium carbonate (347 mg, 2.52 mmol) and heated at reflux until the isomer ratio appeared constant by TLC or NMR. The reaction mixture was cooled to room temperature and concentrated. The resulting residue was taken up in water, acidified with 1 N aqueous hydrochloric acid and extracted with ethyl acetate (3×). The combined organics were dried over anhydrous sodium sulfate, filtered, concentrated under reduced pressure, and purified by flash column chromatography (3:2 hexanes/ethyl acetate) to give 87 mg (16%) of pure racemic [(1S,7S,9S)-1-tert-butyl-7-(2,3-dimethoxyphenyl)-5-methyl-10-oxo-1,2,9,10-tetrahydro-7H-3-oxa-8-thia-10a-aza-cyclohepta[de]naphthalen-9-yl]-acetic acid as a white solid and 358 mg (66%) of pure racemic [(1R,7S,9R)-1-tert-butyl-7-(2,3-dimethoxyphenyl)-5-methyl-10-oxo-1,2,9,10-tetrahydro-7H-3-oxa-8-thia-10a-aza-cyclohepta[de]naphthalen-9-yl]-acetic acid as a white solid.

●(1S,7S,9S)-isomer:

MS (APCl): 486 (M+H$^+$).

$^1$H NMR (400 MHz, CDCl$_3$) δ 7.65 (d, 1H), 7.07 (t, 1H), 7.00 (s, 1H), 6.80 (d, 1H), 6.62 (s, 1H), 5.42 (s, 1H), 4.37 (d, 1H), 4.10 (m, 2H), 3.84 (dd, 1H), 3.77 (s, 3H), 3.37 (s, 3H), 3.23 (dd, 1H), 2.53 (dd, 1H), 2.33 (s, 3H), 0.48 (s, 9H).

●(1R,7S,9R)-isomer:

MS (APCl): 486 (M+H$^+$).

$^1$H NMR (400 MHz, CDCl$_3$) δ 7.34 (d, 1H), 7.16 (t, 1H), 6.93 (d, 1H), 6.56 (s, 1H), 6.16 (s, 1H), 6.10 (s, 1H), 4.54 (d, 1H), 4.50 (d, 1H), 4.13 (dd, 1H), 4.06 (dd, 1H), 3.88 (s, 3H), 3.60 (s, 3H), 3.16 (dd, 1H), 2.54 (dd, 1H), 2.11 (s, 3H), 1.06 (s, 9H).

The title compounds of Examples 39–41 were prepared according to procedures analogous to that described in Example 38.

EXAMPLE 39 racemic [(6S,8R 10S)-6-Tert-butyl-2-chloro-10-(2-methoxyphenyl)-7-oxo-5,6,7,8-tetrahydro-4H,10H-9-thia-6a-aza-cyclohepta[de]naphthalen-8-yl]-acetic acid 11 % yield of only this isomer.

MS (APCl): 474 (M+H$^+$).

$^1$H NMR (400 MHz, CDCl$_3$) δ 7.71 (d, 1H), 7.33 (t, 1H), 7.09 (s, 1H), 7.08 (t, 1H), 6.90 (d, 1H), 6.66 (s, 1H), 6.29 (s, 1H), 4.71 (t, 1H), 3.67 (s, 3H), 3.53 (br d, 1H), 3.09 (dd, 1H), 2.59 (br d, 1H), 2.48 (br d, 1H), 2.31 (m, 2H), 1.62 (m, 1H), 0.96 (s, 9H).

EXAMPLE 40 racemic [(1S,7S,9S)-1-Tert-butyl-7-(2,3-dihydro-benzo[1,4]dioxin-5-yl)-5-methyl-10-oxo-1,2,9,10-tetrahydro-7H-3-oxa-8-thia-10a-aza-cyclohepta[de]naphthalen-9-yl]-acetic acid 51 % yield in cyclization and epimerization. 20% isolated yield of this isomer.

MS (APCl): 484 (M+H$^+$).

$^1$H NMR (400 MHz, CDCl$_3$) δ 7.61 (d, 1H), 6.92 (s, 1H), 6.85 (t, 1H), 6.73 (d, 1H), 6.60 (s, 1H), 5.22 (s, 1H), 4.39 (d, 1H), 4.16–4.06 (m, 4H), 3.97 (m, 2H), 3.87 (dd, 1H), 3.23 (dd, 1H), 2.53 (dd, 1H), 2.33 (s, 3H), 0.48 (s, 9H).

EXAMPLE 41 racemic [(1R,7S,9R)-1-tert-butyl-7-(2,3-dihydro-benzo[1,4]dioxin-5-yl)-5-methyl-10-oxo-1,2,9,10-tetrahydro-7H-3-oxa-8-thia-10a-aza-cyclohepta[de]naphthalen-9-yl]-acetic acid 51% yield in cyclization and epimerization. 57% isolated yield of this isomer.

MS (APCl): 484 (M+H$^+$).

$^1$H NMR (400 MHz, CDCl$_3$) δ 7.23 (d, 1H), 6.93 (t, 1H), 6.89 (d, 1H), 6.57 (s, 1H), 6.22 (s, 1H), 6.04 (s, 1H), 4.55 (d, 1H), 4.48 (d, 1H), 4.00–4.15 (m, 6H), 3.14 (dd, 1H), 2.53 (dd, 1H), 2.14 (s, 3H), 1.01 (s, 9H).

EXAMPLE 42

1-{racemic [(1R,7S,9R)-1-Tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid 1-(3-Dimethylaminopropyl)-3-ethylcarbodiimide hydrochloride (96 mg, 503 μmol) and ethyl isonipecotate (47 mg, 302 μmol, 46 μL) were added sequentially to a solution of racemic [(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetic acid (118 mg, 252 μmol) and methylene chloride (1.5 mL). After stirring 15 hours at ambient temperature, the reaction mixture was diluted with ethyl acetate, washed with water and saturated aqueous sodium chloride, dried over anhydrous sodium sulfate, filtered, concentrated under reduced pressure, and purified by flash column chromatography (1:1 hexanes/ethyl acetate) to produce 114 mg (74%) of the ethyl ester of 1-{racemic [(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid as a white foam.

MS (APCl): 609 (M+H$^+$).

$^1$H NMR (400 MHz, CDCl$_3$) δ 7.19 (m, 2H), 6.93 (dd, 1H), 6.60 (s, 1H), 6.09 (s, 1H), 5.98 (d, 1H), 4.80 (m, 1H), 4.61 (d, 1H), 4.49 (t, 1H), 4.32 (dd, 1H), 4.23 (dd, 1H), 4.12 (m, 2H), 3.91 (m, 1H), 3.86 (s, 3H), 3.49 (s, 3H), 3.12 (m, 2H), 2.80 (m, 2H), 2.49 (m, 1H), 2.09 (s, 3H), 1.90 (m, 2H), 1.76–1.58 (m, 2H), 1.24 (m, 3H), 1.03 (s, 9H).

Potassium carbonate (52 mg, 374 μmol) was added to a solution of the ethyl ester of 1-{racemic [(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid (114 mg, 187 mol) in methanol (2 mL) and water (0.2 mL). The resulting mixture was heated at reflux for 17 hours. After cooling to room temperature, the reaction mixture was concentrated and the resulting residue taken up in water, acidified with an aqueous solution of 1 N hydrochloric acid and extracted with ethyl acetate (3×). The combined organics were dried over anhydrous sodium sulfate, filtered, concentrated under reduced pressure, and purified by flash column chromatography (5% methanol/methylene chloride) to give 79 mg (73%) of the title compound as a white solid.

MS (APCl): 581 (M+H$^+$).

$^1$H NMR (400 MHz, CDCl$_3$) δ 7.22 (d, 1H), 7.13 (t, 1H), 6.91 (d, 1H), 6.59 (s, 1H), 6.09 (s, 1H), 5.99 (d, 1H), 4.79 (m, 1H), 4.62 (d, 1H), 4.50 (m, 1H), 4.31 (dd, 1H), 4.23 (dd, 1H), 3.90 (m, 1H), 3.88 (s, 3H), 3.49 (s, 3H), 3.12 (m, 2H), 2.80 (m, 2H), 2.54 (m, 1H), 2.10 (s, 3H), 1.92–1.63 (m, 3H), 1.24 (s, 1H), 1.02 (s, 9H).

The title compounds of Examples 43–147 were prepared according to procedures analogous to that described in Example 42. In some cases where the racemic acetic acid cores were coupled to chiral amines, the diastereomers were separable by chromatography.

EXAMPLE 43

1-{racemic [(6S,8R,10S)-6-Tert-butyl-10-(2,3-dimethoxyphenyl)-2-chloro-7-oxo-5,6,7,8-tetrahydro-4H,10H-9-oxa-6a-aza-cyclohepta[de]naphthalen-8-yl]-acetyl}-piperidine-4-carboxylic acid 99% yield.

MS (APCl): 599 (M+H$^+$).

$^1$H NMR (400 MHz, CDCl$_3$) δ 7.12 (m, 3H), 6.82 (m, 1H), 6.42 (m, 1H), 6.25 (s, 1H), 4.75 (m, 1H), 4.43 (m, 1H), 4.32 (dd, 1H), 3.90 (m, 1H), 3.87 (s, 3H), 3.57 (s, 3H), 0.91 (s, 9H).

EXAMPLE 44

1-{racemic [(6S,8R,10S)-6-Tert-butyl-10-(2,3-dimethoxyphenyl)-2-chloro-7-oxo-5,6,7,8-tetrahydro-4H,10H-9-oxa-6a-aza-cyclohepta[de]naphthalen-8-yl]-acetyl}-piperidine-3-carboxylic acid 82% yield.

MS (APCl): 599 (M+H$^+$).

$^1$H NMR (400 MHz, CDCl$_3$, diastereomeric mixture) δ 7.16 (m, 2H), 7.12 (s, 1H), 6.96 (m, 1H), 6.43 (s, 1H), 6.27 (m, 1H), 4.77 (t, 1H), 4.55 (dd, 1H), 4.44 (m, 1H), 3.87 (s, 3H), 3.60 (s, 3H), 0.92 (s, 9H).

EXAMPLE 45

1-{racemic [(6S,8R, 10S)-6-Tert-butyl-10-(2,4-dimethoxyphenyl)-2-chloro-7-oxo-5,6,7,8-tetrahydro-4H, 10H-9-oxa-6a-aza-cyclohepta[de]naphthalen-8-yl]-acetyl}-piperidine-4-carboxylic acid 77% yield.

MS (APCl): 599 (M+H$^+$).

$^1$H NMR (400 MHz, CDCl$_3$) δ 7.43 (d, 1H), 7.27 (s, 1H), 6.99 (d, 1H), 6.42 (d, 1H), 6.37 (s, 1H), 6.30 (s, 1H), 4.84 (q, 1H), 4.76 (t, 1H), 4.32 (dd, 1H), 3.91 (br s, 1H), 3.73 (s, 3H), 3.70 (s, 3H), 3.10 (m, 2H), 2.80 (m, 2H), 2.54 (m, 3H), 2.16 (m, 1H), 1.90 (m, 2H), 1.76 (m, 1H), 1.59 (m, 2H), 0.65 (s, 9H).

EXAMPLE 46

1-{racemic [(6S,8R,10S)-6-Tert-butyl-10-(2,3-dimethoxyphenyl)-2-methyl-7-oxo-5,6,7,8-tetrahydro-4H, 10H-9-oxa-6a-aza-cyclohepta[de]naphthalen-8-yl]-acetyl}-piperidine-4-carboxylic acid quantitative yield.

MS (APCl): 579 (M+H$^+$).

$^1$H NMR (400 MHz, CDCl$_3$) δ 7.17 (m, 2H), 6.92 (m, 2H), 6.29 (s, 1H), 6.22 (d, 1H), 4.76 (br s, 1H), 4.40 (m, 2H), 3.92 (br s, 1H), 3.87 (s, 3H), 3.58 (s, 3H), 3.10 (m, 2H), 2.85 (m, 2H), 2.55 (m, 3H), 2.30 (brs, 1H), 2.13 (s, 3H), 1.91–1.62 (m, 4H), 1.24 (s, 1H), 0.93 (s, 9H).

EXAMPLE 47

1-{racemic [(6S,8R,10S)-6-Tert-butyl-10-(2,3-dimethoxyphenyl)-2-methyl-7-oxo-5,6,7,8-tetrahydro-4H, 10H-9-oxa-6a-aza-cyclohepta[de]naphthalen-8-yl]-acetyl}-piperidine-3-carboxylic acid 94% yield.

MS (APCl): 579 (M+H$^+$).

¹H NMR (400 MHz, CDCl₃, diastereomeric mixture) δ 7.17 (m, 2H), 6.93 (d, 1H), 6.91 (s, 1H), 6.28 (m, 1H), 6.23 (s, 1H), 4.76 (t, 1H), 3.87 (s, 3H), 3.58 (s, 3H), 2.13 (s, 3H), 0.93 (s, 9H).

EXAMPLE 48

1-{racemic [(6S,8R,10S)-6-Tert-butyl-10-(2,4-dimethoxyphenyl)-2-methyl-7-oxo-5,6,7,8-tetrahydro-4H, 10H-9-oxa-6a-aza-cyclohepta[de]naphthalen-8-yl]-acetyl}-piperidine-4-carboxylic acid quantitative yield.
MS (APCl): 579 (M+H⁺).
¹H NMR (400 MHz, CDCl₃) δ 7.42 (d, 1H), 7.00 (s, 1H), 6.80 (s, 1H), 6.40 (m, 1H), 6.38 (s, 1H), 6.33 (s, 1H), 4.85 (m, 1H), 4.78 (m, 1H), 4.32 (m, 1H), 3.92 (m, 1H), 3.72 (s, 3H), 3.70 (s, 3H), 3.13 (m, 1H), 3.07 (m, 1H), 2.80 (m, 2H), 2.51 (m, 3H), 2.24 (s, 3H), 2.13 (m, 1H), 1.90 (m, 2H), 1.75 (m, 1H), 1.60 (m, 1H), 0.90 (s, 1H), 0.68 (s, 9H).

EXAMPLE 49

1-{racemic [(6S,8R,10S)-6-Tert-butyl-10-(2,4-dimethoxyphenyl)-2-methyl-7-oxo-5,6,7,8-tetrahydro-4H,10H-9-oxa-6a-aza-cyclohepta[de]naphthalen-8-yl]-acetyl}-piperidine-3-carboxylic acid quantitative yield.
MS (APCl): 579 (M+H⁺).
¹H NMR (400 MHz, CDCl₃, diastereomeric mixture) δ 7.40 (m, 1H), 7.01 (m, 1H), 6.80 (s, 1H), 6.40 (m, 2H), 6.33 (s, 1H), 4.87 (m, 1H), 4.76 (m, 1H), 3.73 (s, 3H), 3.71 (d, 3H), 2.24 (s, 3H), 0.68 (s, 9H).

EXAMPLE 50

1-{racemic [(6S,8R, 10S)-6-Tert-butyl-10-(2,3-dihydro-benzo[1,4]dioxin-5-yl)-2-methyl-7-oxo-5,6,7,8-tetrahydro-4H, 10H-9-oxa-6a-aza-cyclohepta[de]naphthalen-8-yl]-acetyl}-piperidine-4-carboxylic acid 95% yield.
MS (APCl): 577 (M+H⁺).
¹H NMR (400 MHz, CDCl₃) δ 7.12 (m, 1H), 6.90 (m, 3H), 6.88 (m, 1H), 6.30 (br d, 1H), 6.22 (s, 1H), 4.75 (m, 1H), 2.16 (s, 3H), 1.25 (s, 1H), 0.88 (s, 9H).

EXAMPLE 51

1-{racemic [(6S,8R,10S)-6-Tert-butyl-10-(2,3-dihydro-benzo[1,4]dioxin-5-yl)-2-methyl-7-oxo-5,6,7,8-tetrahydro-4H,10H-9-oxa-6a-aza-cyclohepta[de]naphthalen-8-yl]-acetyl}-piperidine-3-carboxylic acid quantitative yield.
MS (APCl): 577 (M+H⁺).
¹H NMR (400 MHz, CDCl₃, diastereomeric mixture) δ 7.14 (m, 1H), 6.93 (m, 2H), 6.87 (d, 1H), 6.31 (br s, 1H), 6.22 (m, 1H), 4.73 (t, 1H), 4.56 (dd, 1H), 4.40 (m, 1H), 4.18 (m, 2H), 2.15 (s, 3H), 0.90 (s, 9H).

EXAMPLE 52

1-{racemic [(6S,8R,10S)-6-Tert-butyl-10-(2,4-dimethoxyphenyl)-2-chloro-7-oxo-5,6,7,8-tetrahydro-4H, 10H-9-oxa-6a-aza-cyclohepta[de]naphthalen-8-yl]-acetyl}-piperidine-3-carboxylic acid 99% yield.
MS (APCl): 599 (M+H⁺).

¹H NMR (400 MHz, CDCl₃, diastereomeric mixture) δ 7.40 (m, 1H), 7.26 (d, 1H), 6.99 (s, 1H), 6.42 (d, 1H), 6.38 (s, 1H), 6.31 (s, 1H), 4.86 (m, 1H), 4.77 (m, 1H), 4.56 (dd, 1H), 3.74 (s, 1H), 3.73 (s, 3H), 3.39 (app dd, 3H), 0.67 (s, 9H).

EXAMPLE 53

(2R)-1-{6R,8S, 10R-[6-Tert-butyl-10-(2,3-dimethoxyphenyl)-2-methyl-7-oxo-5,6,7,8-tetrahydro-4H, 10H-9-oxa-6a-aza-cyclohepta[de]naphthalen-8-yl]-acetyl}-2R-piperidine-2-carboxylic acid 93% yield.
MS (APCl): 579 (M+H⁺).
¹H NMR (400 MHz, CDCl₃) δ 7.20 (m, 2H), 6.92 (m, 2H), 6.28 (s,1H), 6.23 (br s, 1H), 5.24 (m,1H), 3.88 (s, 3H), 3.56 (s, 3H), 2.13 (s, 3H), 0.91 (s, 9H).

EXAMPLE 54

(2R)-1-{6S,8R,10S-[6-Tert-butyl-10-(2,3-dimethoxyphenyl)-2-methyl-7-oxo-5,6,7,8-tetrahydro-4H ,10H-9-oxa-6a-aza-cyclohepta[de]naphthalen-8-yl]-acetyl}-2R-piperidine-2-carboxylic acid quantitative yield.
MS (APCl): 579 (M+H⁺).
¹H NMR (400 MHz, CDCl₃) δ 7.23 (d, 1H), 7.14 (t, 1H), 6.92 (m, 2H), 6.29 (s, 1H), 6.24 (s, 1H), 3.88 (s, 3H), 3.58 (s, 3H), 2.12 (s, 3H), 0.92 (s, 9H).

EXAMPLE 55

(2S)-1-{6S,8R ,10S-[6-Tert-butyl-10-(2,3-dimethoxyphenyl)-2-methyl-7-oxo-5,6,7,8-tetrahydro-4H, 10H-9-oxa-6a-aza-cyclohepta[de]naphthalen-8-yl]-acetyl}-2S-piperidine-2-carboxylic acid quantitative yield.
MS (APCl): 579 (M+H⁺).
¹H NMR (400 MHz, CDCl₃) δ 7.23 (s, 1H), 7.17 (t, 1H), 6.92 (d, 1H), 6.90 (s, 1H), 6.28 (s, 1H), 6.22 (s, 1H), 5.23 (br d, 1H), 4.76 (m, 1H), 4.43 (m, 1H), 3.86 (s, 3H), 3.56 (s, 3H), 2.12 (s, 3H), 0.92 (s, 9H).

EXAMPLE 56

(2R)-1 -{6R,8S,10OR-[6-Tert-butyl-10-(2,3-dimethoxyphenyl)-2-methyl-7-oxo-5,6,7,8-tetrahydro-4H, 10H-9-oxa-6a-aza-cyclohepta[de]naphthalen-8-yl]-acetyl}-2S-piperidine-2-carboxylic acid quantitative yield.
MS (APCl): 579 (M+H⁺).
¹H NMR (400 MHz, CDCl₃) δ 7.18 (m, 2H), 6.92 (d, 1H), 6.90 (s, 1H), 6.29 (s, 1H), 6.23 (s, 1H), 5.37 (br d, 1H), 4.72 (m, 1H), 4.48 (m, 1H), 3.88 (s, 3H), 3.58 (s, 3H), 2.13 (s, 3H), 0.92 (s, 9H).

EXAMPLE 57

1-{racemic [(6S,8R,10S)-6-Tert-butyl-10-(2,3-dihydro-benzo[1,4]dioxin-5-yl)-2-chloro-7-oxo-5,6,7,8-tetrahydro-4H,10H-9-oxa-6a-aza-cyclohepta[de]naphthalen-8-yl]-acetyl}-piperidine-4-carboxylic acid 79% yield.
MS (APCl): 597 (M+H⁺).

¹H NMR (400 MHz, CDCl₃) δ 7.11 (m, 2H), 6.90 (m, 2H), 6.50 (m, 1H), 6.18 (s, 1H), 4.75 (m, 1H), 4.39 (m, 1H), 4.25 (d, 1H), 4.17 (m, 2H), 4.02 (m, 2H), 3.91 (m, 1H), 3.10 (m, 2H), 2.87–2.52 (m, 4H), 2.30 (m, 1H), 1.91 (m, 2H), 1.78 (m, 2H), 1.62 (m, 2H), 0.89 (s, 9H).

EXAMPLE 58

1-{racemic [(6S,8R, 10S-6-Tert-butyl-10-(2,3-dihydro-benzo[1,4]dioxin-5-yl)-2-chloro-7-oxo-5,6,7,8-tetrahydro-4H, 10H-9-oxa-6a-aza-cyclohepta[de]naphthalen-8-yl]-acetyl}-piperidine-3-carboxylic acid 93% yield.

MS (APCl): 597 (M+H⁺).

¹H NMR (400 MHz, CDCl₃, diastereomeric mixture) δ 7.12 (s, 2H), 6.90 (m, 2H), 6.50 (s, 1H), 6.18 (d, 1H), 4.66 (t, 1H), 4.54 (d, 1H), 4.42 (m, 1H), 4.19 (m, 2H), 4.03 (m, 2H), 3.91 (m, 1H), 3.38–2.32 (m, 8H), 2.07 (m, 1H), 1.75–1.44 (m, 4H), 0.89 (s, 9H).

EXAMPLE 59

1-{racemic [(6S,8R,10S)-6-Tert-butyl-10-(benzo[1,3]dioxol-4-yl)-2-chloro-7-oxo-5,6,7,8-tetrahydro-4H,10H-9-oxa-6a-aza-cyclohepta[de]naphthalen-8-yl]-acetyl}-piperidine-4-carboxylic acid 96% yield.

MS (APCl): 583 (M+H⁺).

¹H NMR (400 MHz, CDCl₃) δ 7.15 (d, 1H), 7.03 (t, 1H), 6.92 (t, 1H), 6.83 (m, 1H), 6.58 (br d, 1H), 6.08 (s, 1H), 5.88 (d, 2H), 4.75 (m, 1H), 4.47 (m, 1H), 4.32 (dd, 1H), 3.89 (m, 1H), 3.10 (m, 2H), 2.87–2.52 (m, 5H), 2.32 (m, 1H), 1.91 (m, 2H), 1.79 (m, 1H), 1.61 (m, 2H), 0.89 (s, 9H).

EXAMPLE 60

1-{racemic [(6S,8R,10S)-6-Tert-butyl-10-(benzo[1,3]dioxol-4-yl)-2-chloro-7-oxo-5,6,7,8-tetrahydro-4H 10H-9-oxa-6a-aza-cyclohepta[de]naphthalen-8-yl]-acetyl}-piperidine-3-carboxylic acid 99% yield.

MS (APCl): 583 (M+H⁺).

¹H NMR (400 MHz, CDCl₃, diastereomeric mixture) δ 7.14 (s, 1H), 7.04 (m, 1H), 6.91 (m, 1H), 6.84 (d, 1H), 6.58 (br s, 1H), 6.09 (d, 1H), 5.88 (d, 2H), 4.75 (t, 1H), 4.46 (m, 1H), 0.88 (s, 9H).

EXAMPLE 61

1-{racemic [(6S,8R, 10S)-6-Tert-butyl-10-(2-methoxyphenyl)-2-chloro-7-oxo-5,6,7,8-tetrahydro-4H, 10H-9-oxa-6a-aza-cyclohepta[de]naphthalen-8-yl]-acetyl}-piperidine-4-carboxylic acid 99% yield.

MS (APCl): 569 (M+H⁺).

¹H NMR (400 MHz, CDCl₃) δ 7.56 (m, 1H), 7.32 (m, 1H), 7.11 (d, 1H), 7.06 (t, 1H), 6.88 (d, 1H), 6.42 (m, 1H), 6.24 (s, 1H), 4.75 (m, 1H), 4.40 (m, 1H), 4.30 (br d, 1H), 3.90 (m, 1H), 3.60 (s, 3H), 3.10 (m, 2H), 2.85 (m, 2H), 2.60 (m, 3H), 2.31 (m, 1H), 1.92–1.60 (m, 5H), 0.90 (s, 9H).

EXAMPLE 62

1-{racemic [(6S,8R,10S)-6-Tert-butyl-10-(2-methoxyphenyl)-2-chloro-7-oxo-5,6,7,8-tetrahydro-4H 10H-9-oxa-6a-aza-cyclohepta[de]naphthalen-8-yl]-acetyl}-piperidine-3-carboxylic acid 97% yield.

MS (APCl): 569 (M+H⁺).

¹H NMR (400 MHz, CDCl₃, diastereomeric mixture) δ 7.57 (m, 1H), 7.32 (t, 1H), 7.10 (s, 1H), 7.08 (t, 1H), 6.88 (d, 1H), 6.42 (s, 1H), 6.24 (d, 1H), 4.75 (t, 1H), 4.43 (m, 1H), 3.62 (s, 3H), 0.92 (s, 9H).

EXAMPLE 63

1-{racemic [(6S,8R, 10S)-6-Isopropyl-10-(2,3-dimethoxyphenyl)-2-chloro-7-oxo-5,6,7,8-tetrahydro-4H, 10H-9-oxa-6a-aza-cyclohepta[de]naphthalen-8-yl]-acetyl}-piperidine-3-carboxylic acid quantitative yield.

MS (APCl): 585 (M+H⁺).

¹H NMR (400 MHz, CDCl₃, diastereomeric mixture) δ 7.19 (m, 2H), 7.10 (s, 1H), 6.93 (d, 1H), 6.47 (s, 1H), 6.10 (br s, 1H), 4.63 (m, 1H), 4.52 (m, 1H), 3.87 (s, 3H), 3.50 (app t, 3H), 1.02 (d, 3H), 0.92 (d, 3H).

EXAMPLE 64

1-{racemic [(6S,8R, 10S)-6-Isopropyl-10-(2,3-dimethoxyphenyl)-2-chloro-7-oxo-5,6,7,8-tetrahydro-4H, 10H-9-oxa-6a-aza-cyclohepta[de]naphthalen-8-yl]-acetyl}-piperidine-4-carboxylic acid quantitative yield.

MS (APCl): 585 (M+H⁺).

¹H NMR (400 MHz, CDCl₃) δ 7.16 (m, 2H), 7.09 (s, 1H), 6.92 (m, 1H), 6.47 (m, 1H), 6.10 (s, 1H), 4.62 (m, 1H), 4.51 (m, 1H), 4.32 (dd, 1H), 3.88 (m, 1H), 3.86 (s, 3H), 3.50 (s, 3H), 3.11 (m, 2H), 2.83–2.74 (m, 4H), 2.53 (m, 1H), 2.08 (m, 2H), 1.90 (m, 2H), 1.77–1.62 (m, 2H), 1.24 (s, 1H), 1.02 (d, 3H), 0.91 (d, 3H).

EXAMPLE 65

1-{racemic [(6S,8R. 10S)-6-Tert-butyl-10-(2-methoxyphenyl)-2-methyl-7-oxo-5,6,7,8-tetrahydro-4H, 10H-9-oxa-6a-aza-cyclohepta[de]naphthalen-8-yl]-acetyl}-piperidine-4-carboxylic acid 98% yield.

MS (APCl): 549 (M+H⁺).

¹H NMR (400 MHz, CDCl₃) δ 7.57 (dd, 1H), 7.33 (m, 1H), 7.07 (t, 1H), 6.91 (s, 1H), 6.87 (d, 1H), 6.29 (s, 1H), 6.22 (d, 1H), 4.75 (m, 1H), 4.42 (m, 1H), 3.93 (br s, 1H), 3.62 (s, 3H), 3.13 (m, 1H), 3.01 (m, 1H), 2.81 (m, 2H), 2.53 (m, 4H), 2.30 (m, 1H), 2.13 (s, 3H), 1.92 (m, 2H), 1.77–1.63 (m, 3H), 0.92 (s, 9H).

EXAMPLE 66

1-{racemic [(6S,8R,10S)-6-Tert-butyl-10-(2-methoxyphenyl)-2-methyl-7-oxo-5,6,7,8-tetrahydro-4H 10 H-9-oxa-6a-aza-cyclohepta[de]naphthalen-8-yl]-acetyl}-piperidine-3-carboxylic acid 94% yield.

MS (APCl): 549 (M+H⁺).

¹H NMR (400 MHz, CDCl₃, diastereomeric mixture) δ 7.58 (m, 1H), 7.33 (t, 1H), 7.08 (m, 1H), 6.91 (s, 1H), 6.87 (d, 1H), 6.28 (m, 1H), 6.23 (s, 1H), 4.75 (t, 1H), 4.59 (dd, 1H), 4.43 (m, 1H), 3.62 (s, 3H), 2.14 (s, 3H), 0.92 (s, 9H).

EXAMPLE 67

1-{racemic [(6S,8R,10R)-6-Tert-butyl-10-(3-methoxyphenyl)-2-methyl-7-oxo-5,6,7,8-tetrahydro-4H, 10H-9-oxa-6a-aza-cyclohepta[de]naphthalen-8-yl]-acetyl}-piperidine-4-carboxylic acid quantitative yield.

MS (APCl): 549 (M+H⁺).

¹H NMR (400 MHz, CDCl₃, rotameric mixture) δ 7.31 (t, 1H), 6.90 (m, 4H), 6.25 (d, 1H), 5.95 (s, 1H), 4.74 (m, 1H), 4.47 (m, 1H), 4.32 (dd, 1H), 3.92 (d, 1H), 3.83 and 3.82 (2s, 3H), 3.09 (m, 2H), 2.82 (m, 2H), 2.62 (m, 1H), 2.52 (m, 2H), 2.30 (m, 1H), 2.15 (s, 3H), 1.91 (m, 2H), 1.76–1.60 (m, 3H), 0.90 (s, 9H).

EXAMPLE 68

1-{racemic [(6S,8R,10R)-6-Tert-butyl-10-(3-methoxyphenyl)-2-methyl-7-oxo-5,6,7,8-tetrahydro-4H,10H-9-oxa-6a-aza-cyclohepta[de]naphthalen-8-yl]-acetyl}-piperidine-3-carboxylic acid 97% yield.

MS (APCl): 549 (M+H⁺).

¹H NMR (400 MHz, CDCl₃, diastereomeric mixture) δ 7.30 (t, 1H), 6.97 (br s, 1H), 6.90 (m, 3H), 6.27 (br s, 1H), 5.95 (br s, 1H), 4.75 (t, 1H), 4.48 (m, 1H), 3.83 (s, 3H), 2.15 (s, 3H), 0.90 (s, 9H).

EXAMPLE 69

1-{racemic [(6S.8R, 10R)-6-Tert-butyl-10-(3-methoxyphenyl)-2-chloro-7-oxo-5,6,7,8-tetrahydro-4H, 10H-9-oxa-6a-aza-cyclohepta[de]naphthalen-8-yl]-acetyl}-piperidine-4-carboxylic acid quantitative yield.

MS (APCl): 569 (M+H⁺).

¹H NMR (400 MHz, CDCl₃) δ 7.32 (t, 1H), 7.13 (s, 1H), 6.93 (s, 2H), 6.89 (s, 1H), 6.47 (d, 1H), 5.93 (s, 1H), 4.78 (m, 1H), 4.48 (m, 1H), 4.33 (dd, 1H), 3.91 (d, 1H), 3.84 (s, 3H), 3.10 (m, 2H), 2.82 (m, 2H), 2.68 (d, 1H), 2.54 (brt, 2H), 2.33 (m, 1H), 1.92 (m, 2H), 1.80–1.62 (m, 3H), 0.89 (s, 9H).

EXAMPLE 70

1-{racemic [(6S, 8R, 10R)-6-Tert-butyl-10-(3-methoxyphenyl)-2-chloro-7-oxo-5,6,7,8-tetrahydro-4H, 10H-9-oxa-6a-aza-cyclohepta[de]naphthalen-8-yl]-acetyl}-piperidine-3-carboxylic acid quantitative yield.

MS (APCl): 569 (M+H⁺).

¹H NMR (400 MHz, CDCl₃, diastereomeric mixture) δ 7.32 (t, 1H), 7.12 (s, 10 1H), 6.92 (m, 3H), 6.45 (s, 1H), 5.93 (s, 1H), 4.78 (t, 1H), 4.50 (dd, 1H), 4.48 (m, 1H), 3.83 (s, 3H), 0.89 (s, 9H).

EXAMPLE 71

1-{racemic [(6S,8R.10S)-6-Tert-butyl-10-(2-trifluoromethoxyphenyl)-2-chloro-7-oxo-5,6,7,8-tetrahydro-4H, 10H-9-oxa-6a-aza-cyclohepta[de]naphthalen-8-yl]-acetyl}-piperidine-4-carboxylic acid 92% yield.

MS (APCl): 623 (M+H⁺).

¹H NMR (400 MHz, CDCl₃) δ 7.73 (s, 1H), 7.43 (m, 2H), 7.30 (d, 1H), 7.15 (s, 1H), 6.33 (s, 1H), 6.26 (d, 1H), 4.78 (t, 1H), 4.51 (m, 1H), 4.07–3.84 (m, 2H), 20 0.89 (s, 9H).

EXAMPLE 72

1-{racemic [(6S,8R,10S)-6-Tert-butyl-10-(2-trifluoromethoxyphenyl)-2-chloro-7-oxo-5,6,7,8-tetrahydro-4H, 10H-9-oxa-6a-aza-cyclohepta[de]naphthalen-8-yl]-acetyl}-piperidine-3-carboxylic acid quantitative yield.

MS (APCl): 623 (M+H⁺).

¹H NMR (400 MHz, CDCl₃, diastereomeric mixture) δ 7.72 (m, 1H), 7.43 (m, 2H), 7.30 (d, 1H), 7.16 (s, 1H), 6.33 (m, 1H), 6.27 (s, 1H), 4.79 (m, 1H), 4.50 (m, 1H), 4.34 (dd, 1H), 3.90 (br m, 1H), 3.14 (m, 1H), 3.08 (dd, 1H), 2.82 (m, 2H), 2.68 (m, 1H), 2.56 (m, 2H), 2.32 (m, 1H), 1.92–1.58 (m, 5H), 0.89 (s, 9H).

EXAMPLE 73

1-{racemic [(6S,8R,10R)-6-Tert-butyl-10-(3-trifluoromethoxyphenyl)-2-chloro-7-oxo-5,6,7,8-tetrahydro-4H, 10H-9-oxa-6a-aza-cyclohepta[de]naphthalen-8-yl]-acetyl}-piperidine-4-carboxylic acid 72% yield.

MS (APCl): 623 (M+H⁺).

¹H NMR (400 MHz, CDCl₃) δ 7.44 (m, 1H), 7.14 (s, 1H), 6.33 (d, 1H), 5.95 (s, 1H), 4.75 (m, 1H), 4.46 (m, 1H), 4.30 (t, 1H), 0.88 (s, 9H).

EXAMPLE 74

1-{racemic [(6S,8R,10R)-6-Tert-butyl-10-(3-trifluoromethoxyphenyl)-2-chloro-7-oxo-5,6,7,8-tetrahydro-4H, 10H-9-oxa-6a-aza-cyclohepta[de]naphthalen-8-yl]-acetyl}-piperidine-3-carboxylic acid 83% yield.

MS (APCl): 623 (M+H⁺).

¹H NMR (400 MHz, CDCl₃, diastereomeric mixture) δ 7.43 (t, 1H), 7.13 (s, 1 H), 6.33 (s, 1H), 5.96 (s, 1H), 4.75 (t, 1H), 4.46 (m, 1H), 0.88 (s, 9H).

EXAMPLE 75

1-{racemic [(6S,8R,10R)-6-Tert-butyl-10-(2-methyl-3-methoxyphenyl)-2-chloro-7-oxo-5,6,7,8-tetrahydro-4H, 10H-9-oxa-6a-aza-cyclohepta[de]naphthalen-8-yl]-acetyl}-piperidine-4-carboxylic acid 75% yield.

MS (APCl): 583 (M+H⁺).

¹H NMR (400 MHz, CDCl₃) δ 7.27 (m, 1H), 7.17 (t, 1H), 7.13 (s, 1H), 6.89 (m, 1H), 6.40 (d, 1H), 6.08 (s, 1H), 4.79 (m, 1H), 4.49 (m, 1H), 4.33 (dd, 1H), 3.90 (m, 1H), 3.85 (s, 3H), 3.09 (m, 2H), 2.80 (m, 3H), 2.69 (m, 1H), 2.54 (m, 2H), 2.11 (m, 1H), 1.91 (s, 3H), 1.88–1.55 (m, 4H), 0.92 (s, 9H).

EXAMPLE 76

1-{racemic [(6S,8R, 10R)-6-Tert-butyl-10-(2-methyl-3-methoxyphenyl)-2-chloro-7-oxo-5,6,7,8-tetrahydro-4H, 10H-9-oxa-6a-aza-cyclohepta[de]naphthalen-8-yl]-acetyl}-piperidine-3-carboxylic acid quantitative yield.

84-MS (APCl): 583 (M+H⁺).

¹H NMR (400 MHz, CDCl₃, diastereomeric mixture) δ 7.27 (m, 1H), 7.19 (m, 1H), 7.12 (s, 1H), 6.89 (d, 1H), 6.40 (s, 1H), 6.08 (d, 1H), 4.78 (t, 1H), 4.50 (m, 1H), 3.86 (s, 3H), 3.36 (m, 1H), 1.90 (s, 3H), 0.92 (s, 9H).

EXAMPLE 77

1-{racemic [(6S,8R,10S)-6-Tert-butyl-10-(benzo[1, 3]dioxol-4-yl)-2-methyl-7-oxo-5,6,7,8-tetrahydro-4H.10H-9-oxa-6a-aza-cyclohepta[de]naphthalen-8-yl]-acetyl}-piperidine-4-carboxylic acid 96% yield.

MS (APCl): 561 (M−H)⁻.

¹H NMR (400 MHz, CDCl₃) δ 7.08 (dd, 1H), 6.92 (m, 2H), 6.83 (t, 1H), 6.38 (d, 1H), 6.13 (s, 1H), 5.88 (d, 2H), 4.75 (m, 1H), 4.48 (q, 1H), 4.33 (dd, 1H), 3.91 (m, 1H), 3.09 (m, 2H), 2.80 (m, 2H), 2.63 (m, 1H), 2.52 (m, 2H), 2.30 (m, 1H), 2.18 (s, 3H), 1.92 (br m, 2H), 1.70 (m, 3H), 0.89 (s, 9H).

EXAMPLE 78

1-{racemic [(6S,8R,10S)-6-Tert-butyl-10-(benzo[1,3]dioxol-4-yl)-2-methyl-7-oxo-5,6,7,8-tetrahydro-4H, 10H-9-oxa-6a-aza-cyclohepta[de]naphthalen-8-yl]-acetyl}-piperidine-3-carboxylic acid 90% yield.

MS (APCl): 561 (M−H)⁻.

¹H NMR (400 MHz, CDCl₃, diastereomeric mixture) δ 7.06 (t, 1H), 6.91 (m, 2H), 6.82 (d, 1H), 6.37 (d, 1H), 6.11 (d, 1H), 5.86 (d, 2H), 4.73 (t, 1H), 4.46 (q, 1H), 2.17 (s, 3H), 0.87 (s, 9H).

EXAMPLE 79 racemic 1-{[(6S,8S,10S)-6-Tert-butyl-10-(2-chloro-3,4-dimethoxyphenyl)-2-chloro-7-oxo-5,6,7,8-tetrahydro-4H,10H-9-oxa-6a-aza-cyclohepta[de]naphthalen-8-yl]-acetyl}-piperidine-4-carboxylic acid 96% yield.

MS (PCl): 634 (M+H⁺).

¹H NMR (400 MHz, CDCl₃) δ 7.13 (m, 2H), 7.09 (d, 1H), 6.75 (d, 1H), 6.35 (d, 1H), 4.88 (m, 2H), 4.33 (d, 1H), 3.92 (d, 1H), 3.83 (s, 3H), 3.82 (d, 3H), 3.13 (m, 2H), 2.86 (m, 2H), 2.68 (m, 1H), 2.53 (m, 2H), 2.22 (m, 1H), 1.94 (m, 2H), 1.84 (m, 1H), 1.68 (m, 2H), 0.71 (d, 9H).

EXAMPLE 80 racemic 1-{[(6S,8R,10S)-6-Tert-butyl-10-(2-chloro-3,4-dimethoxyphenyl)-2-chloro-7-oxo-5,6,7,8-tetrahydro-4H, 10H-9-oxa-6a-aza-cyclohepta[de]naphthalen-8-yl]-acetyl}-piperidine-4-carboxylic acid 72% yield.

MS (APCl): 631 (M−H)⁻.

¹H NMR (400 MHz, CDCl₃) δ 7.36 (t, 1H), 7.12 (s, 1H), 6.93 (m, 1H), 6.33 (m, 1H), 6.17 (s, 1H), 4.75 (m, 1H), 4.44 (q, 1H), 4.33 (dd, 1H), 3.90 (d, 3H), 3.83 (s, 3H), 3.12 (m, 1H), 3.00 (m, 1H), 2.78 (m, 2H), 2.67 (m, 1H), 2.52 (m, 2H), 2.30 (m, 1H), 2.13 (s, 1H), 1.90–1.60 (m, 5H), 0.90 (s, 9H).

EXAMPLE 81

1-{[racemic (6S,8S,10S)-6-Tert-butyl-10-(2-chloro-3,4-dimethoxyphenyl)-2-chloro-7-oxo-5,6,7,8-tetrahydro-4H,10H-9-oxa-6a-aza-cyclohepta[de]naphthalen-8-yl]-acetyl}-piperidine-3-carboxylic acid 98% yield.

MS (APCl): 631 (M− H)⁻.

¹H NMR (400 MHz, CDCl₃, diastereomeric mixture) δ 7.24 (m, 1H), 7.10 (m, 2H), 6.73 (d, 1H), 6.33 (m, 1H), 4.87 (m, 2H), 3.82 and 3.81 (2s, 6H), 0.69 (s, 9H).

EXAMPLE 82

1-{[racemic (6S,8R,10S)-6-Tert-Butyl-10-(2-chloro-3,4-dimethoxyphenyl)-2-chloro-7-oxo-5,6,7,8-tetrahydro-4H ,10H-9-oxa-6a-aza-cyclohepta[de]naphthalen-8-yl]-acetyl}-piperidine-3-carboxylic acid 62% yield.

MS (APCl): 631 (M−H)⁻.

¹H NMR (400 MHz, CDCl₃, diastereomeric mixture) δ 7.39 (t, 1H), 7.13 (s, 1H), 6.96 (m, 1H), 6.37 (s, 1H), 6.19 (m, 1H), 4.78 (t, 1H), 3.92 (s, 3H), 3.85 (s, 3H), 0.92 (s, 9H).

EXAMPLE 83

1-{racemic [(6S,8R,10S)-6-Tert-butyl-10-(2-chloro-3,4-dimethoxyphenyl)-2-methyl-7-oxo-5,6,7,8-tetrahydro-4H 10H-9-oxa-6a-aza-cyclohepta[de]naphthalen-8-yl]-acetyl}-piperidine-4-carboxylic acid 97% yield.

MS (APCl): 611 (M−H)⁻.

¹H NMR (400 MHz, CDCl₃, rotameric mixture) δ 7.36 (dd, 1H), 6.90 (m, 2H), 6.18 (s, 1H), 6.11 (s, 1H), 4.72 (m, 1H), 4.44 (q, 1H), 4.35 (dd, 1H), 3.90 (m, 1H), 3.81 (d, 3H), 3.40 (d, 3H), 3.10 (m, 1H), 2.93 (m, 1H), 2.80 (dd, 1H), 2.75 (m, 1H), 2.60 (m, 1H), 2.69 (m, 2H), 2.28 (m, 1H), 2.11 (s, 3H), 1.89 (m, 2H), 1.80–1.50 (m, 3H), 0.90 (s, 9H).

EXAMPLE 84

1-{racemic [(6S,8R,10S)-6-Tert-butyl-10-(2-chloro-3,4-dimethoxyphenyl)-2-methyl-7-oxo-5,6,7,8-tetrahydro-4H, 10H-9-oxa-6a-aza-cyclohepta[de]naphthalen-8-yl]-acetyl}-piperidine-3-carboxylic acid 98% yield.

MS (APCl): 611 (M−H)⁻.

¹H NMR (400 MHz, CDCl₃, diastereomeric mixture) δ 7.39 (d, 1H), 6.93 (m, 1H), 6.92 (s, 1H), 6.20 (m, 1H), 6.13 (s, 1H), 4.73 (t, 1H), 4.58 (dd, 1H), 3.90 (s, 3H), 3.83 (s, 3H), 2.13 (s, 3H), 0.91 (s, 9H).

EXAMPLE 85

1-{racemic [(6S,8R, 10S)-6-Tert-butyl-10-(2-methoxyphenyl)-2-chloro-7-oxo-5,6,7,8-tetrahydro-4H, 10H-9-thia-6a-aza-cyclohepta[de]naphthalen-8-yl]-acetyl}-piperidine-4-carboxylic acid 95% yield.

MS (APCl): 585 (M+H⁺).

¹H NMR (400 MHz, CDCl₃) δ 7.73 (d, 1H), 7.34 (t, 1H), 7.08 (br s, 2H), 6.90 (d, 1H), 6.61 (s, 1H), 6.29 (s, 1H), 4.71 (m, 1H), 4.27 (dd, 1H), 3.80 (m, 1H), 3.67 (s, 3H), 3.15 (m, 2H), 2.80 (m, 2H), 0.96 (s, 9H).

EXAMPLE 86

(3R)-1-{racemic [(1R,7S,9R)-1-Tert-butyl-7-(2,3-dimethoxy-phenyl)-5-methyl-10-oxo-1 ,2,9,10-tetrahydro-7H-3,8-dioxa-10a-aza-cyclohepta[de]naphthalen-9-yl]-acetyl}-piperidine-3-carboxylic acid 99% yield.

MS (APCl): 581 (M+H⁺).

¹H NMR (400 MHz, CDCl₃, diastereomeric mixture) δ 7.26–7.16 (m, 2H), 6.92 (d, 1H), 6.60 (s, 1H), 6.08 (m, 1H), 5.98 (s, 1H), 4.80 (m, 1H), 4.60 (d, 1H), 4.48 (s, 1H), 4.26 (m, 1H), 3.84 (s, 3H), 3.50 (s, 3H), 2.10 (s, 3H), 1.03 (s, 9H).

EXAMPLE 87

1-{racemic [(1R,7S,9R)-1-Tert-butyl-7-(2,3-dihydro-benzo[1,4]dioxin-5-yl)-5-methyl-10-oxo-1,2,9,10-tetrahydro-7H-3,8-dioxa-10a-aza-cyclohepta[de]naphthalen-9-yl]-acetyl}-piperidine-4-carboxylic acid 77% yield.

MS (APCl): 579 (M+H⁺).

¹H NMR (400 MHz, CDCl₃) δ 7.18 (m, 1H), 6.91 (t, 1H), 6.88 (m, 1H), 6.61 (s, 1H), 6.06 (m, 1H), 6.00 (s, 1H), 4.78 (m, 1H), 4.60 (d, 1H), 4.48 (m, 1H), 4.32–3.92 (m, 6H), 3.12 (m, 2H), 2.80 (m, 2H), 2.53 (m, 1H), 2.12 (s, 3H), 1.92 (m, 2H), 1.70 (m, 2H), 1.00 (s, 9H).

EXAMPLE 88

1-{racemic [(1R,7S,9R)-1-Tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid 92% yield.

MS (APCl): 581 (M+H⁺).

¹H NMR (400 MHz, CDCl₃, diastereomeric mixture) δ 7.24–7.16 (m, 2H), 6.93 (d, 1H), 6.61 (s, 1H), 6.10 (s, 1H), 5.99 (s, 1H), 4.80 (br s, 1H), 4.62 (d, 1H), 4.49 (br s, 1H), 4.24 (br d, 1H), 3.84 (s, 3H), 3.49 (s, 3H), 2.10 (s, 3H), 1.03 (s, 9H).

EXAMPLE 89

1-{racemic [(1R,7S,9R)-1-Tert-butyl-7-(2,3-dihydro-benzo[1,4]dioxin-5-yl)-5-methyl-10-oxo-1,2,9,10-tetrahydro-7H-3,8-dioxa-10a-aza-cyclohepta[de]naphthalen-9-yl]-acetyl}-piperidine-3-carboxylic acid 86% yield.

MS (APCl): 579 (M+H⁺).

¹H NMR (400 MHz, CDCl₃, diastereomeric mixture) δ 7.19 (m, 1H), 6.92 (m, 1H), 6.88 (d, 1H), 6.62 (s, 1H), 6.07 (s, 1H), 6.00 (d, 1H), 4.80 (m, 1H), 4.61 (d, 1H), 4.48 (m, 1H), 3.40 (ddd, 1H), 2.11 (s, 3H), 1.02 (s, 9H).

EXAMPLE 90

1-{racemic [(1R,7S,9R)-1-Tert-butyl-7-(2-chloro-3,4-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid 87% yield.

MS (APCl): 615 (M+H⁺).

¹H NMR (400 MHz, CDCl₃) δ 7.44 (t, 1H), 6.95 (m, 1H), 6.66 (s, 1H), 6.02 (s, 1H), 5.89 (s, 1H), 4.82 (m, 1H), 4.62 (d, 1H), 4.50 (m, 1H), 4.35 (dd, 1H), 4.23 (br d, 1H), 3.93 (d, 3H), 3.82 (s, 3H), 3.12 (m, 2H), 2.85 (m, 2H), 2.56 (m, 1H), 2.10 (s, 3H), 1.93 (m, 2H), 1.79–1.66 (m, 2H), 1.02 (s, 9H).

EXAMPLE 91

1-{racemic [(1R,7S,9R)-1-Tert-butyl-7-(2-chlorophenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid quantitative yield.

MS (APCl): 555 (M+H⁺).

¹H NMR (400 MHz, CDCl₃) δ 7.74 (t, 1H), 7.34 (m, 3H), 6.66 (s, 1H), 6.09 (s, 1H), 5.85 (s, 1H), 4.84 (br s, 1H), 4.62 (d, 1H), 4.49 (br s, 1H), 4.33 (dd, 1H), 4.24 (dd, 1H), 3.92 (br d, 1H), 3.13 (m, 2H), 2.83 (m, 2H), 2.54 (br s, 1H), 2.09 (s, 3H), 1.93 (m, 2H), 1.65 (s, 2H), 1.03 (s, 9H).

EXAMPLE 92

1-{racemic [(1R,7S,9R)-1-Tert-butyl-7-(2-chlorophenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid 96% yield.

MS (APCl): 555 (M+H⁺).

¹H NMR (400 MHz, CDCl₃, diastereomeric mixture) δ 7.74 (t, 1H), 7.34 (m, 3H), 6.68 (s, 1H), 6.08 (br s, 1H), 5.88 (s, 1H), 4.86 (m, 1H), 4.63 (d, 1H), 4.49 (br s, 1H), 4.24 (d, 1H), 2.10 (s, 3H), 1.03 (s, 9H).

EXAMPLE 93

1-{racemic [(1R,7R,9R)-1-Tert-butyl-7-(2-trifluoromethylphenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid quantitative yield.

MS (APCl): 589 (M+H⁺).

¹H NMR (400 MHz, CDCl₃) δ 7.95 (d, 1H), 7.68 (m, 2H), 7.49 (m, 1H), 6.64 (s, 1H), 6.15 (s, 1H), 5.77 (br s, 1H), 4.90 (br s, 1H), 4.62 (d, 1H), 4.50 (br s, 1H), 4.34 (dd, 1H), 4.20 (dd, 1H), 3.90 (br s, 1H), 3.09 (m, 2H), 2.83 (m, 2H), 2.54 (br s, 1H), 2.08 (s, 3H), 1.92 (m, 2H), 1.67 (m, 2H), 1.00 (s, 9H).

EXAMPLE 94

1-{racemic [(1R,7R,9R)-1-Tert-Butyl-7-(2-trifluoromethylphenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid 94% yield.

MS (APCl): 589 (M+H⁺).

¹H NMR (400 MHz, CDCl₃, diastereomeric mixture) δ 7.96 (br s, 1H), 7.68 (br d, 2H), 7.51 (t, 1H), 6.64 (s, 1H), 6.15 (s, 1H), 5.78 (s, 1H), 4.90 (br s, 1H), 4.62 (d, 1H), 4.50 (br s, 1H), 4.20 (br d, 1H), 2.08 (s, 3H), 1.00 (s, 9H).

EXAMPLE 95

1-{racemic [(1R,7S,9R)-1-Tert-butyl-7-(2-chloro-3,4-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid 86% yield.

MS (APCl): 615 (M+H⁺).

¹H NMR (400 MHz, CDCl₃, diastereomeric mixture) δ 7.44 (t, 1H), 6.95 (d, 1H), 6.63 (s, 1H), 6.00 (s, 1H), 5.89 (s, 1H), 4.81 (m, 1H), 4.62 (d, 1H), 4.49 (s, 1H), 4.23 (d, 1H), 3.92 (s, 3H), 3.82 (s, 3H), 2.10 (s, 3H), 1.02 (s, 9H).

EXAMPLE 96

1-{racemic [(1R,7R,9R)-1-Tert-butyl-7-(3-methoxyphenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid quantitative yield.

MS (APCl): 551 (M+H⁺).

¹H NMR (400 MHz, CDCl₃) δ 7.30 (t, 1H), 6.95 (s, 1H), 6.90 (m, 2H), 6.63 (s, 1H), 5.99 (d, 1H), 5.72 (s, 1H), 4.85 (br s, 1H), 4.61 (d, 1H), 4.50 (br s, 1H), 4.31 (dd, 1H), 4.22 (br d, 1H), 3.90 (br d, 1H), 3.83 (s, 3H), 3.13 (m, 2H), 2.82 (m, 2H), 2.55 (m, 1H), 2.10 (s, 3H), 1.93 (br s, 2H), 1.62 (s, 2H), 1.00 (s, 9H).

EXAMPLE 97

1-{racemic [(1R,7R,9R)-1-Tert-butyl-7-(3-methoxyphenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid 86% yield.

MS (APCl): 551 (M+H⁺).

¹H NMR (400 MHz, CDCl₃, diastereomeric and rotameric mixture) δ 7.30 (t, 1 H), 6.96 (br s, 1H), 6.90 (m, 2H), 6.63 (s, 1H), 5.99 (s, 1H), 5.72 (s, 1H), 4.84 (br s, 1H), 4.60 (d, 1H), 4.49 (br s, 1H), 3.83 (br s, 3H), 2.10, 2.09 and 2.08 (3s, 3H), 1.00 (s, 9H).

EXAMPLE 98

1-{racemic [(1R,7S,9R)-1-Tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-3-yl-acetic acid MS (APCl): 595 (M+H⁺). ¹H NMR (400 MHz, CDCl₃, diastereomeric mixture) δ 7.18 (m, 1H), 6.93 (d, 1H), 6.61 (m, 1H), 6.10 (m, 1H), 6.00 (br s, 1H), 4.83 (m, 1H), 4.61 (d, 1H), 4.46 (dd, 1H), 4.21 (m, 1H), 3.87 (s, 3H), 3.50 (s, 3H), 2.10 (s, 3H), 1.02 (s, 9H).

EXAMPLE 99

1-{racemic [(1R,7S,9R)-1-Tert-butyl-7-(2,3-dihydro-benzo[1,4]dioxin-5-yl)-5-chloro-10-oxo-1,2,9,10-tetrahydro-7H-3,8-dioxa-10a-aza-cyclohepta[de]naphthalen-9-yl]-acetyl}-piperidine-4-carboxylic acid 80% yield.

MS (APCl): 599 (M+H⁺).

¹H NMR (400 MHz, CDCl₃) δ 7.16 (t, 1H), 6.95 (t, 1H), 6.89 (d, 1H), 6.83 (s, 1H), 6.26 (s, 1H), 5.99 (s, 1H), 4.77 (m, 1H), 4.65 (d, 1H), 4.50 (m, 1H), 4.28 (m, 2H), 4.18 (s, 2H), 4.02 (m, 2H), 3.90 (br d, 1H), 3.17 (m, 2H), 2.87 (q, 1H), 2.80 (d, 1 H), 2.56 (m, 1H), 1.93 (m, 2H), 1.65 (m, 2H), 1.00 (s, 9H).

EXAMPLE 100

1-{racemic [(1R,7S,9R)-1-Tert-butyl-7-(2,3-dimethoxyphenyl)-5-chloro-10-oxo-1,2,9,10-tetrahydro-7H-3,8-dioxa-10a-aza-cyclohepta[de]naphthalen-9-yl]-acetyl}-piperidine-4-carboxylic acid 96% yield.

MS (APCl): 601 (M+H⁺).

¹H NMR (400 MHz, CDCl₃) δ 7.18 (m, 2H), 6.95 (d, 1H), 6.82 (s, 1H), 6.19 (s, 1H), 6.08 (s, 1H), 4.79 (br s, 1H), 4.66 (d, 1H), 4.51 (s, 1H), 4.35 (d, 1H), 4.28 (br d, 1H), 3.89 (s, 3H), 3.51 (s, 3H), 1.02 (s, 9H).

EXAMPLE 101

1-{racemic [(1R,7S,9R)-1-Tert-butyl-7-(benzo[1,3]dioxol-4-yl)-5-chloro-10-oxo-1,2,9,10-tetrahydro-7H-3,8-dioxa-10a-aza-cyclohepta[de]naphthalen-9-yl]-acetyl}-piperidine-4-carboxylic acid 85% yield.

MS (APCl): 585 (M+H⁺).

¹H NMR (400 MHz, CDCl₃) δ 7.08 (t, 1H), 6.92 (t, 1H), 6.84 (m, 2H), 6.33 (d, 1H), 5.89 (s, 2H), 5.86 (s, 1H), 4.81 (m, 1H), 4.64 (d, 1H), 4.51 (m, 1H), 4.34 (d, 1H), 4.24 (dd, 1H), 3.89 (m, 1H), 3.15 (m, 2H), 2.86 (m, 1H), 2.78 (m, 1H), 2.55 (m, 1H), 1.93 (br s, 2H), 1.62 (m, 2H), 0.99 (s, 9H).

EXAMPLE 102

1-{racemic [(1R,7S,9R)-1-Tert-butyl-7-(2,3-dimethoxyphenyl)-5-chloro-10-oxo-1,2,9,10-tetrahydro-7H-3,8-dioxa-10a-aza-cyclohepta[de]naphthalen-9-yl]-acetyl}-piperidine-3-carboxylic acid 94% yield.

MS (APCl): 601 (M+H⁺).

¹H NMR (400 MHz, CDCl₃, diastereomeric mixture) δ 7.20 (m, 2H), 6.94 (d, 1H), 6.82 (s, 1H), 6.19 (s, 1H), 6.08 (d, 1H), 4.79 (m, 1H), 4.64 (d, 1H), 4.51 (s, 1H), 3.86 (s, 3H), 3.52 (s, 3H), 1.03 (s, 9H).

EXAMPLE 103

1-{racemic [(1R,7S,9R)-1-Tert-butyl-7-(benzo[1,3]dioxol-4-yl)-5-chloro-10-oxo-1,2,9,10-tetrahydro-7H-3,8-dioxa-10a-aza-cyclohepta[de]naphthalen-9-yl]-acetyl}-piperidine-3-carboxylic acid quantitative yield.

MS (APCl): 585 (M+H⁺).

¹H NMR (400 MHz, CDCl₃, diastereomeric mixture) δ 7.08 (m, 1H), 6.93 (t, 1H), 6.86 (m, 2H), 6.34 (s, 1H), 5.90 (s, 2H), 5.88 (s,1H), 4.81 (d,1H), 4.65 (d, 1H), 4.50 (s,1H), 1.00 (s, 9H).

EXAMPLE 104

1-{racemic [(1R,7S,9R)-1-Tert-butyl-7-(2-methoxyphenyl)-5-chloro-10-oxo-1,2,9,10-tetrahydro-7H-3,8-dioxa-10a-aza-cyclohepta[de]naphthalen-9-yl]-acetyl}-piperidine-4-carboxylic acid 93% yield.

MS (APCl): 571 (M+H⁺).

¹H NMR (400 MHz, CDCl₃) δ 7.60 (t,1H), 7.33 (br s,1H), 7.08 (m, 1H), 6.83 (m, 2H), 6.17 (s, 1H), 6.06 (d, 1H), 4.77 (m, 1H), 4.65 (dd, 1H), 4.50 (m, 1H), 4.29 (m, 2H), 3.91 (d, 1H), 3.58 (s, 3H), 3.16 (m, 2H), 2.81 (m, 2H), 2.56 (m, 1H), 1.94 (m, 2H), 1.78–1.59 (m, 2H), 1.01 (s, 9H).

EXAMPLE 105

1-{racemic [(1R,7S,9R)-1-Tert-butyl-7-(2-methoxyphenyl)-5-chloro-10-oxo-1,2,9,10-tetrahydro-7H-3,8-dioxa-10a-aza-cyclohepta[de]naphthalen-9-yl]-acetyl}-piperidine-3-carboxylic acid 84% yield.

MS (APCl): 571 (M+H⁺).

¹H NMR (400 MHz, CDCl₃, diastereomeric mixture) δ 7.61 (br s, 1H), 7.33 (t, 1H), 7.08 (t, 1H), 6.84 (d, 1H), 6.82 (s, 1H), 6.17 (s, 1H), 6.08 (d, 1H), 4.78 (m, 1H), 4.64 (d, 1H), 4.50 (s,1H), 4.28 (m,1H), 3.58 (s, 3H), 1.00 (s, 9H).

EXAMPLE 106

1-{racemic [(1R,7S,9R)-1-Tert-butyl-7-(benzo[1,3]dioxol-4-yl)-5-methyl-10-oxo-1,2,9,10-tetrahydro-7H-3,8-dioxa-10a-aza-cyclohepta[de]naphthalen-9-yl]-acetyl}-piperidine-4-carboxylic acid 98% yield.

MS (APCl): 563 (M−H)⁻.

¹H NMR (400 MHz, CDCl₃) δ 7.09 (t, 1H), 6.92 (t, 1H), 6.82 (t, 1H), 6.63 (s, 1H), 6.12 (d, 1H), 5.86 (m, 3H), 4.81 (m, 1H), 4.59 (d, 1H), 4.48 (m, 1H), 4.35 (m, 1H), 4.22 (dd, 1H), 3.90 (m, 1H), 3.12 (m, 2H), 2.80 (m, 2H), 2.51 (m, 1H), 2.13 (s, 3H), 1.90 (m, 2H), 1.57 (m, 2H), 0.98 (s, 9H).

EXAMPLE 107

1-{racemic [(1R,7S,9R)-1-Tert-butyl-7-(benzo[1,3]dioxol-4-yl)-5-methyl-10-oxo-1,2,9,10-tetrahydro-7H-3,8-dioxa-10a-aza-cyclohepta[de]naphthalen-9-yl]-acetyl}-piperidine-3-carboxylic acid 80% yield.

MS (APCl): 563 (M−H)⁻.

¹H NMR (400 MHz, CDCl₃, diastereomeric mixture) δ 7.09 (m, 1H), 6.91 (m, 1H), 6.82 (d, 1H), 6.64 (s, 1H), 6.13 (d, 1H), 5.89 (m, 2H), 5.82 (s, 1H), 4.81 (m, 1H), 4.60 (d, 1H), 4.48 (brs, 1H), 4.22 (m, 1H), 2.13 (s, 3H), 0.97 (s, 9H).

EXAMPLE 108

1-{racemic [(1R,7S,9R)-1-Tert-butyl-7-(2-methoxyphenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid 59% yield.

¹H NMR (400 MHz, CDCl₃) δ 7.62 (dd, 1H), 7.32 (m, 1H), 7.08 (t, 1H), 6.83 (d, 1H), 6.59 (s, 1H), 6.08 (s, 1H), 5.96 (d, 1H), 4.79 (m, 1H), 4.60 (d, 1H), 4.48 (m, 1H), 4.32 (dd, 1H), 4.24 (dd, 1H), 3.92 (br d, 1H), 3.56 (s, 3H), 3.13 (m, 2H), 2.81 (m, 2H), 2.53 (m, 1H), 2.09 (s, 3H), 1.92 (br s, 2H), 1.66 (m, 2H), 1.01 (s, 9H).

EXAMPLE 109

1-{racemic [(1R,7S,9R)-1-Tert-butyl-7-(2-methoxyphenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid 92% yield.

¹H NMR (400 MHz, CDCl₃, diastereomeric mixture) δ 7.62 (br s, 1H), 7.32 (m, 1H), 7.17 (d, 1H), 7.07 (t, 1H), 6.83 (d, 1H), 6.60 (s, 1H), 6.08 (s, 1H), 5.98 (s, 1H), 4.78 (br s, 1H), 4.60 (d, 1H), 4.49 (br s, 1H), 4.26 (br d, 1H), 3.57 (s, 3H), 2.09 (s, 3H), 1.01 (s, 9H).

EXAMPLE 110 racemic 1-{(1R,7S,9R)-[1-Methyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid 60% yield.

MS (APCl): 539 (M+H⁺).

¹H NMR (400 MHz, CDCl₃, rotameric mixture) δ 7.08 (m, 2H), 6.90 (m, 1H), 6.68 (s, 1H), 6.00 (m, 2H), 5.08 (br s, 1H), 4.76 (m, 1H), 4.32 (dd, 1H), 4.27 (d, 1H), 4.15 (d, 1H), 3.90 (m, 1H), 3.84 (s, 3H), 3.43 (s, 3H), 3.11 (m, 2H), 2.79 (m, 2H), 2.54 (m, 1H), 2.11 (s, 3H), 1.91 (m, 2H), 1.69 (m, 2H), 1.29 (d, 3H).

EXAMPLE 111

(2R)-{2-[(1R,7S,9R)-1-Tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-propionic acid 75% yield.

MS (APCl): 541 (M+H⁺).

¹H NMR (400 MHz, CDCl₃) δ 7.18 (m, 1H), 6.95 (d, 1H), 6.72 (d, 1H), 6.62 (s, 1H), 6.10 (s, 1H), 6.00 (s, 1H), 4.67–4.49 (m, 4H), 4.19 (dd, 1H), 3.86 (s, 3H), 3.50 (s, 3H), 2.98 (dd, 1H), 2.75 (dd, 1H), 2.11 (s, 3H), 1.43 (d, 3H), 1.02 (s, 9H).

EXAMPLE 112

(2R)-{2-[(1S,7R,9S)-1-Tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-propionic acid 60% yield.

MS (APCl): 541 (M+H⁺).

¹H NMR (400 MHz, CDCl₃, rotameric mixture) δ 7.18 (m, 1H), 6.94 (d, 1H), 6.66 (d, 1H), 6.62 (s, 1H), 6.11 (s, 1H), 6.02 (s, 1H), 4.65 (m, 2H), 4.52 (m, 2H), 4.17 (dd, 1H), 3.86 (s, 3H), 3.50 (s, 3H), 2.90 (dd, 1H), 2.80 (dd, 1H), 2.11 (s, 3H), 1.43 (d, 3H), 1.02 (s, 9H).

EXAMPLE 113

(3R)-1-{[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid 90% yield.

MS (APCl): 581 (M+H⁺).

¹H NMR (400 MHz, CDCl₃, rotameric mixture) δ 7.20 (m, 2H), 6.93 (d, 1H), 6.60 (s, 1H), 6.09 (d, 1H), 5.99 (s, 1H), 4.80 (dd, 1H), 4.61 (d, 1H), 3.86 (s, 3H), 3.50 and 3.49 (2s, 3H), 2.09 (s, 3H), 1.03 (s, 9H).

$[\alpha]_D^{20}$ −176 (c 0.0104, CHCl₃)

EXAMPLE 114

{2-[(1R,7S,9R)-1-Tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-acetic acid Quantitative Yield MS (APCl): 527 (M+H⁺).

¹H NMR (400 MHz, CDCl₃) δ 7.61 (ddd, 1H), 7.19 (m, 1H), 6.94 (d, 1H), 6.73 (br s, 1H), 6.62 (s, 1H), 6.10 (s, 1H), 6.01 (s, 1H), 4.68 (br s, 1H), 4.61 (d, 1H), 4.50 (s, 1H), 3.86 (s, 3H), 3.50 (s, 3H), 2.11 (s, 3H), 1.02 (s, 9H).

EXAMPLE 115

2R-{racemic 2-[(1R,7S,9R)-1-Tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-propionic acid MS (APCl): 541 (M+H⁺).

¹H NMR (400 MHz, CDCl₃, diastereomeric mixture) δ 6.64 (s, 1H), 6.10 (s, 1H), 3.86 (2s, 3H), 3.50 (2s, 3H), 2.11 (s, 3H), 1.45 (d, 3H), 1.02 (s, 9H).

EXAMPLE 116

2S-{racemic 2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-succinic acid MS (APCl): 585 (M+H⁺).

¹H NMR (400 MHz, CDCl₃, diastereomeric mixture) δ 6.64 (s, 1H), 6.07 (d, 1H), 6.02 (s, 1H), 3.84 (2s, 3H), 3.48 and 3.47 (2s, 3H), 2.11 (s, 3H), 1.00 and 0.99 (2s, 9H).

EXAMPLE 117

(2S,3S)-2-{racemic 2-[(1R,7S,9R)-1-tert-butyl-7-(2, 3-dimethoxyphenyl)-5-methyl-10-oxo-1,2,9,10-tetrahydro-7H-3,8-dioxa-10a-aza-cyclohepta[de] naphthalen-9-yl]-acetylamino}-3-methyl-pentanoic acid MS (APCl): 583 (M+H⁺).

¹H NMR (400 MHz, CDCl₃, diastereomeric mixture) δ 6.95 (d, 1H), 6.64 (s, 1H), 3.86 (s, 3H), 3.49 (2s, 3H), 2.12 (s, 3H), 1.02 (s, 9H).

EXAMPLE 118 racemic (1R,7S,9R)-1-Tert-butyl-7-(2,3-dimethoxyphenyl)-5-methyl-9-[2-(3-methylamino-pyrrolidin-1-yl)-2-oxo-ethyl]-1,2-dihydro-7H-3,8-dioxa-10a-aza-10 cyclohepta[de]naphthalen-10-one MS (APCl): 552 (M+H⁺).

¹H NMR (400 MHz, CDCl₃, diastereomeric mixture) δ 6.95 (d, 1H), 6.64 (s, 1H), 3.86 (s, 3H), 3.50 and 3.49 (2s, 3H), 2.11 (s, 3H), 1.00 (s, 9H).

EXAMPLE 119

2R-{racemic 2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de] naphthalen-9-yl]-acetylamino}-4-methyl-pentanoic acid MS (APCl): 583 (M+H⁺).

¹H NMR (400 MHz, CDCl₃, diastereomeric mixture) δ 6.96 (d, 1H), 6.64 (s, 20 1H), 6.09 (d, 1H), 6.03 (s, 1H), 3.86 (s, 3H), 3.49 (2s, 3H), 2.12 (s, 3H), 1.02 (s, 9H).

EXAMPLE 120

2S-{racemic 2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-succinic acid 1-methyl ester MS (APCl): 599 (M+H⁺).

¹H NMR (400 MHz, CDCl₃, diastereomeric mixture) δ 7.58 (m, 1H), 6.63 (s, 1H), 6.10 (s, 1H), 6.02 (d, 1H), 3.86 (2s, 3H), 3.71 and 3.67 (2s, 3H), 3.50 and 3.48 (2s, 3H), 2.11 (s, 3H), 1.02 and 1.00 (2s, 9H).

EXAMPLE 121

2S-{racemic 2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de] naphthalen-9-yl]-acetylamino}-pentanedioic acid 1-methyl ester MS (APCl): 613 (M+H⁺).

¹H NMR (400 MHz, CDCl₃, diastereomeric mixture) δ 6.10 (d, 1H), 6.02 (s, 1H), 3.86 (2s, 3H), 3.71 and 3.69 (2s, 3H), 3.51 and 3.50 (2s, 3H), 2.11 (s, 3H), 1.02 and 1.01 (2s, 9H).

EXAMPLE 122

(S)-{racemic 2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de] naphthalen-9-yl]-acetylamino}-phenyl-acetic acid MS (APCl): 603 (M+H⁺).

¹H NMR (400 MHz, CDCl₃, diastereomeric mixture) δ 6.62 (s, 1H), 6.08 (d, 1H), 6.00 (d, 1H), 5.57 (dd, 1H), 3.86 (s, 3H), 3.48 and 3.47 (2s, 3H), 2.11 (s, 3H), 1.01 (s, 9H).

EXAMPLE 123 racemic (1R,7S,9R)-9-[2-(3-amino-pyrrolidin-1-yl)-2-oxo-ethyl]-1-tert-butyl-7-(2,3-dimethoxyphenyl)-5-methyl-1,2-dihydro-7H-3,8-dioxa-10a-aza-cyclohepta[de]naphthalen-10-one MS (APCl): 638 (M+H +).

¹H NMR (400 MHz, CDCl₃, diastereomeric mixture) δ 6.64 (s, 1H), 6.03 (m, 2H), 3.86 (2s, 3H), 3.50 (s, 3H), 2.10 (s, 3H), 1.00 (2s, 9H).

EXAMPLE 124

2S-{racemic 2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de] naphthalen-9-yl]-acetylamino}-3-phenyl-propionic acid MS (APCl): 615 (M−H)⁻.

¹H NMR (400 MHz, CDCl₃, diastereomeric mixture) δ 6.64 (s, 1H), 6.05 (s, 1H), 6.00 (s, 1H), 3.86 and 3.85 (2s, 3H), 3.48 (2s, 3H), 2.12 and 2.11 (2s, 3H), 1.00 and 0.99 (2s, 9H).

EXAMPLE 125

(2R)-1-{racemic [(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de] naphthalen-9-yl]-acetyl}-pyrrolidine-2-carboxylic acid MS (APCl): 565 (M−H)⁻.

¹H NMR (400 MHz, CDCl₃, diastereomeric mixture) δ 6.64 (s, 1H), 6.09 (d, 1H), 5.99 (d, 1H), 3.86 (2s, 3H), 3.50 (2s, 3H), 2.11 (s, 3H), 1.02 (s, 9H).

EXAMPLE 126 racemic N-(2-amino-ethyl)-2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetamide MS (APCl): 512 (M+H⁺).

1H NMR (400 MHz, CDCl₃) δ 6.66 (s, 1H), 6.09 (s, 1H), 6.04 (s, 1H), 3.87 (s, 3H), 3.49 (s, 3H), 2.12 (s, 3H), 0.98 (s, 9H).

EXAMPLE 127

2-{racemic 2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de] naphthalen-9-yl]-acetylamino}-3-(4-hydroxyphenyl)-propionic acid MS (APCl): 633 (M+H⁺).

¹H NMR (400 MHz, CDCl₃, diastereomeric mixture) δ 3.87 and 3.85 (2s, 3H), 3.46 and 3.45 (2s, 3H), 2.12 and 2.11 (2s, 3H), 1.02 and 0.98 (2s, 9H).

EXAMPLE 128 racemic 3-{2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de] naphthalen-9-yl]-acetylamino}-propionic acid MS (APCl): 540 (M+H⁺).

¹H NMR (400 MHz, CDCl₃) δ 6.64 (s, 1H), 6.08 (s, 1H), 6.02 (s, 1H), 3.86 (s, 3H), 3.48 (s, 3H), 2.11 (s, 3H), 1.01 (s, 9H).

EXAMPLE 129

2-{racemic 2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-4-hydroxy-butyric acid MS (APCl): 617 (M+CH₃CN)+.

¹H NMR (400 MHz, CDCl₃, diastereomeric mixture) δ 6.62 (s, 2H), 6.05 (s, 1H), 6.00 (s, 1H), 3.86 and 3.85 (2s, 3H), 3.48 and 3.47 (2s, 3H), 2.11 and 2.10 (2s, 3H), 1.00 and 0.98 (2s, 9H).

EXAMPLE 130 racemic ({[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-methyl-amino)-acetic acid MS (APCl): 541 (M+H⁺).

¹H NMR (400 MHz, CDCl₃) δ 6.62 (s, 1H), 6.09 (s, 1H), 6.00 (s, 1H), 3.86 (s, 3H), 3.49 (s, 3H), 3.18 (s, 3H), 2.10 (s, 3H), 1.02 (s, 9H).

EXAMPLE 131 racemic 9-[2-(4-Benzo[1,3]dioxol-5-ylmethyl-piperazin-1-yl)-2-oxo-ethyl]-1-tert-butyl-7-(2,3-dimethoxyphenyl)-5-methyl-1,2-dihydro-7H-3,8-dioxa-10a-aza-cyclohepta[de]naphthalen-10-one MS (APCl): 672 (M+H⁺).

¹H NMR (400 MHz, CDCl₃) δ 6.09 (s, 1H), 5.98 (s, 1H), 5.93 (s, 2H), 3.86 (s, 3H), 3.48 (s, 3H), 2.09 (s, 3H), 1.02 (s, 9H).

EXAMPLE 132

{[3-({racemic [(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-methyl-amino)-propyl]-methyl-amino}-phenyl-acetic acid MS (APCl): 688 (M+H⁺).

¹H NMR (400 MHz, CDCl₃, diastereomeric mixture) δ 6.61 (s, 1H), 6.08 (s, 1H), 6.00 (m, 1H), 3.86 (s, 3H), 3.49 (s, 3H), 3.02 (s, 3H), 2.10 (s, 3H), 1.02 (s, 9H).

EXAMPLE 133 a racemic 2-{[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-piperidin-4-ylmethyl)-malonic acid MS (APCl): 651 (M−H)⁻.

¹H NMR (400 MHz, CDCl₃) δ 6.60 (s,1H), 6.07 (d,1H), 5.98 (d,1H), 3.85 (s, 3H), 3.48 (s, 3H), 2.09 (s, 3H), 1.02 (s, 9H).

EXAMPLE 134 racemic 1-{2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-cyclopropanecarboxylic acid ¹H NMR (400 MHz, CDCl₃) δ 7.17 (t, 1H), 6.94 (d, 1H), 6.70 (s, 1H), 6.61 (s, 1H), 6.08 (s,1H), 6.00 (s,1H), 4.68 (m,1H), 4.59 (d,1H), 4.48 (d,1H), 4.16 (dd, 1H), 3.86 (s, 1H), 3.49 (s, 3H), 2.91 (dd, 1H), 2.68 (dd, 1H), 2.10 (s, 3H), 1.65 (m, 1H), 1.53 (m, 1H), 1.14 (m, 2H), 1.01 (s, 9H).

EXAMPLE 135 racemic 4-[5-({2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-methyl)-thiophen-2-yl]-butyric acid MS (APCl): 651 (M+H⁺).

¹H NMR (400 MHz, CDCl₃) δ 6.73 (d, 1H), 6.60 (app d, 2H), 6.29 (br s, 1H), 6.08 (s, 1H), 5.98 (s, 1H), 3.85 (s, 3H), 3.48 (s, 3H), 2.10 (s, 3H), 1.01 (s, 9H).

EXAMPLE 136 racemic trans-4-({2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-methyl)-cyclohexanecarboxylic acid MS (APCl): 609 (M+H⁺).

¹H NMR (400 MHz, CDCl₃) δ 6.94 (d, 1H), 6.61 (s, 1H), 6.10 (s, 1H), 5.99 (s, 1H), 3.86 and 3.85 (2s, 3H), 3.48 (s, 3H), 2.10 (s, 3H), 1.02 (s, 9H).

EXAMPLE 137

3-{racemic 2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-2-(3-methoxyphenyl)-propionic acid ¹H NMR (400 MHz, CDCl₃, diastereomeric mixture) δ 7.15 (m, 3H), 6.91 (m, 1H), 6.79 (m, 3H), 6.58 (s,1H), 6.40 (m,1H), 6.04 (s,1H), 5.97 (s,1H), 4.66 (m, 1H), 4.55 (d, 1H), 4.45 (d, 1H), 4.12 (m, 1H), 3.83 and 3.82 (2s, 3H), 3.81–3.54 (m, 2H), 3.74 and 3.72 (2s, 3H), 3.45 (s, 3H), 2.84 (m, 1H), 2.62 (m, 1H), 2.08 and 2.04 (2s, 3H), 0.98 and 0.96 (2s, 9H).

EXAMPLE 138 racemic 5-{2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-1H-indole-2-carboxylic acid MS (APCl): 626 (M−H)⁻.

¹H NMR (400 MHz, DMSO-d₆) δ 9.90 (s, 1H), 7.96 (s, 1H), 6.72 (s, 1H), 5.94 (s, 1H), 5.86 (s, 1H), 3.78 (s, 3H), 3.35 (s, 3H), 2.07 (s, 3H), 0.95 (s, 9H).

EXAMPLE 139 racemic 4-{2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-1H-indole-2-carboxylic acid MS (APCl): 626 (M−H)⁻.

¹H NMR (400 MHz, DMSO-d₆) δ 9.84 (s, 1H), 7.43 (s, 1H), 6.72 (s, 1H), 5.95 (s, 1H), 5.88 (s, 1H), 3.78 (s, 3H), 3.36 (s, 3H), 2.07 (s, 3H), 0.96 (s, 9H).

EXAMPLE 140 racemic 6-{2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetylamino}-1H-indole-2-carboxylic acid MS (APCl): 626 (M−H)⁻.

$^1$H NMR (400 MHz, DMSO-d$_6$) δ 10.05 (s, 1H), 7.95 (s, 1H), 6.72 (s, 1H), 5.94 (s, 1H), 5.87 (s, 1H), 3.78 (s, 3H), 3.35 (s, 3H), 2.07 (s, 3H), 0.95 (s, 9H).

EXAMPLE 141

(2S)-1-{racemic [(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-2-carboxylic acid MS (APCl): 579 (M−H)⁻.

$^1$H NMR (400 MHz, CDCl$_3$, diastereomeric mixture) δ 6.61 (s, 1H), 6.09 (m, 1H), 6.00 (s, 1H), 3.86 (2s, 3H), 3.49 (2s, 3H), 2.10 and 2.09 (2s, 3H), 1.03 and 1.02 (2s, 9H).

EXAMPLE 142 racemic N-(6-amino-hexyl)-2-[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetamide MS (APCl): 568 (M+H⁺).

$^1$H NMR (400 MHz, CDCl$_3$) δ 6.61 (s, 1H), 6.07 (s, 1H), 5.99 (s, 1H), 3.86 (2s, 3H), 3.49 (s, 3H), 2.10 (s, 3H), 1.01 (s, 9H).

EXAMPLE 143

(2S)-1-{racemic [(1R,7S,9R)-1-tert-butyl-7-(2,3-dimethoxyphenyl)-5-methyl-10-oxo-1 2,9,10-tetrahydro-7H-3,8-dioxa-10a-aza-cyclohepta[de]naphthalen-9-yl]-acetyl}-azetidine-2-carboxylic acid MS (APCl): 553 (M+H⁺).

$^1$H NMR (400 MHz, CDCl$_3$, diastereomeric mixture) δ 6.62 (s, 1H), 6.10 (s, 1H), 6.01 (s, 1H), 3.86 (2s, 3H), 3.51 (s, 3H), 2.11 (s, 3H), 1.03 (s, 9H).

EXAMPLE 144

1-{racemic [(1R,7S,9R)-1-Tert-butyl-7-(2,3-dihydro-benzo[1,4]dioxin-5-yl)-5-methyl-10-oxo-1,2,9,10-tetrahydro-7H-3-oxa-8-thia-10a-aza-cyclohepta[de]naphthalen-9-yl]-acetyl}-piperidine-4-carboxylic acid 72% yield.

MS (APCl): 595 (M+H⁺).

$^1$H NMR (400 MHz, CDCl$_3$) δ 7.24 (d, 1H), 6.91 (t, 1H), 6.88 (d, 1H), 6.52 (s, 1H), 6.17 (s, 1H), 6.03 (s, 1H), 4.54 (d, 1H), 4.44 (m, 1H), 4.32 (m, 1H), 3.82 (m, 1H), 3.16 (m, 2H), 2.81 (m, 1H), 2.53 (m, 1H), 2.38 (d, 1H), 2.12 (s, 3H), 1.01 (s, 9H).

EXAMPLE 145

1-{racemic [(1R,7S,9R)-1-Tert-butyl-7-(2,3-dihydro-benzo[1,4]dioxin-5-yl)-5-methyl-10-oxo-1 2,9,10-tetrahydro-7H-3-oxa-8-thia-10a-aza-cyclohepta[de]naphthalen-9-yl]-acetyl}-piperidine-3-carboxylic acid 67% yield.

MS (APCl): 595 (M+H⁺).

$^1$H NMR (400 MHz, CDCl$_3$, diastereomeric mixture) δ 7.25 (d, 1H), 6.91 (t, 1H), 6.88 (d, 1H), 6.53 (s, 1H), 6.17 (s, 1H), 6.02 (s, 1H), 4.53 (d, 1H), 2.12 (s, 3H), 1.01 (s, 9H).

EXAMPLE 146

1-{racemic [(1R,7S,9R)-1-Tert-butyl-7-(2,3-dimethoxyphenyl)-5-methyl-10-oxo-1,2,9,10-tetrahydro-7H-3-oxa-8-thia-10a-aza-cyclohepta[de]naphthalen-9-yl]-acetyl}-piperidine-4-carboxylic acid 81% yield.

MS (APCl): 597 (M+H⁺).

$^1$H NMR (400 MHz, CDCl$_3$) δ 7.35 (d, 1H), 7.15 (t, 1H), 6.92 (d, 1H), 6.52 (s, 1H), 6.12 (d, 2H), 4.53 (d, 1H), 4.48 (brs, 1H), 4.31–4.18 (m, 3H), 3.85 (s, 3H), 3.83 (m, 1H), 3.56 (s, 3H), 3.17 (m, 2H), 2.82 (m, 1H), 2.53 (m, 1H), 2.38 (d, 1H), 2.09 (s, 3H), 1.92 (m, 2H), 1.80 (m, 2H), 1.04 (s, 9H).

EXAMPLE 147

1-{racemic [(1R,7S,9R)-1-Tert-butyl-7-(2,3-dimethoxyphenyl)-5-methyl-10-oxo-1,2,9,10-tetrahydro-7H-3-oxa-8-thia-10a-aza-cyclohepta[de]naphthalen-9-yl]-acetyl}-piperidine-3-carboxylic acid quantitative yield.

MS (APCl): 597 (M+H⁺).

$^1$H NMR (400 MHz, CDCl$_3$, diastereomeric mixture) δ 7.36 (d, 1H), 7.15 (t, 1H), 6.93 (d, 1H), 6.52 (s, 1H), 6.11 (d, 2H), 4.53 (d, 1H), 4.46 (s, 1H), 3.85 (s, 3H), 3.56 (s, 3H), 2.09 (s, 3H), 1.04 (s, 9H).

EXAMPLE 148 racemic 1-{(1R,7S,9R)-[1-tert-butyl-7-(3-hydroxy-2-methoxy-phenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid Twenty-five mL of IOWA Medium (anhydrous dextrose, 20 g; yeast extract, 5 g; dipotassium hydrogen phosphate, 5 g; sodium chloride, 5 g; soybean flour, 5 g; distilled water, 1 L; adjusted to pH 7.2 with 1 N sulfuric acid) were added to each of twenty 125-mL Delong flasks with Morton closures and the resulting combinations were steam-sterilized for 30 minutes at 15 psig and 121° C. Each flask was aseptically inoculated with 0.25 mL of a cryogenically stored (−80° C.) axenic stock of *Absidia pseudocylindrospora* (American Type Culture Collection strain 24169) spores. The inoculated flasks were mounted vertically on a rotary shaker (1-inch throw) and shaken at 250 rpm and 28° C. for 2 days. Then, 5 mL of a Tween 80/glycerol solution (Tween 80 [polyoxyethylenesorbitan monooleate], 25 g; glycerol, 100 g; distilled water, 975 mL; sterilized by membrane filtration [0.2 micron porosity]) was added to each of the 20 flasks containing fungal growth in IOWA Medium. Racemic 1-{(1R,7S,9R)-[1-tert-butyl-7-(2,3-dimethoxy-phenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid (i.e., substrate) was dissolved in a 1:1 methanol/dimethylsulfoxide solution (10 mg/mL). To each of the 20 biotransformation flasks, 0.25 mL of the resulting solution was aseptically added to give an initial substrate concentration of 100 mcg/mL. The dosed flasks were remounted vertically on the rotary shaker and shaken at 250 rpm and 28° C. for 1 day. Again, to each of the 20 biotransformation flasks, 0.25 mL of the solution of substrate in methanol/dimethylsulfoxide was aseptically added to give a total added substrate concentration of 200 mcg/mL. The dosed flasks were remounted vertically on the rotary shaker and shaken at 250 rpm and 28° C. for an additional 4 days. At the end of the 5-day biotransformation period, the contents of the biotransformation flasks (i.e., broth) were combined and filtered through a Whatman GF/B filter. Each flask was rinsed with distilled water and this aqueous rinse also was filtered and added to the broth filtrate (approx. 850 mL total volume). The filtrate was extracted 3 times with equal volumes of ethyl acetate. For each extraction, the solvent/aqueous mix was centrifuged at 10,000 rpm for 10 min. and the supernatant solvent layer was retained. The 3 ethyl acetate extracts were pooled and taken to dryness under reduced pressure at 45° C. The solids retained on the GF/B filter were extracted with 300 mL methanol. The methanol extract was separated from the extracted solids by filtering through a fresh GF/B filter. The clarified methanol extract was subsequently dried under reduced pressure at 45° C. The dried crudes (yellow-golden oil) from both solvent extractions were redissolved in methanol (20 mL), diluted with 180 mL of distilled water, and the resultant suspensions were applied to a Waters C18 (20 cc) Sep-Pak cartridge for solid phase extraction (SPE) according to the manufacturer's directions. The loaded SPE cartridge was purged of unbound or undesired compounds with 40 mL of distilled water followed by 40 mL of a 1:9 methanol/water solution. The compounds of interest then were eluted from the SPE cartridge with 40 mL methanol/water washes of increasing methanol content (20%, 30%, 40%, 50%, 60%, 100%). The title compound eluted from the SPE cartridge in the 60% and 100% methanol washes. The eluent containing the title compound was stripped of solvent at 45° C. by a stream of nitrogen gas. The resultant aqueous suspension was applied to a fresh SPE cartridge and eluted with 40 mL acetonitrile/water washes of increasing acetonitrile content (20%, 40%, 50%, 55%, 60%, 65%, 70%, 75%, 80%, 85%, 90%, 100%) to separate it from the residual parent compound. The title compound eluted from the SPE cartridge in the 40% and 50% acetonitrile washes. The eluent containing the title compound was stripped of solvent at 45° C. by a stream of nitrogen gas. The resultant aqueous suspension was extracted 3 times with equal volumes of ethyl acetate to remove the title compound. The ethyl acetate extracts were combined and taken to dryness under reduced pressure. The dried crude was dissolved in 1 mL of methanol, clarified by membrane filtration (0.2 micron porosity), and subjected to reversed phase high performance liquid chromatography (HPLC Method) to isolate the title compound.

| HPLC Method | |
|---|---|
| Column: | Nova-Pak C18, 7.8 × 300 mm. |
| Mobile phase: | gradient from 8–18 min.; (20→50)% acetonitrile: (80→50)% aqueous buffer [10 mM ammonium acetate, adjusted to pH 4.5 with acetic acid]. |
| Flow rate: | 1.5 mL/min. |
| Monitor: | UV absorbance at 261 nm; photodiode array at 195–400 nm (4.8 nm slit). |
| Run Time: | 50 min. |

The title compound had a retention time of 28.9 minutes and UV-light absorbance maxima at 205 nm, 219 nm, 261 nm and 300 nm. Eluting HPLC mobile phase fractions containing the title compound were collected, stripped of solvent by a stream of nitrogen gas at 45° C., and loaded onto a fresh SPE cartridge for salt removal by solid phase extraction according to the manufacturer's directions. The title compound was eluted from the SPE cartridge with 40 mL of 100% methanol. This eluate was concentrated to dryness under reduced pressure to produce 6.3 mg of the title compound. The overall process yield was 6.1%.

MS (APCl$^+$): 567 (M+H)

$^1$H-NMR (400 MHz, CD$_3$OD): δ 1.02 (s, 9H), 1.48–1.76 (m, 2H), 1.91 (m, 2H), 2.09 (s, 3H), 2.54 (m, 1H), 2.78–2.92 (m, 2H), 2.98–3.24 (m, 2H), 3.42 (s, 3H), 3.96 (d, 1H), 4.24 (m, 2H), 4.42 (m, 1H), 4.68 (m, 2H), 6.02 (s, 2H), 6.66 (s, 1H), 6.86 (m, 1H), 7.02 (m, 1H), 7.07 (m, 1H).

EXAMPLE 149 racemic 1-{(1R,7S,9R)-[1-tert-butyl-7-(2,3-dimethoxy-phenyl)-2-hydroxy-5-methyl-10-oxo-1,2,9,10-tetrahydro-7H-3,8-dioxa-10a-aza-cyclohepta[de]naphthalen-9-yl]-acetyl}-piperidine-4-carboxylic acid Twenty-five mL of IOWA Medium (anhydrous dextrose, 20 g; yeast extract, 5 g; dipotassium hydrogen phosphate, 5 g; sodium chloride, 5 g; soybean flour, 5 g; distilled water, 1 L; adjusted to pH 7.2 with 1 N sulfuric acid) were added to each of twenty 125-mL Delong flasks with Morton closures and the resulting combinations were steam-sterilized for 30 minutes at 15 psig and 121° C. Each flask was aseptically inoculated with 0.25 mL of a cryogenically stored (−80° C.) axenic stock of *Absidia pseudocylindrospora* (American Type Culture Collection strain 24169) spores. The inoculated flasks were mounted vertically on a rotary shaker (1-inch throw) and shaken at 250 rpm and 28° C. for 2 days. Then, 5 mL of a Tween 80/glycerol solution (Tween 80 [polyoxyethylenesorbitan monooleate], 25 g; glycerol, 100 g; distilled water, 975 mL; sterilized by membrane filtration [0.2 micron porosity]) was added to each of the 20 flasks containing fungal growth in IOWA Medium. Racemic 1-{(1R,7S,9R)-[1-tert-butyl-7-(2,3-dimethoxy-phenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid (i.e., substrate) was dissolved in a 1:1 methanol/dimethylsulfoxide solution (10 mg/mL). To each of the 20 biotransformation flasks, 0.25 mL of the resulting solution was aseptically added to give an initial substrate concentration of 100 mcg/mL. The dosed flasks were remounted vertically on the rotary shaker and shaken at 250 rpm and 28° C. for 1 day. Again, to each of the 20 biotransformation flasks, 0.25 mL of the solution of substrate in methanol/dimethylsulfoxide was aseptically added to give a total added substrate concentration of 200 mcg/mL. The dosed flasks were remounted vertically on the rotary shaker and shaken at 250 rpm and 28° C. for an additional 4 days. At the end of the 5-day biotransformation period, the contents of the biotransformation flasks (i.e., broth) were combined and filtered through a Whatman GF/B filter. Each flask was rinsed with distilled water and this aqueous rinse also was filtered and added to the broth filtrate (approx. 850 mL total volume). The filtrate was extracted 3 times with equal volumes of ethyl acetate. For each extraction, the solvent/aqueous mix was centrifuged at 10,000 rpm for 10 min. and the supernatant solvent layer was retained. The 3 ethyl acetate extracts were pooled and taken to dryness under reduced pressure at 45° C. The solids retained on the GF/B filter were extracted with 300 mL methanol. The methanol extract was separated from the extracted solids by filtering through a fresh GF/B filter. The clarified methanol extract was subsequently dried under reduced pressure at 45° C. The dried crudes (yellow-golden oil) from both solvent extractions were redissolved in methanol (20 mL), diluted with 180 mL of distilled water, and the resultant suspensions were applied to a Waters C18 (20 cc) Sep-Pak cartridge for solid phase extraction (SPE) according to the manufacturer's directions. The loaded SPE cartridge was purged of unbound or undesired compounds with 40 mL of distilled water followed by 40 mL of a 1:9 methanol/water solution. The compounds of interest then were eluted from the SPE cartridge with 40 mL methanol/water washes of increasing methanol content (20%, 30%, 40%, 50%, 60%, 100%). The title compound eluted from the SPE cartridge in the 100% methanol wash. The eluent containing the title compound was stripped of solvent at 45° C. by a stream of nitrogen gas. The resultant aqueous suspension was applied to a fresh SPE cartridge and eluted with 40 mL acetonitrile/water washes of increasing acetonitrile content (20%, 40%, 50%, 55%, 60%, 65%, 70%, 75%, 80%, 85%, 90%, 100%) to separate it from the residual parent compound. The title compound eluted from the SPE cartridge in the 40% and 50% acetonitrile washes. The eluent containing the title compound was stripped of solvent at 45° C. by a stream of nitrogen gas. The resultant aqueous suspension was extracted 3 times with equal volumes of ethyl acetate to remove the title compound. The ethyl acetate extracts were combined and taken to dryness under reduced pressure. The dried crude was dissolved in 1 mL of methanol, clarified by membrane filtration (0.2 micron porosity), and subjected to reversed phase high performance liquid chromatography (HPLC Method) to isolate the title compound.

| HPLC Method | |
|---|---|
| Column: | Nova-Pak C18, 7.8 × 300 mm. |
| Mobile phase: | gradient from 8–18 min.; (20→50)% acetonitrile: (80→50)% aqueous buffer [10 mM ammonium acetate, adjusted to pH 4.5 with acetic acid]. |
| Flow rate: | 1.5 mL/min. |
| Monitor: | UV absorbance at 261 nm; photodiode array at 195–400 nm (4.8 nm slit). |
| Run Time: | 50 min. |

The title compound had a retention time of 29.9 minutes and UV-light absorbance maxima at 205 nm, 219 nm, 261 nm and 300 nm. HPLC mobile phase fractions containing the title compound were retained and extracted with chloroform. The chloroform extraction layer was recovered, dried over anhydrous sodium sulfate, filtered to remove solids, and concentrated to dryness under reduced pressure to produce 2.6 mg of the title compound. The overall process yield was 2.6%.

MS (APCl$^+$): 597 (M+H)

$^1$H-NMR (400 Mhz, CD$_3$OD): δ 1.11 (d, 3H), 1.12 (d, 3H), 1.5–1.76 (m, 2H), 1.91 (m, 2H), 2.09 (s, 3H), 2.45 (m, 1H), 2.74–2.92 (m, 2H), 2.98–3.22 (m, 2H), 3.43 (s, 3H), 3.62 (m, 2H), 3.84 (m, 3H), 3.96 (m, 1H) 4.28 (m, 2H), 4.61 (m, 1H), 4.70 (m, 2H), 5.98 (s, 2H), 6.69 (s, 1H), 7.04 (m, 1H), 7.17 (m, 1H), 7.21 (m, 1H).

EXAMPLE 150 racemic 1-{(1R,7S,9R)-[7-(2,3-Dimethoxy-phenyl)-1-(2-hydroxy-1,1-dimethyl-ethyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid Twenty-five mL of IOWA Medium (anhydrous dextrose, 20 g; yeast extract, 5 g; dipotassium hydrogen phosphate, 5 g; sodium chloride, 5 g; soybean flour, 5 g; distilled water, 1 L; adjusted to pH 7.2 with 1 N sulfuric acid) were added to each of twenty 125-mL Delong flasks with Morton closures and the resulting combinations were steam-sterilized for 30 minutes at 15 psig and 121° C. Each flask was aseptically inoculated with 0.25 mL of a cryogenically stored (−80° C.) axenic stock of Absidia pseudocylindrospora (American Type Culture Collection strain 24169) spores. The inoculated flasks were mounted vertically on a rotary shaker (1-inch throw) and shaken at 250 rpm and 28° C. for 2 days. Then, 5 mL of a Tween 80/glycerol solution (Tween 80 [polyoxyethylenesorbitan monooleate], 25 g; glycerol, 100 g; distilled water, 975 mL; sterilized by membrane filtration [0.2 micron porosity]) was added to each of the 20 flasks containing fungal growth in IOWA Medium. Racemic 1-{(1R,7S,9R)-[1-tert-butyl-7-(2,3-dimethoxy-phenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid (i.e., substrate) was dissolved in a 1:1 methanol/dimethylsulfoxide solution (10 mg/mL). To each of the 20 biotransformation flasks, 0.25 mL of the resulting solution was aseptically added to give an initial substrate concentration of 100 mcg/mL. The dosed flasks were remounted vertically on the rotary shaker and shaken at 250 rpm and 28° C. for 1 day. Again, to each of the 20 biotransformation flasks, 0.25 mL of the solution of substrate in methanol/dimethylsulfoxide was aseptically added to give a total added substrate concentration of 200 mcg/mL. The dosed flasks were remounted vertically on the rotary shaker and shaken at 250 rpm and 28° C. for an additional 4 days. At the end of the 5-day biotransformation period, the contents of the biotransformation flasks (i.e., broth) were combined and filtered through a Whatman GF/B filter. Each flask was rinsed with distilled water and this aqueous rinse also was filtered and added to the broth filtrate (approx. 850 mL total volume). The filtrate was extracted 3 times with equal volumes of ethyl acetate. For each extraction, the solvent/aqueous mix was centrifuged at 10,000 rpm for 10 min. and the supernatant solvent layer was retained. The 3 ethyl acetate extracts were pooled and taken to dryness under reduced pressure at 45° C. The solids retained on the GF/B filter were extracted with 300 mL methanol. The methanol extract was separated from the extracted solids by filtering through a fresh GF/B filter. The clarified methanol extract was subsequently dried under reduced pressure at 45° C. The dried crudes (yellow-golden oil) from both solvent extractions were redissolved in methanol (20 mL), diluted with 180 mL of distilled water, and the resultant suspensions were applied to a Waters C18 (20 cc) Sep-Pak cartridge for solid phase extraction (SPE) according to the manufacturer's directions. The loaded SPE cartridge was purged of unbound or undesired compounds with 40 mL of distilled water followed by 40 mL of a 1:9 methanol/water solution. The compounds of interest then were eluted from the SPE cartridge with 40 mL methanol/water washes of increasing methanol content (20%, 30%, 40%, 50%, 60%, 100%). The title compound eluted from the SPE cartridge in the 100% methanol wash. The eluent containing the title compound was stripped of solvent at 45° C. by a stream of nitrogen gas. The resultant aqueous suspension was applied to a fresh SPE cartridge and eluted with 40 mL acetonitrile/water washes of increasing acetonitrile content (20%, 40%, 50%, 55%, 60%, 65%, 70%, 75%, 80%, 85%, 90%, 100%) to separate it from the residual parent compound. The title compound eluted from the SPE cartridge in the 50% acetonitrile wash. The eluent containing the title compound was stripped of solvent at 45° C. by a stream of nitrogen gas. The resultant aqueous suspension was extracted 3 times with equal volumes of ethyl acetate to remove the title compound. The ethyl acetate extracts were combined and taken to dryness under reduced pressure. The dried crude was dissolved in 1 mL of methanol, clarified by membrane filtration (0.2 micron porosity), and subjected to reversed phase high performance liquid chromatography (HPLC Method) to isolate the title compound.

| HPLC Method | |
|---|---|
| Column: | Nova-Pak C18, 7.8 × 300 mm. |
| Mobile phase: | gradient from 8–18 min.; (20–>50)% acetonitrile: (80–>50)% aqueous buffer [10 mM ammonium acetate, adjusted to pH 4.5 with acetic acid]. |
| Flow rate: | 1.5 mL/min. |
| Monitor: | UV absorbance at 261 nm; photodiode array at 195–400 nm (4.8 nm slit). |
| Run Time: | 50 min. |

The title compound had a retention time of 34.2 minutes and UV-light absorbance maxima at 205 nm, 261 nm and 300 nm. HPLC mobile phase fractions containing the title compound were retained and extracted with chloroform. The chloroform extraction layer was recovered, dried over anhydrous sodium sulfate, filtered to remove solids, and concentrated to dryness under reduced pressure to produce 3.1 mg of the title compound. The overall process yield was 3.1%.

MS (APCl$^+$): 597 (M+H)

$^1$H-NMR (400 Mhz, CD$_3$OD): δ 0.98 (s, 9H), 1.59 (m, 2H), 1.89 (m, 2H), 2.09 (s, 3H), 2.51 (m, 1H), 2.70 ( m, 1H), 2.81 (m, 1H), 2.98–3.14 (m, 2H), 3.43 (s, 3H), 3.83 (s, 3H), 4.00 (m, 1H), 4.33 (m, 1H), 4.47 (s, 1H), 4.71 (m, 1H), 5.77 (s, 1H), 6.00 (s, 1H), 6.08 (m, 1H), 6.68 (s, 1H), 7.03 (m, 1H), 7.16 (m, 2H).

It should be understood that the invention is not limited to the particular embodiments shown and described herein, but that various changes and modifications may be made without departing from the spirit and scope of this novel concept as defined by the following claims.

What is claimed is:

1. A compound of Formula I

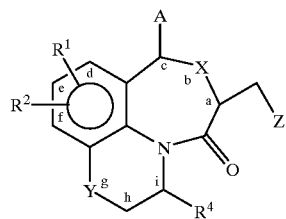

Formula I or a pharmaceutically acceptable salt of said compound wherein A is phenyl or naphthyl, said phenyl or naphthyl optionally mono-, di- or tri-substituted independently with R$^3$, R$^9$ and R$^{10}$;

X is oxy or thio;

Y is oxy, thio or methylene;

R$^1$ and R$^2$ are each independently hydrogen, halo, hydroxyl, trifluoromethyl, (C$_1$–C$_4$)alkyl, fluorinated (C$_1$–C$_4$)alkyl having from 1 to 9 fluorines, (C$_1$–C$_4$) alkoxy, fluorinated (C$_1$–C$_4$)alkoxy having from 1 to 9 fluorines, (C$_1$–C$_4$)alkylthio, (C$_1$–C$_4$)alkylsulfinyl, (C$_1$–C$_4$)alkylsulfonyl, phenyl, amino, mono-N- or di-N,N-(C$_1$–C$_4$)alkylamino, carboxyl, (C$_1$–C$_4$) alkoxycarbonyl, carbamoyl, mono-N- or di-N,N-(C$_1$–C$_4$)alkylcarbamoyl, (C$_1$–C$_4$)alkanoylamino, fluorinated (C$_1$–C$_4$)alkanoylamino having from 1 to 9 fluorines, (C$_1$–C$_4$)alkylsulfonylamino or fluorinated (C$_1$–C$_4$)alkylsulfonylamino having from fluorines, (C$_1$–C$_6$)alkanoyl, (C$_1$–C$_6$)alkanoyl(C$_1$–C$_6$)alkyl, oxazolyl, thiazolyl, isoxazolyl, pyrazolyl or isothiazolyl wherein said preceding heterocycles are carbon linked or wherein R$^1$ and R$^2$ can be taken together to form a five, six or seven membered carbocyclic ring or can be taken together to form methylenedioxyl, ethylenedioxyl or propylenedioxyl and such rings formed by taking R$^1$ and R$^2$ together are fused at the e and f positions;

R$^3$, R$^9$ and R$^{10}$ are each independently hydrogen, halo, hydroxyl, trifluoromethyl, (C$_1$–C$_4$)alkyl, fluorinated (C$_1$–C$_4$)alkyl having from 1 to 9 fluorines, (C$_1$–C$_4$) alkoxy, fluorinated (C$_1$–C$_4$)alkoxy having from 1 to 9 fluorines, (C$_1$–C$_4$)alkylthio, (C$_1$–C$_4$)alkylsulfinyl, (C$_1$–C$_4$)alkylsulfonyl, phenyl, amino, mono-N- or di-N,N-(C$_1$–C$_4$)alkylamino, carboxyl, (C$_1$–C$_4$) alkoxycarbonyl, carbamoyl, mono-N- or di-N,N-(C$_1$–C$_4$)alkylcarbamoyl, (C$_1$–C$_4$)alkanoylamino, fluorinated (C$_1$–C$_4$)alkanoylamino having from 1 to 9 fluorines, (C$_1$–C$_4$)alkylsulfonylamino or fluorinated (C$_1$–C$_4$)alkylsulfonylamino having from 1 to 9 fluorines, (C$_1$–C$_6$)alkanoyl, (C$_1$–C$_6$)alkanoyl(C$_1$–C$_6$) alkyl, oxazolyl, thiazolyl, isoxazolyl, pyrazolyl or isothiazolyl wherein said preceding heterocycles are carbon linked or wherein R$^3$ and R$^9$ can be taken together to form a five, six or seven membered carbocyclic ring or can be taken together to form methylenedioxyl, ethylenedioxyl or propylenedioxyl ring;

R$^4$ is phenyl, (C$_1$–C$_7$)alkyl, (C$_1$–C$_7$)alkenyl or (C$_3$–C$_4$) cycloalkylmethyl wherein said phenyl, (C$_1$–C$_7$)alkyl, (C$_1$–C$_7$)alkenyl or (C$_3$–C$_4$)cycloalkylmethyl are optionally mono-, di-, or tri-substituted independently with hydroxyl, oxo, (C$_1$–C$_4$)alkyl, amino, carboxy, thiol, (C$_1$–C$_4$)alkoxy, fluorinated (C$_1$–C$_4$)alkoxy having from 1 to 9 fluorines, (C$_1$–C$_4$)alkylthio, (C$_1$–C$_4$) alkylsulfinyl, (C$_1$–C$_4$)alkylsulfonyl, mono-N- or di-N, N-(C$_1$–C$_4$)alkylamino, mono-N- or di-N,N-(C$_1$–C$_4$) alkylaminocarbonyl, or mono-N-or di-N,N(C$_1$–C$_4$) alkylaminosulfonyl; or R$^4$ is (C$_1$–C$_7$)alkyl substituted with 1 to 15 fluorines or (C$_3$–C$_4$)cycloalkylmethyl substituted with 1 to 9 fluorines; or R$^4$ is het(C$_1$–C$_6$)alkyl wherein het is a 4–7 member saturated, partially unsaturated or fully unsaturated heterocycle containing independently one to three O, N or S atoms and said het is optionally mono-substituted with (C$_1$–C$_4$)alkyl, (C$_1$–C$_4$)alkoxy, hydroxyl, halo, amino or mono-N- or di-N,N-(C$_1$–C$_4$)alkylamino;

Z is carboxyl, (C$_1$–C$_4$)alkoxycarbonyl, aminocarbonyl, cyano, hydroxyaminocarbonyl, —C(O)N(H)SO$_2$R$^5$, tetrazol-5-yl, 4,5-dihydro-5-oxo-1,2,4-oxadiazol-3-yl, tetrazol-5-yl-aminocarbonyl, 3-oxoisoxazolidin-4-ylaminocarbonyl, $N(R^{12})CONR^{13}R^{14}$, $N(R^{12})CO_2(C_1-C_4)$alkyl, $N(R^{12})COR^{15}$,

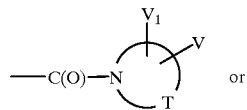 or mono-N- or di-N,N-$(C_1-C_6)$alkylaminocarbonyl wherein each of said $(C_1-C_6)$alkyl is optionally mono- or di-substituted independently with V or $V^1$, or —C(O)N(H)—$(C_0-C_4)$alkyl-$R^{20}$ wherein said $(C_0-C_4)$alkyl may optionally be mono-substituted with carboxyl and wherein $R^{20}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $R^{20}$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, wherein said $(C_1-C_6)$alkyl substituent is also optionally substituted with from one to nine flourines;

$R^{12}$, $R^{13}$ and $R^{14}$ are each independently H or $(C_1-C_4)$alkyl;

$R^{15}$ is H or $(C_1-C_4)$alkyl;

$R^5$ is H, amino or mono-N- or di-N,N-$(C_1-C_4)$alkylamino; or $R^5$ is $(C_1-C_4)$alkyl optionally substituted with 1 to 9 fluorines, amino, mono-N- or di-N,N-$(C_1-C_4)$alkylamino, carboxyl, $(C_1-C_4)$alkoxycarbonyl, carbamoyl or mono-N- or di-N,N-$(C_1-C_4)$alkylcarbamoyl; phenyl optionally mono- or di-substituted independently with methyl, methoxyl, fluoro, trifluoromethoxyl, carboxyl, $(C_1-C_4)$alkoxycarbonyl, methylthio, methylsulfinyl, methylsulfonyl, $(C_1-C_4)$alkylsulfonylamino or mono-N- or di-N,N-$(C_1-C_4)$alkylaminosulfonyl; or $R^5$ is thiazolyl, isothiazolyl, thienyl, furyl, pyridinyl or any of said heterocycles optionally mono-substituted with carboxyl or mono- or di-substituted with methyl;

T forms a four to seven membered mono- or di-aza, saturated ring, said ring optionally containing thio and said ring optionally mono-substituted on carbon with hydroxyl; and V and $V^1$ are each independently hydrogen, hydroxyl, amino, mono-N- or di-N,N-$(C_1-C_4)$alkylamino, carbamoyl, mono-N- or di-N,N-$(C_1-C_4)$alkylcarbamoyl, carboxyl, $(C_1-C_4)$alkoxy, fluorinated $(C_1-C_4)$alkoxy having from 1 to 9 fluorines, $(C_1-C_4)$alkoxycarbonyl, aminocarbonyl, cyano, thiol, sulfamoyl, $(C_1-C_4)$alkylthio, $(C_1-C_4)$alkylsulfonyl, $(C_1-C_4)$alkylsulfinyl, $(C_1-C_4)$alkylsulfonylamino, fluorinated $(C_1-C_4)$alkylsulfonylamino having from 1 to 9 fluorines, mono-N- or di-N,N-$(C_1-C_4)$alkylaminosulfonyl, $(C_1-C_4)$alkanoylamino, fluorinated $(C_1-C_4)$alkanoylamino having from 1 to 9 fluorines, ureido, mono-N- or di-N,N-$(C_1-C_4)$alkyl ureido, imidazolyl, pyridyl, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl or $(C_0-C_6)$alkyl said $(C_0-C_6)$ alkyl optionally mono- or di-substituted independently with carboxyl or $(C_1-C_4)$alkoxycarbonyl.

2. A compound as recited in claim 1 wherein the $C^a$ and $C^i$ substituents are cis and the $C^c$ substituent is trans to the $C^a$ and $C^i$ substituents;

A is phenyl optionally substituted independently with $R^3$, $R^9$ and $R^{10}$;

$R^1$ and $R^2$ are each independently hydrogen, halo, (Cl-$C_4$)alkyl, (Cl-$C_4$)alkoxy, hydroxy, trifluoromethyl, $(C_1-C_4)$alkylthio, fluorinated $(C_1-C_4)$alkoxy having from 1 to 9 fluorines or $R^1$ and $R^2$ taken together form an ethylenedioxy ring;

$R^3$, $R^9$ and $R^{10}$ are each independently hydrogen, halo, $(C_1-C_4)$alkyl, $(C,-C_4)$alkoxy, hydroxy, trifluoromethyl, $(C_1-C_4)$alkylthio, fluorinated $(C_1-C_4)$alkoxy having from 1 to 9 fluorines or $R^3$ and $R^9$ taken together form an $(C_1-C_3)$alkylenedioxy ring;

$R^4$ is $(C_1-C_7)$alkyl;

X is oxy;

Y is oxy;

$V^1$ is H;

V is carboxyl or $(C_1-C_4)$alkoxycarbonyl; and

Z is carboxyl or

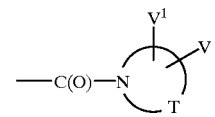

or a pharmaceutically acceptable salt thereof.

3. A compound as recited in claim 2 wherein $R^3$ and $R^9$ are each independently hydrogen, halo, trifluoromethoxy, $(C_1-C_4)$alkoxy or taken together form a $(C_1-C_3)$alkylenedioxy ring;

$R^{10}$ is hydrogen;

$R^2$ is hydrogen; and

T forms a piperidin-1-yl ring or a pharmaceutically acceptable salt thereof.

4. A compound as recited in claim 3 wherein $R^1$ is methyl at the $C^e$ position;

$R^3$ is 2-methoxy;

$R^9$ is 3-methoxy;

$R^4$ is tert-butyl; and

Z is 4-carboxylpiperidin-1-ylcarbonyl or a pharmaceutically acceptable salt thereof.

5. A compound as recited in claim 3 wherein $R^1$ is methyl at the $C^e$ position;

$R^3$ is 2-methoxy;

$R^9$ is 3-methoxy;

$R^4$ is tert-butyl; and

Z is 3-carboxylpiperidin-1-ylcarbonyl or a pharmaceutically acceptable salt thereof.

6. A compound as recited in claim 5 wherein
Z is (3R)-3-carboxylpiperidin-1-ylcarbonyl or a pharmaceutically acceptable salt thereof.
7. A compound as recited in claim 3 wherein
$R^1$ is methyl at the $C^e$ position;
$R^3$ is 2-chloro
$R^9$ is hydrogen;
$R^4$ is tert-butyl; and
Z is 3-carboxylpiperidin-1-ylcarbonyl or a pharmaceutically acceptable salt thereof.
8. A compound as recited in claim 3 wherein
$R^1$ is methyl at the $C^e$ position;
$R^3$ is 2-methoxy;
$R^9$ is hydrogen;
$R^4$ is tert-butyl; and
Z is 4-carboxylpiperidin-1-ylcarbonyl or a pharmaceutically acceptable salt thereof.
9. A compound as recited in claim 3 wherein
$R^1$ is chloro at the $C^e$ position;
$R^3$ is 2-methoxy;
$R^9$ is 3-methoxy;
$R^4$ is tert-butyl; and
Z is 4-carboxylpiperidin-1-ylcarbonyl or a pharmaceutically acceptable salt thereof.
10. A compound as recited in claim 3 wherein
$R^1$ is chloro at the $C^e$ position;
$R^3$ is 2-methoxy;
$R^9$ is hydrogen;
$R^4$ is tert-butyl; and
Z is 4-carboxylpiperidin-1-ylcarbonyl or a pharmaceutically acceptable salt thereof.
11. A compound as recited in claim 1 wherein
the $C^a$ and $C^i$ substituents are cis and the $C^c$ substituent is trans to the $C^a$ and $C^i$ substituents;
A is phenyl optionally substituted independently with $R^3$, $R^9$ and $R^{10}$;
$R^1$ and $R^2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines or $R^1$ and $R^2$ taken together form an ethylenedioxy ring;
$R^4$ is $(C_1-C_7)$alkyl;
X is oxy;
Y is methylene;
$V^1$ is H;
V is carboxyl or $(C_1-C_4)$alkoxycarbonyl; and
Z is carboxyl or

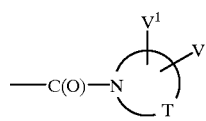

or a pharmaceutically acceptable salt thereof.
12. A compound as recited in claim 11 wherein
$R^3$ and $R^9$ are each independently hydrogen, halo, trifluoromethoxy, $(C_1-C_4)$alkoxy or taken together form a $(C_1-C_3)$alkylenedioxy ring;
$R^{10}$ is hydrogen;
$R^2$ is hydrogen; and
T forms a piperidin-1-yl ring or a pharmaceutically acceptable salt thereof.
13. A compound as recited in claim 12 wherein
$R^1$ is methyl at the $C^e$ position;
$R^3$ is 2-methoxy;
$R^9$ is 3-methoxy;
$R^4$ is tert-butyl; and
Z is 3-carboxylpiperidin-1-ylcarbonyl or a pharmaceutically acceptable salt thereof.
14. A compound as recited in claim 12 wherein
$R^1$ is methyl at the $C^e$ position;
$R^3$ is 2-methoxy;
$R^9$ is 3-methoxy;
$R^4$ is tert-butyl; and
Z is 2-carboxylpiperidin-1-ylcarbonyl or a pharmaceutically acceptable salt thereof.
15. A compound as recited in claim 12 wherein
$R^1$ is chloro at the $C^e$ position;
$R^3$ and $R^9$ are taken together to form 2,3-ethylenedioxyl;
$R^4$ is tert-butyl; and
Z is 4-carboxylpiperidin-1-ylcarbonyl or a pharmaceutically acceptable salt thereof.
16. A compound as recited in claim 12 wherein
$R^1$ is chloro at the $C^e$ position;
$R^3$ and $R^9$ are taken together to form 2,3-ethylenedioxyl;
$R^4$ is tert-butyl; and
Z is 3-carboxylpiperidin-1-ylcarbonyl or a pharmaceutically acceptable salt thereof.
17. A compound as recited in claim 12 wherein
$R^1$ is chloro at the $C^e$ position;
$R^3$ and $R^9$ are taken together to form 2,3-methylenedioxyl;
$R^4$ is tert-butyl; and
Z is 4-carboxylpiperidin-1-ylcarbonyl or a pharmaceutically acceptable salt thereof.
18. A compound as recited in claim 12 wherein
$R^1$ is chloro at the $C^e$ position;
$R^3$ is 2-methoxy;
$R^9$ is hydrogen;
$R^4$ is tert-butyl; and
Z is 4-carboxylpiperidin-1-ylcarbonyl or a pharmaceutically acceptable salt thereof.
19. A compound as recited in claim 12 wherein
$R^1$ is chloro at the $C^e$ position;
$R^3$ is 2-methoxy;
$R^9$ is hydrogen;
$R^4$ is tert-butyl; and
Z is 3-carboxylpiperidin-1-ylcarbonyl or a pharmaceutically acceptable salt thereof.
20. A compound as recited in claim 12 wherein
$R^1$ is methyl at the $C^e$ position;
$R^3$ is 2-methoxy;
$R^9$ is hydrogen;
$R^4$ is tert-butyl; and
Z is 4-carboxylpiperidin-1-ylcarbonyl or a pharmaceutically acceptable salt thereof.
21. A compound as recited in claim 12 wherein
$R^1$ is methyl at the $C^e$ position;
$R^3$ and $R^9$ are taken together to form 2,3-methylenedioxyl;

$R^4$ is tert-butyl; and

Z is 3-carboxylpiperidin-1-ylcarbonyl or a pharmaceutically acceptable salt thereof.

22. A compound as recited in claim 12 wherein $R^1$ is chloro at the $C^e$ position;

$R^3$ is 2-trifluoromethoxy;

$R^9$ is hydrogen;

$R^4$ is tert-butyl; and

Z is 3-carboxylpiperidin-1-ylcarbonyl or a pharmaceutically acceptable salt thereof.

23. A compound as recited in claim 1 wherein the $C^a$ and $C^i$ substituents are cis and the $C^c$ substituent is trans to the $C^a$ and $C^i$ substituents;

A is phenyl optionally substituted independently with $R^3$, $R^9$ and $R^{10}$;

$R^1$ and $R^2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines or $R^1$ and $R^2$ taken together form an ethylenedioxy ring;

$R^4$ is $(C_1-C_7)$alkyl;

X is thio;

Y is oxy;

V is carboxyl, $(C_1-C_4)$alkoxycarbonyl or tetrazol-5-yl;

$V^1$ is H; and

Z is carboxyl or

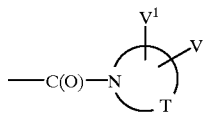

or a pharmaceutically acceptable salt thereof.

24. A compound as recited in claim 23 wherein $R^3$ and $R^9$ are each independently hydrogen, halo, $(C_1-C_4)$alkoxy, trifluoromethoxy, or taken together form a $(C_1-C_3)$alkylenedioxy ring;

$R^{10}$ is hydrogen;

$R^2$ is hydrogen; and

T forms a piperidin-1-yl ring or a pharmaceutically acceptable salt thereof.

25. A compound as recited in claim 24 wherein $R_1$ is methyl at the $C^e$ position;

$R^3$ is 2-methoxy;

$R^9$ is 3-methoxy;

$R^4$ is tert-butyl; and

Z is 4-carboxylpiperidin-1-ylcarbonyl or a pharmaceutically acceptable salt thereof.

26. A compound as recited in claim 1 wherein the $C^a$ and $C^i$ substituents are cis and the $C^c$ substituent is trans to the $C^a$ and $C^i$ substituents;

A is phenyl optionally substituted independently with $R^3$, $R^9$ and $R^{10}$;

$R^1$ and $R^2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines or $R^1$ and $R^2$ taken together form an ethylenedioxy ring;

$R^3$, $R^9$ and $R^{10}$ are each independently hydrogen, $(C_1-C_4)$ alkoxy, halo, trifluoromethoxy or taken together form a $(C_1-C_3)$alkylenedioxy ring;

$R^4$ is $(C_1-C_7)$alkyl;

X is thio;

Y is methylene;

$V^1$ is H;

V is carboxyl, $(C_1-C_4)$alkoxycarbonyl or tetrazol-5-yl; and

Z is carboxyl or

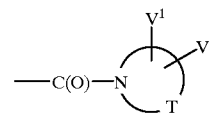

or a pharmaceutically acceptable salt thereof.

27. A compound as recited in claim 26 wherein $R^1$ is chloro at the $C^e$ position;

$R^2$ is hydrogen;

$R^3$ is 2-methoxy;

$R^9$ is hydrogen;

$R^{10}$ is hydrogen $R^4$ is tert-butyl; and

Z is 4-carboxylpiperidin-1-ylcarbonyl or a pharmaceutically acceptable salt thereof.

28. A compound as recited in claim 1 wherein Z is

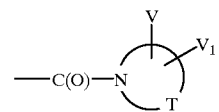

or a pharmaceutically acceptable salt thereof.

29. A compound as recited in claim 28 wherein

T forms a piperidin-1-yl ring or a pharmaceutically acceptable salt thereof.

30. A compound as recited in claim 29 wherein the $C^a$ and $C^i$ substituents are cis and the $C^c$ substituent is trans to the $C^a$ and $C^i$ substituents;

$R^1$ and $R^2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines or $R^1$ and $R^2$ taken together form an ethylenedioxy ring;

$R^3$ and $R^9$ are each independently $(C_1-C_4)$alkoxy or taken together form a $(C_1-C_3)$alkylenedioxy ring;

$R^4$ is $(C_1-C_7)$alkyl; and $R^{10}$ is hydrogen or a pharmaceutically acceptable salt thereof.

31. A compound selected from the group consisting of

1-{[(1R,7S,9R)-1-tert-butyl-7-(2,3-dimethoxyphenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid;

(3R)-1-{[(6S,8R, 10S)-6-tert-butyl-10-(2,3-dimethoxyphenyl)-2-methyl-7-oxo-5,6,7,8-tetrahydro-4H,10H-9-oxa-6a-aza-cyclohepta[de]naphthalen-8-yl]-acetyl}-piperidine-3-carboxylic acid;

1-{[(6S,8R,10S)-6-tert-butyl-10-(2,3-dimethoxyphenyl)-2-methyl-7-oxo-5,6,7,8-tetrahydro-4H,10H-9-oxa-6a-aza-cyclohepta[de]naphthalen-8-yl]-acetyl}-piperidine-3-carboxylic acid;

(2R)-1-{6S,8R, 10S-[6-tert-butyl-10-(2,3-dimethoxyphenyl)-2-methyl-7-oxo-5,6,7,8-tetrahydro- 4H,10H-9-oxa-6a-aza-cyclohepta[de]naphthalen-8-yl]-acetyl}-2R-piperidine-2-carboxylic acid;

1-{[(6S,8R,10S)-6-tert-butyl-10-(2,3-dihydro-benzo[1,4]dioxin-5-yl)-2-chloro-7-oxo-5,6,7,8-tetrahydro-4H,10H-9-oxa-6a-aza-cyclohepta[de]naphthalen-8-yl]-acetyl}-piperidine-4-carboxylic acid;

1-{[(6S,8R,10S)-6-tert-butyl-10-(2,3-dihydro-benzo[1,4]dioxin-5-yl)-2-chloro-7-oxo-5,6,7,8-tetrahydro-4H,10H-9-oxa-6a-aza-cyclohepta[de]naphthalen-8-yl]-acetyl}-piperidine-3-carboxylic acid;

(3R)-1-{[(6S,8R,10S)-6-tert-butyl-10-(2,3-dihydro-benzo[1,4]dioxin-5-yl)-2-chloro-7-oxo-5,6,7,8-tetrahydro-4H,10H-9-oxa-6a-aza-cyclohepta[de]naphthalen-8-yl]-acetyl}-piperidine-3-carboxylic acid; and 1-{[(6S,8R,10S)-6-tert-butyl-10-(benzo[1,3]dioxol-4-yl)-2-chloro-7-oxo-5,6,7,8-tetrahydro-4H,10H-9-oxa-6a-aza-cyclohepta[de]naphthalen-8-yl]-acetyl}-piperidine-4-carboxylic acid or the pharmaceutically acceptable salts of said compounds.

32. A compound selected from the group consisting of

1-{[(6S,8R,10S)-6-tert-butyl-10-(2-methoxyphenyl)-2-chloro-7-oxo-5,6,7,8-tetrahydro-4H,10H-9-oxa-6a-aza-cyclohepta[de]naphthalen-8-yl]-acetyl}-piperidine-4-carboxylic acid;

1-{[(6S,8R,10S)-6-tert-butyl-10-(2-methoxyphenyl)-2-chloro-7-oxo-5,6,7,8-tetrahydro-4H,10H-9-oxa-6a-aza-cyclohepta[de]naphthalen-8-yl]-acetyl}-piperidine-3-carboxylic acid;

(3R)-1-{[(6S,8R,10S)-6-tert-butyl-10-(2-methoxyphenyl)-2-chloro-7-oxo-5,6,7,8-tetrahydro-4H,10H-9-oxa-6a-aza-cyclohepta[de]naphthalen-8-yl]-acetyl}-piperidine-3-carboxylic acid;

1-{[(6S,8R,10S)-6-tert-butyl-10-(2-trifluoromethoxyphenyl)-2-chloro-7-oxo-5,6,7,8-tetrahydro-4H,10H-9-oxa-6a-aza-cyclohepta[de]naphthalen-8-yl]-acetyl}-piperidine-3-carboxylic acid;

(3R)-1-{[(6S,8R,10S)-6-tert-butyl-10-(2-trifluoromethoxyphenyl)-2-chloro-7-oxo-5,6,7,8-tetrahydro-4H,10H-9-oxa-6a-aza-cyclohepta[de]naphthalen-8-yl]-acetyl}-piperidine-3-carboxylic acid;

1-{[(6S,8R,10S)-6-tert-butyl-10-(benzo[1,3]dioxol-4-yl)-2-methyl-7-oxo-5,6,7,8-tetrahydro-4H,10H-9-oxa-6a-aza-cyclohepta[de]naphthalen-8-yl]-acetyl}-piperidine-3-carboxylic acid;

(3R)-1-{[(6S,8R,10S)-6-tert-butyl-10-(benzo[1,3]dioxol-4-yl)-2-methyl-7-oxo-5,6,7,8-tetrahydro-4H,10H-9-oxa-6a-aza-cyclohepta[de]naphthalen-8-yl]-acetyl}-piperidine-3-carboxylic acid;

(3R)-1-{[(1R,7S,9R)-1-tert-butyl-7-(2,3-dimethoxy-phenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid;

1-{[(1R,7S,9R)-1-tert-butyl-7-(2,3-dimethoxy-phenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid;

1-{[(1R,7S,9R)-1-tert-butyl-7-(2-chlorophenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid;

(3R)-1-{[(1R,7S,9R)-1-tert-butyl-7-(2-chlorophenyl)-5-methyl-10-oxo-1,2,9,10-tetrahydro-7H-3,8-dioxa-10a-aza-cyclohepta[de]naphthalen-9-yl]-acetyl}-piperidine-3-carboxylic acid or the pharmaceutically acceptable salts of said compounds.

33. A compound selected from the group consisting of

1-{[(1R,7S,9R)-1-tert-butyl-7-(2,3-dimethoxyphenyl)-5-chloro-10-oxo-1,2,9,10-tetrahydro-7H-3,8-dioxa-10a-aza-cyclohepta[de]naphthalen-9-yl]-acetyl}-piperidine-4-carboxylic acid;

1-{[(1R,7S,9R)-1-tert-butyl-7-(2-methoxyphenyl)-5-chloro-10-oxo-1,2,9,10-tetrahydro-7H-3,8-dioxa-10a-aza-cyclohepta[de]naphthalen-9-yl]-acetyl}-piperidine-4-carboxylic acid;

1-{[(1R,7S,9R)-1-tert-butyl-7-(2-methoxyphenyl)-5-methyl-10-oxo-1,2,9,10-tetrahydro-7H-3,8-dioxa-10a-aza-cyclohepta[de]naphthalen-9-yl]-acetyl}-piperidine-4-carboxylic acid;

1-{[(1R,7S,9R)-1-tert-butyl-7-(2,3-dimethoxyphenyl)-5-methyl-10-oxo-1,2,9,10-tetrahydro-7H-3-oxa-8-thia-10a-aza-cyclohepta[de]naphthalen-9-yl]-acetyl}-piperidine-4-carboxylic acid;

1-{[(6S,8R,10S)-6-tert-butyl-10-(2-methoxyphenyl)-2-chloro-7-oxo-5,6,7,8-tetrahydro-4H,10H-9-thia-6a-aza-cyclohepta[de]naphthalen-8-yl]-acetyl}-piperidine-4-carboxylic acid;

1-{[(6S,8R,10S)-6-tert-butyl-10-(2-methoxyphenyl)-2-methyl-7-oxo-5,6,7,8-tetrahydro-4H,10H-9-oxa-6a-aza-cyclohepta[de]naphthalen-8-yl]-acetyl}-piperidine-4-carboxylic acid or the pharmaceutically acceptable salts of said compounds.

34. A method for treating hypercholesterolemia which comprises administering to a mammal in need of such treatment a hypercholesterolemic treating amount of a compound of claim 1 or a pharmaceutically acceptable salt of said compound.

35. A pharmaceutical composition which comprises an amount of a compound of claim 1 or a pharmaceutically acceptable salt of said compound and a pharmaceutically acceptable carrier, vehicle or diluent.

* * * * *